US010683501B2

(12) United States Patent
Zimmermann et al.

(10) Patent No.: US 10,683,501 B2
(45) Date of Patent: *Jun. 16, 2020

(54) TRANSTHYRETIN (TTR) IRNA COMPOSITIONS AND METHODS OF USE THEREOF FOR TREATING OR PREVENTING TTR-ASSOCIATED DISEASES

(71) Applicant: Alnylam Pharmaceuticals, Inc., Cambridge, MA (US)

(72) Inventors: Tracy Zimmermann, Winchester, MA (US); Amy Chan, Tewksbury, MA (US); Vasant R. Jadhav, Sharon, MA (US); Martin A. Maier, Belmont, MA (US); Kallanthottathil G. Rajeev, Wayland, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,362

(22) Filed: Dec. 18, 2018

(65) Prior Publication Data

US 2019/0345492 A1 Nov. 14, 2019

Related U.S. Application Data

(63) Continuation of application No. 15/221,651, filed on Jul. 28, 2016, now Pat. No. 10,208,307.

(Continued)

(51) Int. Cl.
*C12N 15/11* (2006.01)
*A61K 48/00* (2006.01)
(Continued)

(52) U.S. Cl.
CPC ........ *C12N 15/113* (2013.01); *C12N 2310/14* (2013.01); *C12N 2310/315* (2013.01);
(Continued)

(58) Field of Classification Search
CPC .............. C12N 15/113; C12N 2310/14; C12N 2310/315; C12N 2310/322;
(Continued)

(56) References Cited

U.S. PATENT DOCUMENTS 7,250,496 B2  7/2007 Bentwich
7,427,605 B2  9/2008 Davis et al.
(Continued)

FOREIGN PATENT DOCUMENTS

EP        2305805 A1    4/2011
WO   WO-2004/015107 A2  2/2004
(Continued)

OTHER PUBLICATIONS

Agrawal S, et al., Antisense oligonucleotides: towards clinical trials. Trends in Biotechnology, Oct. 1996, vol. 14, pp. 376-387.
(Continued)

*Primary Examiner* — Terra C Gibbs
(74) *Attorney, Agent, or Firm* — McCarter & English, LLP; Maria Laccotripe Zacharakis; Deborah L. Nagle

(57) ABSTRACT

The present invention provides iRNA agents, e.g., double stranded iRNA agents, that target the transthyretin (TTR) gene and methods of using such iRNA agents for treating or preventing TTR-associated diseases.

28 Claims, 18 Drawing Sheets

Specification includes a Sequence Listing.

Related U.S. Application Data

(60) Provisional application No. 62/287,518, filed on Jan. 27, 2016, provisional application No. 62/199,563, filed on Jul. 31, 2015.

(51) Int. Cl.
*C07H 21/02* (2006.01)
*C07H 21/04* (2006.01)
*C12N 15/113* (2010.01)

(52) U.S. Cl.
CPC .. *C12N 2310/322* (2013.01); *C12N 2310/344* (2013.01); *C12N 2310/351* (2013.01); *C12N 2310/3515* (2013.01); *C12N 2310/3533* (2013.01); *C12N 2320/30* (2013.01)

(58) Field of Classification Search
CPC ...... C12N 2310/351; C12N 2310/3515; C12N 2320/30
See application file for complete search history.

(56) References Cited

U.S. PATENT DOCUMENTS

| | | |
|---|---|---|
| 7,718,629 B2 | 5/2010 | Bumcrot et al. |
| 8,168,775 B2 | 5/2012 | Sah et al. |
| 8,741,866 B2 | 6/2014 | Sah et al. |
| 9,101,643 B2 | 8/2015 | Sah |
| 9,228,186 B2 | 1/2016 | Khvorova et al. |
| 9,399,775 B2 | 7/2016 | Rajeev et al. |
| 9,708,607 B2 | 7/2017 | Rajeev et al. |
| 9,777,270 B2 | 10/2017 | Khvorova et al. |
| 9,796,974 B2 | 10/2017 | Rajeev et al. |
| 10,208,307 B2 * | 2/2019 | Zimmermann ...... C12N 15/113 |
| 2002/0160394 A1 | 10/2002 | Wu |
| 2003/0072794 A1 | 4/2003 | Boulikas |
| 2003/0124616 A1 | 7/2003 | Jacobsen et al. |
| 2003/0143732 A1 | 7/2003 | Fosnaugh et al. |
| 2003/0170891 A1 | 9/2003 | McSwiggen |
| 2003/0191056 A1 | 10/2003 | Walker et al. |
| 2003/0229037 A1 | 12/2003 | Massing et al. |
| 2004/0119010 A1 | 6/2004 | Perryman et al. |
| 2004/0259247 A1 | 12/2004 | Tuschl et al. |
| 2005/0244869 A1 | 11/2005 | Brown-Driver et al. |
| 2005/0276804 A1 | 12/2005 | Smith et al. |
| 2006/0008910 A1 | 1/2006 | MacLachlan et al. |
| 2006/0083780 A1 | 4/2006 | Heyes et al. |
| 2006/0135460 A1 | 6/2006 | Widder et al. |
| 2006/0240093 A1 | 10/2006 | MacLachlan et al. |
| 2006/0263435 A1 | 11/2006 | Davis et al. |
| 2007/0004664 A1 | 1/2007 | McSwiggen et al. |
| 2007/0031844 A1 | 2/2007 | Khvorova et al. |
| 2007/0135372 A1 | 6/2007 | MacLachlan et al. |
| 2007/0207974 A1 | 9/2007 | Khvorova et al. |
| 2007/0281899 A1 | 12/2007 | Bumcrot et al. |
| 2008/0188675 A1 | 8/2008 | Chen et al. |
| 2009/0023215 A1 | 1/2009 | Jessee et al. |
| 2009/0023673 A1 | 1/2009 | Manoharan et al. |
| 2009/0082300 A1 | 3/2009 | Brown-Driver et al. |
| 2009/0149403 A1 | 6/2009 | MacLachlan et al. |
| 2009/0239814 A1 | 9/2009 | Manoharan et al. |
| 2009/0247608 A1 | 10/2009 | Manoharan et al. |
| 2009/0291131 A1 | 11/2009 | MacLachlan et al. |
| 2010/0120893 A1 | 5/2010 | Sah et al. |
| 2010/0130588 A1 | 5/2010 | Yaworski et al. |
| 2010/0167267 A1 | 7/2010 | Schulzknappe et al. |
| 2010/0267069 A1 | 10/2010 | Kiernan et al. |
| 2010/0323381 A1 | 12/2010 | Bergen, III et al. |
| 2010/0324120 A1 | 12/2010 | Chen et al. |
| 2011/0015250 A1 | 1/2011 | Bumcrot et al. |
| 2011/0237646 A1 | 9/2011 | Smith et al. |
| 2011/0256175 A1 | 10/2011 | Hope et al. |
| 2011/0294868 A1 | 12/2011 | Monia et al. |
| 2012/0149109 A1 | 6/2012 | Brown-Driver et al. |
| 2012/0225927 A1 | 9/2012 | Sah et al. |
| 2012/0244207 A1 | 9/2012 | Fitzgerald et al. |
| 2012/0294905 A1 | 11/2012 | Sah |
| 2013/0197055 A1 | 8/2013 | Kamens et al. |
| 2013/0217756 A1 | 8/2013 | Cancilla et al. |
| 2013/0281510 A1 | 10/2013 | Ando et al. |
| 2014/0194493 A1 | 7/2014 | Sah et al. |
| 2016/0304870 A1 | 10/2016 | Brown et al. |
| 2016/0355817 A1 | 12/2016 | Rajeev et al. |
| 2017/0029817 A1 | 2/2017 | Zimmermann et al. |
| 2018/0119144 A1 | 5/2018 | Khvorova et al. |
| 2018/0320182 A1 | 11/2018 | Khvorova et al. |

FOREIGN PATENT DOCUMENTS

| | | |
|---|---|---|
| WO | WO-2004/045543 A2 | 6/2004 |
| WO | WO-2004/080406 A2 | 9/2004 |
| WO | WO-2004/090108 A2 | 10/2004 |
| WO | WO-2005/120152 A2 | 12/2005 |
| WO | WO-2005/121370 A2 | 12/2005 |
| WO | WO-2007/012191 A1 | 2/2007 |
| WO | WO-2008/042973 A2 | 4/2008 |
| WO | WO-2009/002944 A1 | 12/2008 |
| WO | WO-2009/073809 A2 | 6/2009 |
| WO | WO-2009/086558 A1 | 7/2009 |
| WO | WO-2009/127060 A1 | 10/2009 |
| WO | WO-2009/134487 A2 | 11/2009 |
| WO | WO-2010/042877 A1 | 4/2010 |
| WO | WO-2010/048228 A2 | 4/2010 |
| WO | WO-2010/053572 A2 | 5/2010 |
| WO | WO-2010/054406 A1 | 5/2010 |
| WO | WO-2010/078536 A1 | 7/2010 |
| WO | WO-2010/088537 A2 | 8/2010 |
| WO | WO-2010/129709 A1 | 11/2010 |
| WO | WO-2010/144740 A1 | 12/2010 |
| WO | WO-2010/147992 | 12/2010 |
| WO | WO-2010/148013 A2 | 12/2010 |
| WO | WO-2011/056883 A1 | 5/2011 |
| WO | WO-2011/123468 A1 | 10/2011 |
| WO | WO-2011/139917 A1 | 11/2011 |
| WO | WO-2012/037254 A1 | 3/2012 |
| WO | WO-2012/177906 A1 | 12/2012 |
| WO | WO-2013/074974 A2 | 5/2013 |
| WO | WO-2013/075035 A1 | 5/2013 |
| WO | WO-2015/042564 A1 | 3/2015 |
| WO | WO-2016/028649 A1 | 2/2016 |
| WO | WO-2017/023660 A1 | 2/2017 |

OTHER PUBLICATIONS

Akinc A., et al., A combinatorial library of lipid-like materials for delivery of RNAi therapeutics. Nature Biotechnology, 2008, vol. 26, pp. 561-569.

Alnylam Pharmaceuticals Discontinues Revusiran Development, Press Release, Oct. 5, 2016.

Ando Y., et al., "Pathogenesis and Therapy for Transthyretin Related Amyloidosis," Rinsho byori (the Japanese journal of clinical pathology), Feb. 2008, pp. 114-120, vol. 56 (With English Abstract).

Bass B., The short answer. Nature, May 24, 2001, pp. 428-429, vol. 411.

Behlke, "Chemical Modification of siRNAs for In Vivo Use", Oligonucleotides, 18(4) 305-320 2008.

Benson M., et al., Targeted suppression of an amyloidogenic transthyretin with antisense oligonucleotides. Muscle & Nerve, Jan. 18, 2006, pp. 609-618, vol. 33, No. 5.

Berquist J, et al., Rapid Method to Characterize Mutations in Transthyretin in Cerebrospinal Fluid from Familial Amyloidotic Polyneuropathy Patients by Use of Matrix-assisted Laser Desorption/Ionization Time-of-Flight Mass Spectrometry. Clinical Chem. 2000, 46(9):1293-1300.

Bramsen JB, et al., A Large-Scale Chemical Modification Screen Identifies Design Rules to Generate siRNAs with High Activity, High Stability and Low Toxicity, Nucleic Acids Res. 37(9):2867-2881 (2009).

Cendron L, et al., Amyloidogenic potential of transthyretin variants: insights from structural and computational analyses. J Biol Chem. Sep. 18, 2009;284(38):25832-41.

(56) References Cited

OTHER PUBLICATIONS

Chen et al. "Lipophilic siRNAs mediate efficient gene silencing in oligodendrocytes with direct CNS delivery", Journal of Controlled Release (2010).
Collingwood MA., et al., Chemical Modification Patterns Compatible with High Potency Dicer-Substrate Small Interfering RNAs. Oliginucleotides, 18:187-200 (2008).
Czauderna et al., "Structural variations and stabilising modifcations of synthetic siRNAs in mammalian cells", Nucleic Acids Research, 31(11)2705-2716, 2003.
DeLeavey GF, et al., Synergistic Effects Between Analogs of DNA and RNA Improve the Potency of siRNA-Mediated Gene Silencing, Nucleic Acids Res. 38(13):4547-4557 (2010).
Elbashir S, et al., Analysis of gene function in somatic mammalian cells using small interfering RNAs. Methods, 2002 pp. 199-213, vol. 26.
Elbashir S, et al., Duplexes of 21-nucleotide RNAs mediate RNA interference in mammalian cell culture. Nature, May 24, 2001, pp. 494-498, vol. 411.
Elbashir S, et al., Functional Anatomy of siRNAs for Mediating Efficient RNAi in Drosophila Melanogaster Embryo Lysate. The EMBO Journal, 2001, pp. 6877-6888, vol. 20, No. 23.
Elbashir S, et al., RNA Interference id Mediated by 21- and 22 Nucleotide RNAs. Genes & Development, 2001, pp. 188-200, vol. 15.
European Patent Office Communication pursuant to Article 94(3) EPC for European Patent Application No. 09 810 834.3, dated Feb. 15, 2012.
European Search Report from European Patent Application No. 12850255.6, dated May 11, 2015.
Examination Report for New Zealand Patent Application No. 592867, dated Jun. 14, 2011, 2 pages.
Extended European Search Report from EO 17184486.3 dated Jan. 29, 2018.
Fire A., at al., Potent and Specific Genetic Interference by Double Stranded RNA in Caenorhabditis elegans. Nature, Feb. 19, 1998, pp. 806-811, vol. 391.
Fire A., RNA-triggered Gene Silencing. Trends in Genetics, Sep. 1999, pp. 358-363, vol. 15, No. 9.
Gambari et a;. "Targeting microRNAs involved in human diseases: A novel approach for modification of gene expression and drug development", Biochemical Pharmacology 82 (2011) 1416-1429.
GenBank Accession No. NM_000371.2, *Homo sapiens* transthyretin (TTR), mRNA, Dec. 21, 2008.
GenBank Accession No. NM_000371.3, *Homo sapiens* transthyretin (TTR), mRNA, Sep. 23, 2012.
GenBank Accession No. NM_012681.1, *Rattus norvegicus* transthyretin (TTR), mRNA, Feb. 14, 2010.
GenBank Accession No. NM_013697.2, *Mus musculus* transthyretin (Ttr), mRNA, Apr. 5, 2007.
Hara R, et al., Impact of Liver Transplantation on Transthyretin-Related Ocular Amyloidosis in Japanese Patients. Arch Ophthalmol, Feb. 2010, pp. 206-210, vol. 128, No. 2.
Heyes J., et al., Cationic lipid saturation influences intracellular delivery of encapsulated nucleic acids. Journal of Controlled Release, 2005, pp. 276-287, vol. 107.
Hornung V, et al., "Sequence-specific potent induction of Ifn-a by short interfering RNA in plasmacytoid dendritic cells through TLR7". Nature Medicine, Mar. 2005, pp. 263-270, vol. 11, No. 3.
International Search Report and Written Opinion from PCT/US2016/044359 dated Nov. 7, 2016.
International Search Report for International Application No. PCT/US2012/065407 dated Apr. 22, 2013.
Judge A., et al., Confirming the RNAi-mediated mechanism of action of siRNA-based cancer therapeutics in mice. The Journal of Clinical Investigation, 2009 119(3): 661-673.
Kawasaki et al. "Synthesis, hybridization, and nuclease resistance properties of 2'-O-aminooxyethyl (2'-O-AOE) modified oligonucleotides", Tetrahedron Letters, 1999, 40, 661-664.
Kurosawa T., et al., Selective silencing of a mutant transthyretin allele by small interfering RNAs. Biochem. Biophys. Res. Commun., Nov. 25, 2005, vol. 337, No. 3, pp. 1012-1018.
Love K., et al., Lipid-like materials for low-dose, in vivo gene silencing. PNAS, Feb. 2, 2010, pp. 1864-69, vol. 107, No. 5.
Maeda S., Use of genetically altered mice to study the role of serum amyloid P component in amyloid deposition. Amyloid, 2003, vol. 10, Suppl 1, pp. 17-20.
Manoharan, "RNA interference and chemically modified small interfering RNAs", Current Opinion in Chemical Biology 2004, 8:570-579.
Morrissey D., et al., Potent and persistent in vivo anti-HBV activity of chemically modified siRNAs. Nature Biotechnology, Aug. 1, 2005, vol. 23, pp. 1002-1007.
Nakamura et al., "Targeted Conversion of the Transthyretin Gene in Vitro and in Vivo", Gene Therapy (2004) 11, 838-846.
PCT International Search Report and Written Opinion for International Patent Application No. PCT/US2009/061381, dated Jul. 26, 2010.
PCT International Search Report and Written Opinion for International Patent Application No. PCT/US2010/055311, dated Mar. 2, 2011, 12 pages.
PCT International Search Report and Written Opinion, PCT/US2011/030392, dated Jun. 27, 2011, 10 pages.
PCT Invitation to Pay Additional Fees and, Where Applicable, Protest Fee, PCT/US2009/061381, dated Apr. 27, 2010, 7 Pages.
Prakash TP, et al., Positional Effect of Chemical Modifications on Short INterference RNA Activity in Mammalian Cells. J. Med. Chem. 48:4247-4253 (2005).
Reynolds, et al., Rational siRNA design for Rna interference. Nature Biotechnology, vol. 22, No. 3, pp. 326-330, 2004.
Robbins M., et al., Stable expression of shRNAs in human CD34 progenitor cells can avoid induction of interferon responses to siRNAs in vitro. Nature Biotechnology, May 2006, pp. 566-571, vol. 24, No. 5.
Rose S., et al., Functional polarity is introduced by Dicer processing of short substrate RNAs. Nucleic Acids Research, 2005, pp. 4140-4156, vol. 33, No. 13.
Schweigert FJ, et al., Characterization of the microheterogeneity of traansthyretin in plasma and urine using SELDI-TOF-MS immunoassay. Proteome Sci. 2004, 2(1) article 5, pp. 1-6.
Sekijima Y., et al., Pathogensis of and Therapeutic Strategies to Ameliorate the Transthyretin Amyloidoses. Current Pharmaceutical Design, Jan. 1, 2008, pp. 3219-3230, vol. 14, No. 30.
Smith et al., "Knockdown of cortical transthyretin expression around implanted neural prosthetic devices using intraventricular siRNA injection in the brain", Journal of Neuroscience Methods, vol. 203(2), pp. 398-406 (2011).
Stein T., et al., Neutralization of transthyretin reverses the neuroprotective effects of secreted amyloid precursor protein (APP) in APP sw mice resulting in Tau phosphorylation and loss of Hippocampal neurons: support for the amyloid hypothesis. The Journal of Neuroscience, Sep. 1, 2004, vol. 24, No. 35, pp. 7707-7717.
Supplementary European Search Report for European Patent Application No. 10829034, dated Aug. 30, 2013, 9 pages.
The State Intellectual Property Office of the People's Republic of China, Notification of the First Office Action, Chinese Patent Application No. 200980141740.4, dated Jun. 5, 2012.
Trenchevska, et al., Mass spectrometric immunoassay for quantitative determination of transthyretin and its variants. Proteomics Aug. 9, 2011, 11(18):3633-3641; abstract p. 3633, para 1; p. 3634, para 5-6; p. 3635, para 1-4; p. 3636, para 2-3; p. 3637, para 2; p. 3639, para 3; Table 4; Figs 2-3.
Tuschl T., et al., Small Interfering RNAs: A Revolutionary Tool for the Analysis of Gene Function and Gene Therapy. Molecular Interventions, 2002, pp. 158-167, vol. 2, No. 3.
Tuschl T., et al., Targeted mRNA Degradation by Double-Stranded RNA In Vitro. Genes & Development, 1999, pp. 3191-3197, vol. 13.
Tuschl T., Expanding small RNA interference. Nature Biotechnology, May 2002, pp. 446-448, vol. 20.
Tuschl T., Functional genomics: RNA sets the standard. Nature, Hanuary 16, 2003, vol. 421, No. 6920, pp. 220-221.

(56) References Cited

OTHER PUBLICATIONS

Tuschl T., Mammalian RNA Interference. RNAi, A Guide to Gene Silencing, Chapter 13, G.J. Hannon (ed.), 2003, pp. 265-295.

Tuschl T., RNA Interference and Small Interfering RNAs. Chembiochem, 2001 pp. 39-245, vol. 2.

Ueda M, et al., A transgenic rat with the human ATTR V30M: A novel tool for analysis of ATTY metabolisms. Biochemical and Biophysical Research Communications, 2006, pp. 299-304, vol. 352.

Ueda M, et al., SELDI-TOF mass spectrometry evaluation of variant transthyretins for diagnosis and pathogenesis of familial amyloidotic polyneuropathy. Clin. Chem 2009; 55(6):1223-1227; abstract, Table 1.

Vickers T., et al., Efficient Reduction of Target RNAs by Small Interfering RNA and RNase H-dependent Antisense Agents. The Journal of Biological Chemistry, Feb. 28, 2003, pp. 7108-7118, vol. 278, No. 9.

Weil et al., Targeting the Kinesin Eg5 to Monitor siRNA Transfection in Mammalian Cells. Biotechniques, 2002, vol. 33, No. 6, pp. 1244-1248.

Wy Sah Dinah et al., "802: ALN-TTR, An RNAI Therapeutic for the Treatment of Transthyretin Amyloidosis", Nucleic Acid Therapeutics, vol. 21(5), pp. A55-A56 (Oct. 2011).

Zimmerman TS., et al., RNAi-mediated gene silencing in non-human primates. Nature, May 4, 2006, vol. 441, pp. 111-114.

Behlke, "Chemical Modification of siRNAs for In Vivo Use", Oligonucleotides 18:305-320 (2008).

Reynolds et al., "Rational siRNA design for RNA interference," Nature Biotechnology, vol. 22, pp. 326-330, 2004.

Conceição et al. "Early diagnosis of ATTR amyloidosis through targeted follow-up of identified carries of *TTR* gene mutations*," Amyloid, vol. 26, No. 1, pp. 3-9 (2019).

Coelho et al., "Safety and Efficacy of RNAi Therapy for Transthyretin Amyloidosis", N Engl J Med 2013; 369:819-829.

* cited by examiner

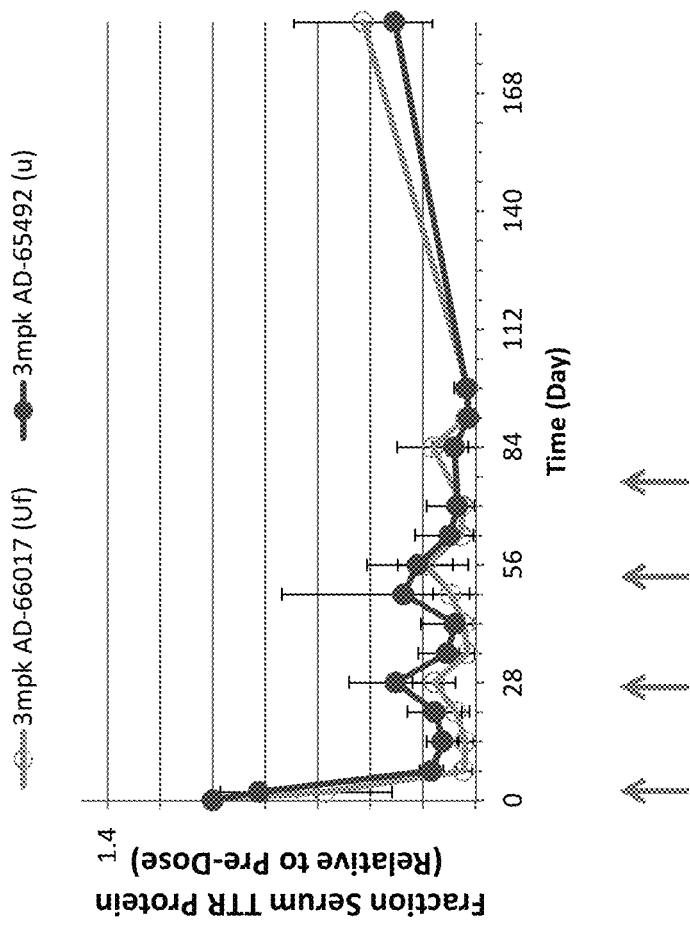

| Test Article | Group Number | n | Dose day | Dose level (mg/kg) | Dose Volume (mL/kg) | Re-dose days | Re-dose level (mg/kg) |
|---|---|---|---|---|---|---|---|
| AD-65492 | 1 | 3 | 1 | 0.3 | 2 | N/A | N/A |
| AD-65492 | 2 | 3 | 1 | 1 | 2 | N/A | N/A |
| AD-65492 | 3 | 3 | 1 | 3 | 2 | 29, 57, 85 | 3 |
| AD-66017 | 4 | 3 | 1 | 0.3 | 2 | N/A | N/A |
| AD-66017 | 5 | 3 | 1 | 1 | 2 | N/A | N/A |
| AD-66017 | 6 | 3 | 1 | 3 | 2 | 29, 57, 85 | 3 |
| AD-65492 | 7 | 3 | 1 | 1 | 2 | 29, 57, 85 | 1 |
| AD-66017 | 8 | 3 | 1 | 1 | 2 | 29, 57, 85 | 1 |

Figure 7

TRANSTHYRETIN (TTR) IRNA COMPOSITIONS AND METHODS OF USE THEREOF FOR TREATING OR PREVENTING TTR-ASSOCIATED DISEASES

RELATED APPLICATIONS

This application is a continuation of U.S. patent application Ser. No. 15/221,651, filed Jul. 28, 2016, now U.S. Pat. No. 10,208,307, issued on Feb. 19, 2019, which claims the benefit of priority to U.S. Provisional Patent Application No. 62/199,563, filed on Jul. 31, 2015, and to U.S. Provisional Patent Application No. 62/287,518, filed on Jan. 27, 2016. The entire contents of each of the foregoing applications are hereby incorporated herein by reference.

This application is related to U.S. Provisional Patent Application No. 61/881,257, filed Sep. 23, 2013, and International Application No. PCT/US2014/056923, filed Sep. 23, 2014, the entire contents of each of which are hereby incorporated herein by reference. In addition, this application is related to U.S. Provisional Application No. 61/561,710, filed on Nov. 18, 2011, International Application No. PCT/US2012/065601, filed on Nov. 16, 2012, U.S. Provisional Application No. 61/615,618, filed on Mar. 26, 2012, U.S. Provisional Application No. 61/680,098, filed on Aug. 6, 2012, U.S. application Ser. No. 14/358,972, filed on May 16, 2014, no U.S. Pat. No. 9,399,775, issued on Jul. 26, 2016, U.S. application Ser. No. 15/188,317, filed on Jun. 21, 2016, U.S. application Ser. No. 16/738,014, filed on Jan. 9, 2020, and International Application No. PCT/US2012/065691, filed Nov. 16, 2012, the entire contents of each of which are hereby incorporated herein by reference.

SEQUENCE LISTING

The instant application contains a Sequence Listing which has been submitted electronically in ASCII format and is hereby incorporated by reference in its entirety. Said ASCII copy, created on Dec. 18, 2018, is named 121301_03004_SeqListing.txt and is 68,327 bytes in size.

BACKGROUND OF THE INVENTION

Transthyretin (TTR) (also known as prealbumin) is found in serum and cerebrospinal fluid (CSF). TTR transports retinol-binding protein (RBP) and thyroxine (T4) and also acts as a carrier of retinol (vitamin A) through its association with RBP in the blood and the CSF. Transthyretin is named for its transport of thyroxine and retinol. TTR also functions as a protease and can cleave proteins including apoA-I (the major HDL apolipoprotein), amyloid β-peptide, and neuropeptide Y. See Liz, M. A. et al. (2010) *IUBMB Life*, 62(6):429-435.

TTR is a tetramer of four identical 127-amino acid subunits (monomers) that are rich in beta sheet structure. Each monomer has two 4-stranded beta sheets and the shape of a prolate ellipsoid. Antiparallel beta-sheet interactions link monomers into dimers. A short loop from each monomer forms the main dimer-dimer interaction. These two pairs of loops separate the opposed, convex beta-sheets of the dimers to form an internal channel.

The liver is the major site of TTR expression. Other significant sites of expression include the choroid plexus, retina (particularly the retinal pigment epithelium) and pancreas.

Transthyretin is one of at least 27 distinct types of proteins that is a precursor protein in the formation of amyloid fibrils. See Guan, J. et al. (Nov. 4, 2011) Current perspectives on cardiac amyloidosis, *Am J Physiol Heart Circ Physiol*, doi:10.1152/ajpheart.00815.2011. Extracellular deposition of amyloid fibrils in organs and tissues is the hallmark of amyloidosis. Amyloid fibrils are composed of misfolded protein aggregates, which may result from either excess production of or specific mutations in precursor proteins. The amyloidogenic potential of TTR may be related to its extensive beta sheet structure; X-ray crystallographic studies indicate that certain amyloidogenic mutations destabilize the tetrameric structure of the protein. See, e.g., Saraiva M. J. M. (2002) *Expert Reviews in Molecular Medicine*, 4(12): 1-11.

Amyloidosis is a general term for the group of amyloid diseases that are characterized by amyloid deposits. Amyloid diseases are classified based on their precursor protein; for example, the name starts with "A" for amyloid and is followed by an abbreviation of the precursor protein, e.g., ATTR for amyloidogenic transthyretin. Ibid.

There are numerous TTR-associated diseases, most of which are amyloid diseases. Normal-sequence TTR is associated with cardiac amyloidosis in people who are elderly and is termed senile systemic amyloidosis (SSA) (also called senile cardiac amyloidosis (SCA) or cardiac amyloidosis). SSA often is accompanied by microscopic deposits in many other organs. TTR amyloidosis manifests in various forms. When the peripheral nervous system is affected more prominently, the disease is termed familial amyloidotic polyneuropathy (FAP). When the heart is primarily involved but the nervous system is not, the disease is called familial amyloidotic cardiomyopathy (FAC). A third major type of TTR amyloidosis is leptomeningeal amyloidosis, also known as leptomeningeal or meningocerebrovascular amyloidosis, central nervous system (CNS) amyloidosis, or amyloidosis VII form. Mutations in TTR may also cause amyloidotic vitreous opacities, carpal tunnel syndrome, and euthyroid hyperthyroxinemia, which is a non-amyloidotic disease thought to be secondary to an increased association of thyroxine with TTR due to a mutant TTR molecule with increased affinity for thyroxine. See, e.g., Moses et al. (1982) *J. Clin. Invest.*, 86, 2025-2033.

Abnormal amyloidogenic proteins may be either inherited or acquired through somatic mutations. Guan, J. et al. (Nov. 4, 2011) Current perspectives on cardiac amyloidosis, *Am J Physiol Heart Circ Physiol*, doi:10.1152/ajpheart.00815.2011. Transthyretin associated ATTR is the most frequent form of hereditary systemic amyloidosis. Lobato, L. (2003) *J. Nephrol.*, 16:438-442. TTR mutations accelerate the process of TTR amyloid formation and are the most important risk factor for the development of ATTR. More than 85 amyloidogenic TTR variants are known to cause systemic familial amyloidosis. TTR mutations usually give rise to systemic amyloid deposition, with particular involvement of the peripheral nervous system, although some mutations are associated with cardiomyopathy or vitreous opacities. Ibid.

The V30M mutation is the most prevalent TTR mutation. See, e.g., Lobato, L. (2003) *J Nephrol*, 16:438-442. The V122I mutation is carried by 3.9% of the African American population and is the most common cause of FAC. Jacobson, D. R. et al. (1997) *N. Engl. J. Med.* 336 (7): 466-73. It is estimated that SSA affects more than 25% of the population over age 80. Westermark, P. et al. (1990) *Proc. Natl. Acad. Sci. U.S.A.* 87 (7): 2843-5.

Accordingly, there is a need in the art for effective treatments for TTR-associated diseases.

SUMMARY OF THE INVENTION

The present invention provides RNAi agents, e.g., double stranded RNAi agents, and compositions targeting the Transthyretin (TTR) gene. The present invention also provides methods of inhibiting expression of TTR and methods of treating or preventing a TTR-associated disease in a subject using the RNAi agents, e.g., double stranded RNAi agents, of the invention. The present invention is based, at least in part, on the discovery that RNAi agents in which substantially all of the nucleotides on the sense strand and substantially all of the nucleotides of the antisense strand are modified nucleotides and that comprise no more than 8 2'-fluoro modifications on the sense strand, no more than 6 2'-fluoro modifications on the antisense strand, two phosphorothioate linkages at the 5'-end of the sense strand, two phosphorothioate linkages at the 5'-end of the antisense strand, and a ligand, e.g., a GalNAc₃ ligand, are shown herein to be effective in silencing the activity of the TTR gene. These agents show surprisingly enhanced TTR gene silencing activity. Without intending to be limited by theory, it is believed that a combination or sub-combination of the foregoing modifications and the specific target sites in these RNAi agents confer to the RNAi agents of the invention improved efficacy, stability, potency, and durability.

Accordingly, in one aspect, the present invention provides double stranded ribonucleic acid (RNAi) agents for inhibiting expression of transthyretin (TTR) in a cell, wherein the RNAi agent comprises a sense strand complementary to an antisense strand, wherein the antisense strand comprises a region complementary to SEQ ID NO:2 (5'-UGGGAUUU-CAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one embodiment, and wherein the double stranded RNAi agent is represented by formula (IIIe):

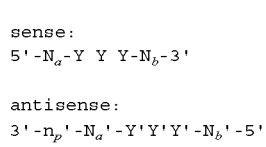

wherein:

$n_p'$ is a 2 nucleotide overhang and each nucleotide within $n_p'$ is linked to a neighboring nucleotide via a phosphorothioate linkage;

each $N_a$, $N_b$, $N_a'$ and $N_b'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides.

In one embodiment, the YYY motif occurs at or near the cleavage site of the sense strand. In one embodiment, the Y'Y'Y' motif occurs at the 11, 12 and 13 positions of the antisense strand from the 5'-end.

In one embodiment, the Y nucleotides contain a 2'-fluoro modification.

In one embodiment, the Y' nucleotides contain a 2'-O-methyl modification.

The double stranded region may be 15-30 nucleotide pairs in length, 17-23 nucleotide pairs in length, 17-25 nucleotide pairs in length, 23-27 nucleotide pairs in length, 19-21 nucleotide pairs in length, or 21-23 nucleotide pairs in length.

Each strand of the double stranded RNAi agent may have 15-30 nucleotides or 19-30 nucleotides.

In one embodiment, the modifications on the nucleotides are selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic, and combinations thereof.

In one embodiment, the modifications on the nucleotides are 2'-O-methyl or 2'-fluoro modifications.

The sense strand may comprise no more than 7 2'-fluoro modifications, no more than 6 2'-fluoro modifications, no more than 5 2'-fluoro modification, no more than 4 2'-fluoro modifications, no more than 3 2'-fluoro modifications, or no more than 2 2'-fluoro modifications.

The antisense strand may comprise no more than 5 2'-fluoro modifications, no more than 4 2'-fluoro modifications, no more than 3 2'-fluoro modifications, or no more than 2 2'-fluoro modifications.

In one embodiment, the double stranded RNAi agent further comprises a 5'-phosphate or a 5'-phosphate mimic at the 5' nucleotide of the antisense strand. In another embodiment, the double stranded RNAi agent further comprises a 5'-phosphate mimic at the 5' nucleotide of the antisense strand.

In one embodiment, the 5'-phosphate mimic is a 5'-vinyl phosphate (5'-VP).

In one embodiment, the ligand is one or more GalNAc derivatives attached through a bivalent or trivalent branched linker. In another embodiment, the ligand is

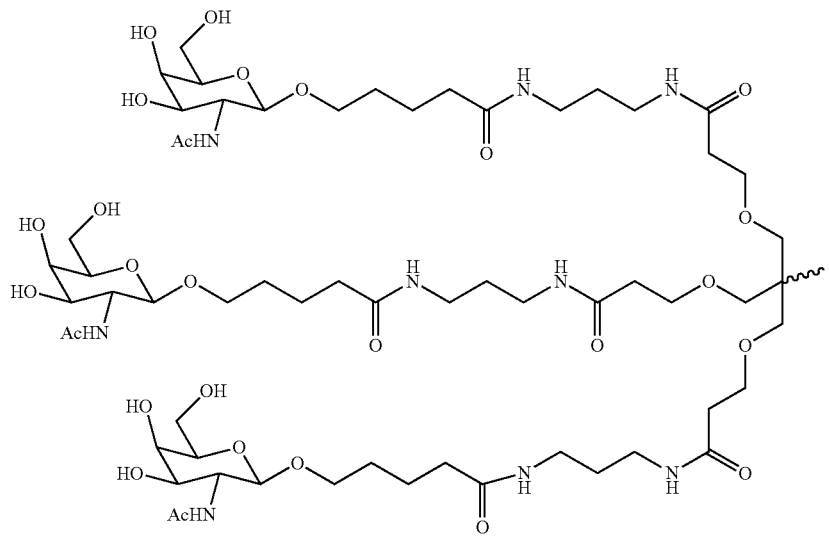

Formula II

In one embodiment, the ligand is attached to the 3' end of the sense strand.

In one embodiment, the double stranded RNAi agent is conjugated to the ligand as shown in the following schematic

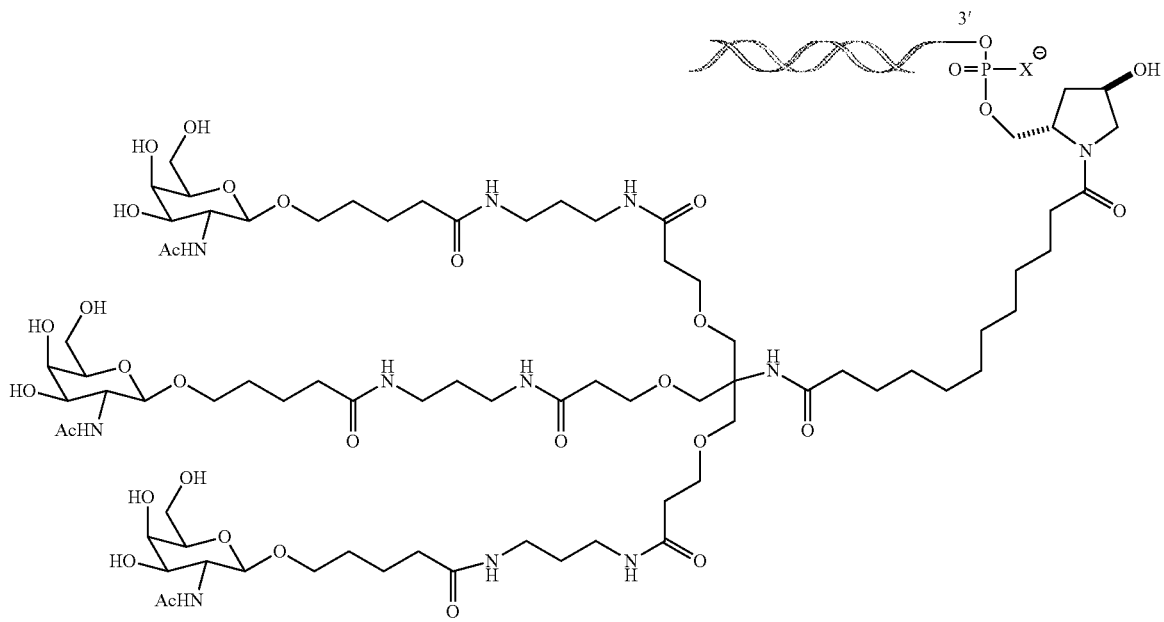

wherein X is O or S.

In one embodiment, the antisense strands comprise a nucleotide sequence selected from the group consisting of 5'-usCfsuugguuacaugAfaaucccasusc-3' (SEQ ID NO: 6), 5'-usCfsuugGfuuAfcaugAfaAfucccasusc-3' (SEQ ID NO:7), 5'-UfsCfsuugGfuuAfcaugAfaAfucccasusc-3' (SEQ ID NO: 8), and 5'-VPusCfsuugGfuuAfcaugAfaAfuccca-susc-3' (SEQ ID NO: 9), wherein a, c, g, and u are 2'-O-methyl (2'-OMe) A, C, G, or U; Af, Cf, Gf, and Uf are 2'-fluoro A, C, G, or U; and s is a phosphorothioate linkage; and VP is a 5'-phosphate mimic.

In one embodiment, the sense and antisense strands comprise nucleotide sequences selected from the group consisting of 5'-usgsggauUfuCfAfUfguaaccaaga-3' (SEQ ID NO: 10) and 5'-usCfsuugguuacaugAfaaucccasusc-3' (SEQ ID NO: 6); 5'-usgsggauUfuCfAfUfguaaccaaga-3' (SEQ ID NO: 10) and 5'-usCfsuugGfuuAfcaugAfaAfucccasusc-3' (SEQ ID NO: 7); 5'-usgsggauUfuCfAfUfguaaccaaga-3' (SEQ ID NO: 10) and 5'-UfsCfsuugGfuuAfcaugAfaAfuc-ccasusc-3' (SEQ ID NO: 8); and 5'-usgsggauUfuCfAfUf-guaaccaaga-3' (SEQ ID NO: 10) and 5'-VPusCfsuug-GfuuAfcaugAfaAfucccasusc-3' (SEQ ID NO: 9), wherein a, c, g, and u are 2'-O-methyl (2'-OMe) A, C, G, or U; Af, Cf, Gf, and Uf are 2'-fluoro A, C, G, or U; and s is a phosphorothioate linkage; and VP is a 5'-phosphate mimic. In another embodiment, the sense and antisense strands comprise the nucleotide sequences 5'-usgsggauUfuCfAfUfguaaccaaga-3' (SEQ ID NO: 10) and 5'-usCfsuugGfuuAf-caugAfaAfucccasusc-3' (SEQ ID NO: 7), wherein a, c, g, and u are 2'-O-methyl (2'-OMe) A, C, G, or U; Af, Cf, Gf, and Uf are 2'-fluoro A, C, G, or U; and s is a phosphorothioate linkage. In yet another embodiment, the RNAi agent is selected from the group of any one of the RNAi agents listed in any one of Tables 1 and 3. In yet another embodiment, the RNAi agent is AD-65492.

In one aspect, the present invention provides double stranded ribonucleic acid (RNAi) agents for inhibiting expression of transthyretin (TTR) in a cell, wherein the RNAi agent comprises a sense strand complementary to an antisense strand, wherein the antisense strand comprises a region fully complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand, wherein the ligand is one or more GalNAc derivatives attached through a bivalent or trivalent branched linker.

In one embodiment, the double stranded RNAi agent is represented by formula (IIIe):

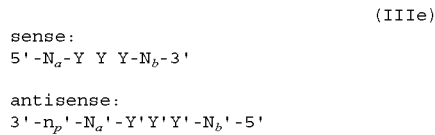

wherein:

$n_p'$ is a 2 nucleotide overhang and each nucleotide within $n_p'$ is linked to a neighboring nucleotide via a phosphorothioate linkage;

each $N_a$, $N_b$, $N_a'$ and $N_b'$ independently represents an oligonucleotide sequence comprising 8-10 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications.

The present invention also provides cells containing the double stranded RNAi agents of the invention, cells comprising the vectors of the invention, and pharmaceutical compositions comprising the double stranded RNAi agents of the invention or the vectors of the invention.

In one embodiment, the double stranded RNAi agent is administered in an unbuffered solution, e.g., saline or water.

In another embodiment, the double stranded RNAi agent is administered with a buffer solution. In one embodiment, the buffer solution comprises acetate, citrate, prolamine, carbonate, or phosphate or any combination thereof. In another embodiment, the buffer solution is phosphate buffered saline (PBS).

In another aspect, the present invention provides methods of inhibiting transthyretin (TTR) expression in a cell. The methods include (a) contacting the cell with the double stranded RNAi agents of the invention, the vectors of the invention, or the pharmaceutical compositions of the invention; and (b) maintaining the cell produced in step (a) for a time sufficient to obtain degradation of the mRNA transcript of a TTR gene, thereby inhibiting expression of the TTR gene in the cell.

In one embodiment, the cell is within a subject.

In one embodiment, the subject is a human.

In one embodiment, the subject suffers from TTR-associated disease.

In one embodiment, the TTR expression is inhibited by at least about 10%, about 15%, about 20%, about 25%, about 30%, about 40%, about 50%, about 60%, about 70%, about 80%, about 90%, about 95%, about 98% or about 100%.

In yet another aspect, the present invention provides methods of treating a subject having a transthyretin (TTR)-associated disorder, by administering to the subject a therapeutically effective amount of the double stranded RNAi agents of the invention, or the vectors of the invention, or the pharmaceutical compositions of the invention, thereby treating the subject.

In yet another aspect, the present invention provides methods of prophylactically treating a subject at risk of developing a transthyretin (TTR)-associated disorder, by administering to the subject a prophylactically effective amount of the double stranded RNAi agents of the invention, or the vectors of the invention, or the pharmaceutical compositions of the invention, thereby prophylactically treating the subject.

In a further aspect, the present invention provides methods of treating a subject having a transthyretin (TTR)-associated disorder. The methods include administering to the subject a therapeutically effective amount of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In a further aspect, the present invention provides methods of prophylactically treating a subject at risk of developing a transthyretin (TTR)-associated disorder. The methods include administering to the subject a prophylactically effective amount of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of reducing, slowing, or arresting a Neuropathy Impairment Score (NIS) or a modified NIS (mNIS+7) in a subject having a transthyretin (TTR)-associated disorder. The methods include administering to the subject a therapeutically effective amount of the double stranded RNAi agents of the invention, or the vectors of the invention, or the pharmaceutical compositions of the invention, thereby reducing, slowing, or arresting a Neuropathy Impairment Score (NIS) or a modified NIS (mNIS+7) in the subject.

In a further aspect, the present invention provides methods of reducing, slowing, or arresting a Neuropathy Impairment Score (NIS) or a modified NIS (mNIS+7) a subject having a transthyretin (TTR)-associated disorder. The methods include administering to the subject a therapeutically effective amount of a double stranded RNAi agent, wherein the double stranded RNAi agent comprises a sense strand complementary to an antisense strand, wherein said antisense strand comprises a region complementary to SEQ ID NO:2, wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of increasing a 6-minute walk test (6MWT) in a subject having a transthyretin (TTR)-associated disorder. The methods include administering to the subject a therapeutically effective amount of the the double stranded RNAi agents of the invention, or the vectors of the invention, or the pharmaceutical compositions of the invention, thereby increasing a 6-minute walk test (6MWT) in the subject.

In a further aspect, the present invention provides methods of increasing a 6-minute walk test (6MWT) in a subject having a transthyretin (TTR)-associated disorder. The methods include administering to the subject a therapeutically effective amount of a double stranded RNAi agent, wherein the double stranded RNAi agent comprises a sense strand complementary to an antisense strand, wherein said antisense strand comprises a region complementary to SEQ ID NO:2, wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one embodiment, the double stranded RNAi agent is represented by formula (IIIe):

```
                                              (IIIe)
sense:
5'-Na-Y Y Y-Nb-3' antisense:
3'-np'-Na'-Y'Y'Y'-Nb'-5'
``` wherein:

$n_p'$ is a 2 nucleotide overhang and each nucleotide within $n_p'$ is linked to a neighboring nucleotide via a phosphorothioate linkage;

each $N_a$, $N_b$, $N_b$ and $N_b'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides.

In one embodiment, the subject is a human.

In one embodiment, the subject is a subject suffering from a TTR-associated disease. In another embodiment, the subject is a subject at risk for developing a TTR-associated disease. In one embodiment, the subject at risk of developing a TTR-associated disease carries a TTR gene mutation that is associated with the development of a TTR associated disease, or a subject with a family history of TTR-associated disease, or a subject who has signs or symptoms suggesting the development of TTR amyloidosis.

In one embodiment, the TTR-associated disease is selected from the group consisting of senile systemic amyloidosis (SSA), systemic familial amyloidosis, familial amyloidotic polyneuropathy (FAP), familial amyloidotic cardiomyopathy (FAC), leptomeningeal/Central Nervous System (CNS) amyloidosis, and hyperthyroxinemia.

In one embodiment, the subject has a TTR-associated amyloidosis and the method reduces an amyloid TTR deposit in the subject.

In one embodiment, the double stranded RNAi agent is administered to the subject by an administration means selected from the group consisting of subcutaneous, intravenous, intramuscular, intrabronchial, intrapleural, intraperitoneal, intraarterial, lymphatic, cerebrospinal, and any combinations thereof. In another embodiment, the double stranded RNAi agent is administered to the subject via subcutaneous, intramuscular or intravenous administration. In yet another embodiment, the double stranded RNAi agent is administered to the subject via subcutaneous administration.

In one embodiment, the methods further comprise assessing the level of TTR mRNA expression or TTR protein expression in a sample derived from the subject.

In one embodiment, administering the double stranded RNAi agent does not result in an inflammatory response in the subject as assessed based on the level of a cytokine or chemokine selected from the group consisting of G-CSF, IFN-γ, IL-10, IL-12 (p70), IL1β, IL-1ra, IL-6, IL-8, IP-10, MCP-1, MIP-1α, MIP-1β, TNFα, and any combinations thereof, in a sample from the subject.

In one aspect, the present invention provides methods of treating a subject having a transthyretin (TTR)-associated disorder. The methods include administering to the subject a fixed dose of about 12.5 mg to about 200 mg (e.g., about 12.5 mg, about 25 mg, about 50 mg, about 75 mg, about 100 mg, about 125 mg, about 150 mg, about 175 mg, or about 200 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In another aspect, the present invention provides methods of prophylactically treating a subject at risk of developing a transthyretin (TTR)-associated disorder. The methods include administering to the subject a fixed dose of about 12.5 mg to about 200 mg (e.g., about 12.5 mg, about 25 mg, about 50 mg, about 75 mg, about 100 mg, about 125 mg, about 150 mg, about 175 mg, or about 200 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of treating a subject having a transthyretin (TTR)-associated disorder. The methods include administering to the subject a dose of about 0.15 mg/kg to about 2.5 mg/kg (e.g., about 0.15 mg/kg, about 0.3 mg/kg, about 0.6 mg/kg, about 1 mg/kg, about 1.25 mg/kg, about 2 mg/kg, about 2.5 mg/kg, or about 3 mg/kg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of prophylactically treating a subject at risk of developing a transthyretin (TTR)-associated disorder. The methods include administering to the subject a dose of about 0.15 mg/kg to about 2.5 mg/kg (e.g., about 0.15 mg/kg, about 0.3 mg/kg, about 0.6 mg/kg, about 1 mg/kg, about 1.25 mg/kg, about 2 mg/kg, about 2.5 mg/kg, or about 3 mg/kg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In another aspect, the present invention provides methods of reducing, slowing, or arresting a Neuropathy Impairment Score (NIS) or a modified NIS (mNIS+7) in a subject having a transthyretin (TTR)-associated disorder. The methods include administering to the subject a dose of about 0.15 mg/kg to about 2.5 mg/kg (e.g., about 0.15 mg/kg, about 0.3 mg/kg, about 0.6 mg/kg, about 1 mg/kg, about 1.25 mg/kg, about 2 mg/kg, about 2.5 mg/kg, or about 3 mg/kg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In yet another aspect, the present invention provides methods of increasing a 6-minute walk test (6MWT) in a subject having a transthyretin (TTR)-associated disorder. The methods include administering to the subject a dose of about 0.15 mg/kg to about 2.5 mg/kg (e.g., about 0.15 mg/kg, about 0.3 mg/kg, about 0.6 mg/kg, about 1 mg/kg, about 1.25 mg/kg, about 2 mg/kg, about 2.5 mg/kg, or about 3 mg/kg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of treating a subject having a transthyretin (TTR)-associated disorder. The methods include administering to the subject a fixed dose of about 10 mg to about 600 mg, about 25 mg to about 500 mg, about 50 mg to about 500 mg, or about 80 mg to about 500 mg, about 25 mg to about 300 mg, about 50 mg to about 300 mg, or about 80 mg to about 300 mg (e.g., about 10, about 20, about 30, about 40, about 50, about 60, about 70, about 75, about 80, about 90, about 100, about 110, about 120, about 125, about 130, about 140, about 150, about 160, about 170, about 175, about 180, about 190, about 200, about 210, about 220, about 225, about 230, about 240, about 250, about 260, about 270, about 275, about 280, about 290, about 300, about 310, about 320, about 325, about 330, about 340, about 350, about 360, about 370, about 375, about 380, about 390, about 400, about 410, about 420, about 425, about 430, about 440, about 450, about 460, about 470, about 475, about 480, about 490, about 500, about 510, about 520, about 525, about 530, about 540, about 550, about 560, about 570, about 575, about 580, about 590, or about 600 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAU-GUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one aspect, the present invention provides methods of prophylactically treating a subject at risk of developing a transthyretin (TTR)-associated disorder. The methods include administering to the subject a fixed dose of about 10 mg to about 600 mg, about 25 mg to about 500 mg, about 50 mg to about 500 mg, or about 80 mg to about 500 mg, about 25 mg to about 300 mg, about 50 mg to about 300 mg, or about 80 mg to about 300 mg (e.g., about 10, about 20, about 30, about 40, about 50, about 60, about 70, about 75, about 80, about 90, about 100, about 110, about 120, about 125, about 130, about 140, about 150, about 160, about 170, about 175, about 180, about 190, about 200, about 210, about 220, about 225, about 230, about 240, about 250, about 260, about 270, about 275, about 280, about 290, about 300, about 310, about 320, about 325, about 330, about 340, about 350, about 360, about 370, about 375, about 380, about 390, about 400, about 410, about 420, about 425, about 430, about 440, about 450, about 460, about 470, about 475, about 480, about 490, about 500, about 510, about 520, about 525, about 530, about 540, about 550, about 560, about 570, about 575, about 580, about 590, or about 600 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAUGUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In another aspect, the present invention provides methods of reducing, slowing, or arresting a Neuropathy Impairment Score (NIS) or a modified NIS (mNIS+7) in a subject having a transthyretin (TTR)-associated disorder. The methods include administering to the subject a fixed dose of about 10 mg to about 600 mg, about 25 mg to about 500 mg, about 50 mg to about 500 mg, or about 80 mg to about 500 mg, about 25 mg to about 300 mg, about 50 mg to about 300 mg, or about 80 mg to about 300 mg (e.g., about 10, about 20, about 30, about 40, about 50, about 60, about 70, about 75, about 80, about 90, about 100, about 110, about 120, about 125, about 130, about 140, about 150, about 160, about 170, about 175, about 180, about 190, about 200, about 210, about 220, about 225, about 230, about 240, about 250 mg, about 260, about 270, about 275, about 280, about 290, about 300, about 310, about 320, about 325, about 330, about 340, about 350, about 360, about 370, about 375, about 380, about 390, about 400, about 410, about 420, about 425, about 430, about 440, about 450 mg, about 460, about 470, about 475, about 480, about 490, about 500, about 510, about 520, about 525, about 530, about 540, about 550, about 560, about 570, about 575, about 580, about 590, or about 600 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAU-GUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In yet another aspect, the present invention provides methods of increasing a 6-minute walk test (6MWT) in a subject having a transthyretin (TTR)-associated disorder. The methods include administering to the subject a fixed dose of about 10 mg to about 600 mg, about 25 mg to about 500 mg, about 50 mg to about 500 mg, or about 80 mg to about 500 mg, about 25 mg to about 300 mg, about 50 mg to about 300 mg, or about 80 mg to about 300 mg (e.g., about 10, about 20, about 30, about 40, about 50, about 60, about 70, about 75, about 80, about 90, about 100, about 110, about 120, about 125, about 130, about 140, about 150, about 160, about 170, about 175, about 180, about 190, about 200, about 210, about 220, about 225, about 230, about 240, about 250 mg, about 260, about 270, about 275, about 280, about 290, about 300, about 310, about 320, about 325, about 330, about 340, about 350, about 360, about 370, about 375, about 380, about 390, about 400, about 410, about 420, about 425, about 430, about 440, about 450 mg, about 460, about 470, about 475, about 480, about 490, about 500, about 510, about 520, about 525, about 530, about 540, about 550, about 560, about 570, about 575, about 580, about 590, or about 600 mg) of a double stranded RNAi agent, wherein the double stranded RNAi agent comprises a sense strand complementary to an antisense strand, wherein the antisense strand comprises a region complementary to SEQ ID NO:2 (5'-UGGGAUUUCAU-GUAACCAAGA-3'), wherein each strand is about 14 to about 30 nucleotides in length, wherein substantially all of the nucleotides of the sense strand and substantially all of the nucleotides of the antisense strand are modified nucleotides, wherein the sense strand comprises no more than 8 2'-fluoro modifications; wherein the antisense strand comprises no more than 6 2'-fluoro modifications; wherein the sense strand and the antisense strand each independently comprise two phosphorothioate linkages at the 5'-terminus; and wherein the sense strand is conjugated to at least one ligand.

In one embodiment, the double stranded RNAi agent is represented by formula (IIIe):

(IIIe)

sense:
5'-$N_a$-Y Y Y-$N_b$-3' antisense:
3'-$n_p'$-$N_a'$-Y'Y'Y'-$N_b'$-5' wherein:

$n_p'$ is a 2 nucleotide overhang and each nucleotide within $n_p'$ is linked to a neighboring nucleotide via a phosphorothioate linkage;

each $N_a$, $N_b$, $N_b$ and $N_b'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides.

In one embodiment, the antisense strand comprises a nucleotide sequence selected from the group consisting of 5'-usCfsuugguuacaugAfaaucccasusc-3' (SEQ ID NO: 6), 5'-usCfsuugGfuuAfcaugAfaAfucccasusc-3'(SEQ ID NO: 7), 5'-UfsCfsuugGfuuAfcaugAfaAfucccasusc-3' (SEQ ID NO: 8), and 5'-VPusCfsuugGfuuAfcaugAfaAfucccasusc-3' (SEQ ID NO: 9), wherein a, c, g, and u are 2'-O-methyl (2'-OMe) A, C, G, or U; Af, Cf, Gf, and Uf are 2'-fluoro A, C, G, or U; s is a phosphorothioate linkage; and VP is a 5'-phosphate mimic.

In one embodiment, the sense and antisense strands comprise nucleotide sequences selected from the group consisting of 5'-usgsggauUfuCfAfUfguaaccaaga-3' (SEQ ID NO: 10) and 5'-usCfsuugguuacaugAfaaucccasusc-3' (SEQ ID NO: 6); 5'-usgsggauUfuCfAfUfguaaccaaga-3' (SEQ ID NO: 10) and 5'-usCfsuugGfuuAfcaugAfaAfucccasusc-3' (SEQ ID NO: 7); 5'-usgsggauUfuCfAfUfguaaccaaga-3' (SEQ ID NO: 10) and 5'-UfsCfsuugGfuuAfcaugAfaAfucccasusc-3'(SEQ ID NO: 8); and 5'-usgsggauUfuCfAfUfguaaccaaga-3' (SEQ ID NO: 10) and 5'-VPusCfsuugGfuuAfcaugAfaAfucccasusc-3' (SEQ ID NO: 9), wherein a, c, g, and u are 2'-O-methyl (2'-OMe) A, C, G, or U; Af, Cf, Gf, and Uf are 2'-fluoro A, C, G, or U; and s is a phosphorothioate linkage; and VP is a 5'-phosphate mimic.

In one embodiment, the sense and antisense strands comprise the nucleotide sequences

```
                                    (SEQ ID NO: 10)
5'-usgsggauUfuCfAfUfguaaccaaga-3'
and
                                    (SEQ ID NO: 7)
5'-usCfsuugGfuuAfcaugAfaAfucccasusc-3',
``` wherein a, c, g, and u are 2'-O-methyl (2'-OMe) A, C, G, or U; Af, Cf, Gf, and Uf are 2'-fluoro A, C, G, or U; and s is a phosphorothioate linkage.

The fixed dose of the double stranded RNAi agent may be administered to the subject once about every 4 weeks, every 5 weeks, every six weeks, every eight weeks or quarterly.

The dose of the double stranded RNAi agent may be administered to the subject once about every 4 weeks, every 5 weeks, every six weeks, every eight weeks or quarterly.

In one embodiment, the double stranded RNAi agent is administered to the subject about once every quarter.

In one embodiment, the double stranded RNAi agent is chronically administered to the subject.

In one embodiment, the subject is a human.

In one embodiment, the subject is a subject suffering from a TTR-associated disease. In another embodiment, the subject is a subject at risk for developing a TTR-associated disease. In one embodiment, the subject at risk of developing a TTR-associated disease carries a TTR gene mutation that is associated with the development of a TTR associated disease, or a subject with a family history of TTR-associated disease, or a subject who has signs or symptoms suggesting the development of TTR amyloidosis.

In one embodiment, the TTR-associated disease is selected from the group consisting of senile systemic amyloidosis (SSA), systemic familial amyloidosis, familial amyloidotic polyneuropathy (FAP), familial amyloidotic cardiomyopathy (FAC), leptomeningeal/Central Nervous System (CNS) amyloidosis, and hyperthyroxinemia.

In one embodiment, the subject has a TTR-associated amyloidosis and the method reduces an amyloid TTR deposit in the subject.

In one embodiment, the double stranded RNAi agent is administered to the subject by an administration means selected from the group consisting of subcutaneous, intravenous, intramuscular, intrabronchial, intrapleural, intraperitoneal, intraarterial, lymphatic, cerebrospinal, and any combinations thereof. In another embodiment, the double stranded RNAi agent is administered to the subject via subcutaneous, intramuscular or intravenous administration. In yet another embodiment, the double stranded RNAi agent is administered to the subject via subcutaneous administration, e.g., via self administration, e.g., via a pre-filled syringe or auto-injector syringe.

In one embodiment, the methods further comprise assessing the level of TTR mRNA expression or TTR protein expression in a sample derived from the subject.

In one embodiment, administering the double stranded RNAi agent does not result in an inflammatory response in the subject as assessed based on the level of a cytokine or chemokine selected from the group consisting of G-CSF, IFN-γ, IL-10, IL-12 (p70), IL1β, IL-1ra, IL-6, IL-8, IP-10, MCP-1, MIP-1α, MIP-1β, TNFα, and any combinations thereof, in a sample from the subject.

In one embodiment, the agent suitable for use in the methods of the invention is AD-65492. AD-65492 may be chronically administered to the subject every 4 weeks, every 5 weeks, or every six weeks, or every quarter.

In one aspect, the present invention provides double stranded ribonucleic acid (RNAi) agents for use in inhibiting expression of transthyretin (TTR) in a cell. The agents include a sense strand complementary to an antisense strand, wherein the sense and antisense strands comprise nucleotide sequences selected from the group consisting of any of the nucleotide sequences in Table 5.

In another aspect, the present invention provides double stranded ribonucleic acid (RNAi) agents for use in inhibiting expression of transthyretin (TTR) in a cell. The agents include a sense strand complementary to an antisense strand, the antisense strand comprising a region of complementarity which comprises at least 15 contiguous nucleotides differing no more than 3 nucleotides from any one of the antisense sequences in Table 6, wherein substantially all of the nucleotides of the sense strand and substantially all of the nucleotides of the antisense strand are modified nucleotides; and wherein the sense strand is conjugated to at least one ligand.

The sense and antisense strand may comprise nucleotide sequences selected from the group consisting of any of the nucleotide sequences in Table 6 or Table 7.

In one aspect the present invention provides double stranded ribonucleic acid (RNAi) agents for use in inhibiting expression of transthyretin (TTR) in a cell, wherein the RNAi agents comprise a sense strand complementary to an antisense strand, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7), wherein a, c, g, and u are 2'-O- methyl (2'-OMe) A, C, G, or U; Af, Cf, Gf, and Uf are 2'-fluoro A, C, G, or U; and s is a phosphorothioate linkage.

In another aspect, the present invention provides methods of treating a subject suffering from a TTR-associated disease. The methods include administering to the subject a dose of about 50 mg to about 300 mg of a double stranded RNAi agent, wherein the RNAi agent comprises a sense strand complementary to an antisense strand, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7), wherein a, c, g, and u are 2'-O-methyl (2'-OMe) A, C, G, or U; Af, Cf, Gf, and Uf are 2'-fluoro A, C, G, or U; and s is a phosphorothioate linkage, thereby treating the subject suffering from a TTR-associated disease.

In yet another aspect, the present invention provides methods of prophylactically treating a subject at risk for developing a TTR-associated disease. The methods include administering to the subject a dose of about 50 mg to about 300 mg of a double stranded RNAi agent, wherein the RNAi agent comprises a sense strand complementary to an antisense strand, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7), wherein a, c, g, and u are 2'-O-methyl (2'-OMe) A, C, G, or U; Af, Cf, Gf, and Uf are 2'-fluoro A, C, G, or U; and s is a phosphorothioate linkage, thereby prophylactically treating the subject at risk for developing a TTR-associated disease.

In one aspect, the present invention provides methods of reducing, slowing, or arresting a Neuropathy Impairment Score (NIS) or a modified NIS (mNIS+7) in a subject suffering from a TTR-associated disease or at risk for developing a TTR-associated disease. The methods include administering to the subject a dose of about 50 mg to about 300 mg of a double stranded RNAi agent, wherein the RNAi agent comprises a sense strand complementary to an antisense strand, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7), wherein a, c, g, and u are 2'-O-methyl (2'-OMe) A, C, G, or U; Af, Cf, Gf, and Uf are 2'-fluoro A, C, G, or U; and s is a phosphorothioate linkage, thereby reducing, slowing, or arresting a Neuropathy Impairment Score (NIS) or a modified NIS (mNIS+7) in the subject.

In another aspect, the present invention provides methods of increasing a 6-minute walk test (6MWT) in a subject suffering from a TTR-associated disease or at risk for developing a TTR-associated disease. The methods include administering to the subject a dose of about 50 mg to about 300 mg of of a double stranded RNAi agent, wherein the RNAi agent comprises a sense strand complementary to an antisense strand, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7), wherein a, c, g, and u are 2'-O-methyl (2'-OMe) A, C, G, or U; Af, Cf, Gf, and Uf are 2'-fluoro A, C, G, or U; and s is a phosphorothioate linkage, thereby increasing a 6-minute walk test (6MWT) in a subject suffering from a TTR-associated disease or at risk for developing a TTR-associated disease.

The present invention is further illustrated by the following detailed description and drawings.

BRIEF DESCRIPTION OF THE DRAWINGS

FIG. 6C is graph depicting TTR protein suppression in transgenic mice that express hTTR V30M following subcutaneous administration of a monthly 3 mg/kg dose of the indicated RNAi agents for four months (QM×4 @ 3 mg/kg).

FIG. 7 depicts the study design of AD-65492 and AD-66017 subcutaneous administration to Cynomologous monkeys.

DETAILED DESCRIPTION OF THE INVENTION

Figure 1:
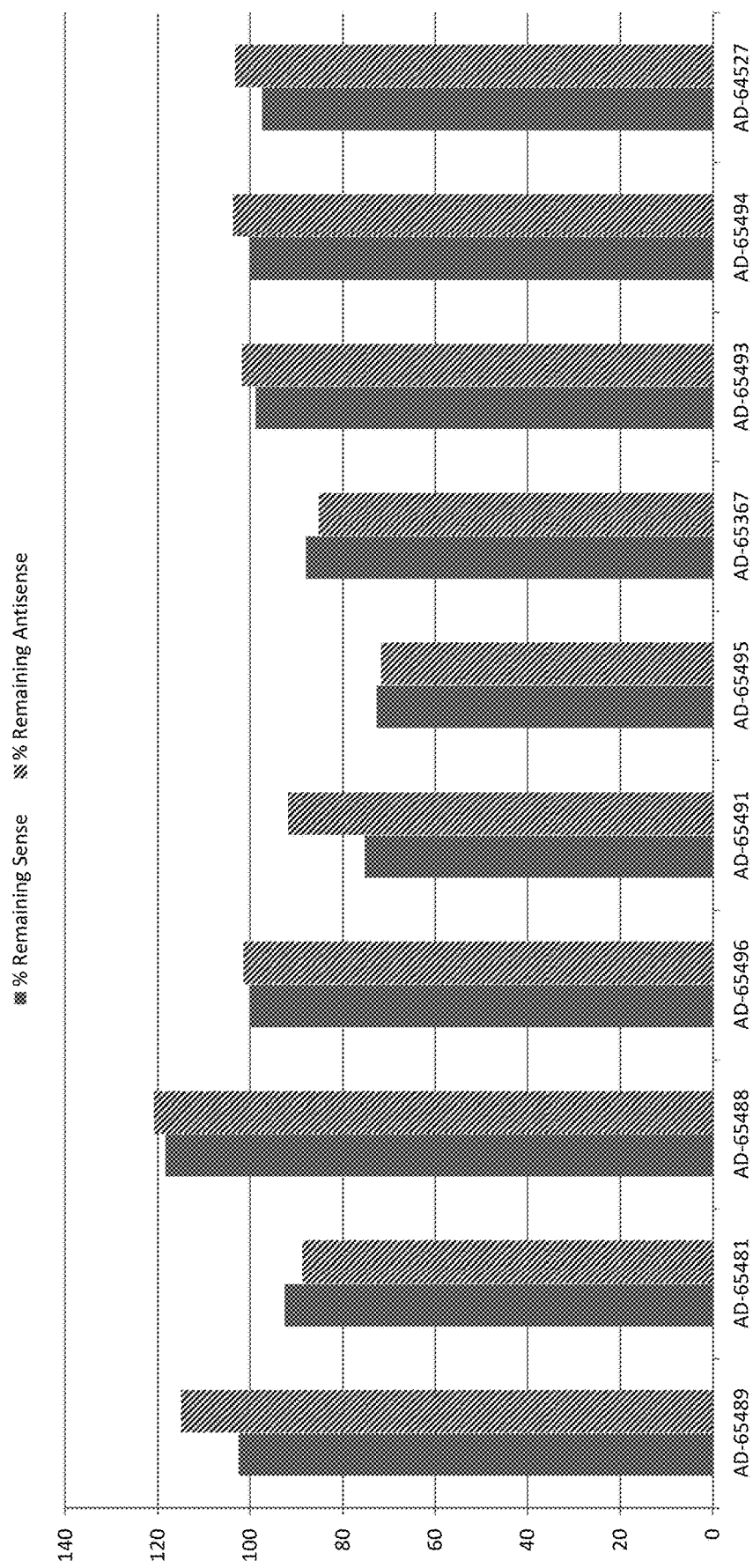
FIG. 1 is a graph depicting the stability of the indicated RNAi agents in a twenty-four hour tristosome stability assay.

The present invention provides RNAi agents, e.g., double stranded RNAi agents, and compositions targeting the Transthyretin (TTR) gene. The present invention also provides methods of inhibiting expression of TTR and methods of treating or preventing a TTR-associated disease in a subject using the RNAi agents, e.g., double stranded RNAi agents, of the invention. The present invention is based, at least in part, on the discovery that RNAi agents in which substantially all of the nucleotides on the sense strand and substantially all of the nucleotides of the antisense strand are modified nucleotides and that comprise no more than 8 2'-fluoro modifications (e.g., no more than 7 2'-fluoro modifications, no more than 6 2'-fluoro modifications, no more than 5 2'-fluoro modifications, no more than 4 2'-fluoro modifications, no more than 5 2'-fluoro modifications, no more than 4 2'-fluoro modifications, no more than 3 2'-fluoro modifications, or no more than 2 2'-fluoro modifications) on the sense strand, no more than 6 2'-fluoro modifications (e.g., no more than 5 2'-fluoro modifications, no more than 4 2'-fluoro modifications, no more than 3 2'-fluoro modifications, or no more than 2 2'-fluoro modifications) on the antisense strand, two phosphorothioate linkages at the 5'-end of the sense strand, two phosphorothioate linkages at the 5'-end of the antisense strand, and a ligand, e.g., a GalNAc$_3$ ligand, are shown herein to be effective in selectively silencing the activity of the TTR gene. These agents show surprisingly enhanced TTR gene silencing activity. Without intending to be limited by theory, it is believed that a combination or sub-combination of the foregoing modifications and the specific target sites in these RNAi agents confer to the RNAi agents of the invention improved efficacy, stability, potency, and durability.

The following detailed description discloses how to make and use compositions containing iRNAs to selectively inhibit the expression of a TTR gene, as well as compositions, uses, and methods for treating subjects having diseases and disorders that would benefit from inhibition and/or reduction of the expression of a TTR gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

The term "about" is used herein to mean within the typical ranges of tolerances in the art. For example, "about" can be understood as within about 2 standard deviations from the mean. In certain embodiments, about means+10%. In certain embodiments, about means+5%. When about is present before a series of numbers or a range, it is understood that "about" can modify each of the numbers in the series or range.

As used herein, a "transthyretin" ("TTR") refers to the well known gene and protein. TTR is also known as prealbumin, HsT2651, PALB, and TBPA. TTR functions as a transporter of retinol-binding protein (RBP), thyroxine (T4) and retinol, and it also acts as a protease. The liver secretes TTR into the blood, and the choroid plexus secretes TTR into the cerebrospinal fluid. TTR is also expressed in the pancreas and the retinal pigment epithelium. The greatest clinical relevance of TTR is that both normal and mutant TTR protein can form amyloid fibrils that aggregate into extracellular deposits, causing amyloidosis. See, e.g., Saraiva M. J. M. (2002) *Expert Reviews in Molecular Medicine*, 4(12):1-11 for a review. The molecular cloning and nucleotide sequence of rat transthyretin, as well as the distribution of mRNA expression, was described by Dickson, P. W. et al. (1985) J. Biol. Chem. 260(13)8214-8219. The X-ray crystal structure of human TTR was described in Blake, C. C. et al. (1974) *J Mol Biol* 88, 1-12. The sequence of a human TTR mRNA transcript can be found at National Center for Biotechnology Information (NCBI) RefSeq accession number NM_000371 (e.g., SEQ ID NOs:1 and 5). The sequence of mouse TTR mRNA can be found at RefSeq accession number NM_013697.2, and the sequence of rat TTR mRNA can be found at RefSeq accession number NM_012681.1. Additional examples of TTR mRNA sequences are readily available using publicly available databases, e.g., GenBank, UniProt, and OMIM.

As used herein, "target sequence" refers to a contiguous portion of the nucleotide sequence of an mRNA molecule formed during the transcription of a TTR gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a TTR gene. In one embodiment, the target sequence is within the protein coding region of the TTR gene. In another embodiment, the target sequence is within the 3' UTR of the TTR gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. In some embodiments, the target sequence is about 19 to about 30 nucleotides in length. In other embodiments, the target sequence is about 19 to about 25 nucleotides in length. In still other embodiments, the target sequence is about 19 to about 23 nucleotides in length. In some embodiments, the target sequence is about 21 to about 23 nucleotides in length. Ranges and lengths intermediate to the above recited ranges and lengths are also contemplated to be part of the invention.

In some embodiments of the invention, the target sequence of a TTR gene comprises nucleotides 615-637 of SEQ ID NO:1 or nucleotides 505-527 of SEQ ID NO:5 (i.e., 5'-GATGGGATTTCATGTAACCAAGA-3'; SEQ ID NO:4).

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA," "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of a TTR gene in a cell, e.g., a cell within a subject, such as a mammalian subject.

In one embodiment, an RNAi agent of the invention includes a single stranded RNA that interacts with a target RNA sequence, e.g., a TTR target mRNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer (Sharp et al. (2001) *Genes Dev.* 15:485). Dicer, a ribonuclease-III-like enzyme, processes these dsRNA into 19-23 base pair short interfering RNAs with characteristic two base 3' overhangs (Bernstein, et al., (2001) *Nature* 409:363). These siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded siRNA (ssRNA) (the antisense strand of an siRNA duplex) generated within a cell and which promotes the formation of a RISC complex to effect silencing of the target gene, i.e., a TTR gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded RNA as described herein or as chemically modified by the methods described in Lima et al., (2012) *Cell* 150:883-894.

In another embodiment, an "iRNA" for use in the compositions, uses, and methods of the invention is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., a TTR gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides.

As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, each strand of which is 24-30 nucleotides in length, that interacts with a target RNA sequence, e.g., a TTR target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, an RNAi agent of the invention is a dsRNA agent, each strand of which comprises 19-23 nucleotides that interacts with aTTR RNA sequence to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). In one embodiment, an RNAi agent of the invention is a dsRNA of 24-30 nucleotides that interacts with a TTR RNA sequence to direct the cleavage of the target RNA.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. In one embodiment of the dsRNA, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3' end of the antisense strand of the duplex. In certain embodiments, an extended overhang is present on the 5' end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNAi agent, i.e., no nucleotide overhang. A "blunt ended" RNAi agent is a dsRNA that is double stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a TTR mRNA. As used herein, the term "region of complementarity" refers to the region on the antisense strand that is substantially complementary to a sequence, for example a target sequence, e.g., a TTR nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, 2, or 1 nucleotides of the 5'- and/or 3'-terminus of the iRNA. In one embodiment, a double stranded RNAi agent of the invention include a nucleotide mismatch in the antisense strand. In another embodiment, a double stranded RNAi agent of the invention include a nucleotide mismatch in the sense strand. In one embodiment, the nucleotide mismatch is, for example, within 5, 4, 3, 2, or 1 nucleotides from the 3'-terminus of the iRNA. In another embodiment, the nucleotide mismatch is, for example, in the 3'-terminal nucleotide of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a TTR gene). For example, a polynucleotide is complementary to at least a part of a TTR mRNA if the sequence is substantially complementary to a non-interrupted portion of an mRNA encoding a TTR gene.

Accordingly, in some embodiments, the antisense polynucleotides disclosed herein are fully complementary to the target TTR sequence. In other embodiments, the antisense polynucleotides disclosed herein are fully complementary to SEQ ID NO:2 (5'-UGGGAUUUCAUGUAACCAAGA-3'). In one embodiment, the antisense polynucleotide sequence is 5'-UCUUGGUUACAUGAAAUCCCAUC-3' (SEQ ID NO:3).

In other embodiments, the the antisense polynucleotides disclosed herein are substantially complementary to the target TTR sequence and comprise a contiguous nucleotide sequence which is at least about 80% complementary over its entire length to the equivalent region of the nucleotide sequence of any one of SEQ ID NO:2 (5'-UGGGAUUU-CAUGUAACCAAGA-3'), or a fragment of any one of SEQ ID NOs:1, 2, and 5, such as about 85%, about 86%, about 87%, about 88%, about 89%, about 90%, about % 91%, about 92%, about 93%, about 94%, about 95%, about 96%, about 97%, about 98%, or about 99% complementary.

In one embodiment, an RNAi agent of the invention includes a sense strand that is substantially complementary to an antisense polynucleotide which, in turn, is complementary to a target TTR sequence, and wherein the sense strand polynucleotide comprises a contiguous nucleotide sequence which is at least about 80% complementary over its entire length to the equivalent region of the nucleotide sequence of any one of the sequences in Tables 1, 3, 5, 6, and 7, such as about 85%, about 86%, about 87%, about 88%, about 89%, about 90%, about % 91%, about 92%, about 93%, about 94%, about 95%, about 96%, about 97%, about 98%, or about 99% complementary.

In another embodiment, an RNAi agent of the invention includes an antisense strand that is substantially complementary to the target TTR sequence and comprise a contiguous nucleotide sequence which is at least about 80% complementary over its entire length to the equivalent region of the nucleotide sequence of any one of the sequences in Table 1 and 3, such as about 85%, about 86%, about 87%, about 88%, about 89%, about 90%, about % 91%, about 92%, about 93%, about 94%, about 95%, about 96%, about 97%, about 98%, or about 99% complementary.

In some embodiments, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

In one aspect of the invention, an agent for use in the methods and compositions of the invention is a single-stranded antisense nucleic acid molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

A "TTR-associated disease," as used herein, is intended to include any disease associated with the TTR gene or protein. Such a disease may be caused, for example, by excess production of the TTR protein, by TTR gene mutations, by abnormal cleavage of the TTR protein, by abnormal interactions between TTR and other proteins or other endogenous or exogenous substances. A "TTR-associated disease" includes any type of TTR amyloidosis (ATTR) wherein TTR plays a role in the formation of abnormal extracellular aggregates or amyloid deposits. TTR-associated diseases include senile systemic amyloidosis (SSA), systemic familial amyloidosis, familial amyloidotic polyneuropathy (FAP), familial amyloidotic cardiomyopathy (FAC), leptomeningeal/Central Nervous System (CNS) amyloidosis, amyloidotic vitreous opacities, carpal tunnel syndrome, and hyperthyroxinemia. Symptoms of TTR amyloidosis include sensory neuropathy (e.g., paresthesia, hypesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy.

II. iRNAs of the Invention

The present invention provides iRNAs which selectively inhibit the expression of one or more TTR genes. In one embodiment, the iRNA agent includes double stranded ribonucleic acid (dsRNA) molecules for inhibiting the expression of a TTR gene in a cell, such as a cell within a subject, e.g., a mammal, such as a human having a TTR-associated disease. The dsRNA includes an antisense strand having a region of complementarity which is complementary to at least a part of an mRNA formed in the expression of a TTR gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the TTR gene, the iRNA selectively inhibits the expression of the TTR gene (e.g., a human, a primate, a non-primate, or a bird TTR gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a TTR gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is about 15 to about 20 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target TTR gene expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. In certain embodiments, longer, extended overhangs are possible.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in any one of Tables 1, 3, 5, 6, and 7, and the corresponding antisense strand of the sense strand is selected from the group of sequences of any one of Tables 1, 3, 5, 6, and 7. In this aspect, one of the two sequences is complementary to the other of the two sequences, with one of the sequences being substantially complementary to a sequence of an mRNA generated in the expression of a TTR gene. As such, in this aspect, a dsRNA will include two oligonucleotides, where one oligonucleotide is described as the sense strand in any one of Tables 1, 3, 5, 6, and 7, and the second oligonucleotide is described as the corresponding antisense strand of the sense strand in any one of Tables 1, 3, 5, 6, and 7. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 1, 3, 5, 6, and 7 are described as modified and/or conjugated sequences, the RNA of the iRNA of the invention e.g., a dsRNA of the invention, may comprise any one of the sequences set forth in Tables 1, 3, 5, 6, and 7 that is un-modified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 1, 3, 5, 6, and 7, dsRNAs described herein can include at least one strand of a length of minimally 21 nucleotides. It can be reasonably expected that shorter duplexes having one of the sequences of any one of Tables 1, 3, 5, 6, and 7 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 1, 3, 5, 6, and 7, and differing in their ability to inhibit the expression of a TTR gene by not more than about 5, 10, 15, 20, 25, or 30% inhibition from a dsRNA comprising the full sequence, are contemplated to be within the scope of the present invention.

In addition, the RNAs provided in any one of Tables 1, 3, 5, 6, and 7 identify a site(s) in a TTR transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 1, 3, 5, 6, and 7 coupled to additional nucleotide sequences taken from the region contiguous to the selected sequence in a TTR gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 1, 3, 5, 6, and 7 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 1, 3, 5, 6, and 7, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of a TTR gene, generally does not contain any mismatch within the central 13 nucleotides. The methods described herein or methods known in the art can be used to determine whether an iRNA containing a mismatch to a target sequence is effective in inhibiting the expression of a TTR gene. Consideration of the efficacy of iRNAs with mismatches in inhibiting expression of a TTR gene is important, especially if the particular region of complementarity in a TTR gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified. In some embodiments, substantially all of the nucleotides of an iRNA of the invention are modified and the iRNA comprises no more than 8 2'-fluoro modifications (e.g., no more than 7 2'-fluoro modifications, no more than 6 2'-fluoro modifications, no more than 5 2'-fluoro modification, no more than 4 2'-fluoro modifications, no more than 3 2'-fluoro modifications, or no more than 2 2'-fluoro modifications) on the sense strand and no more than 6 2'-fluoro modifications (e.g., no more than 5 2'-fluoro modifications, no more than 4 2'-fluoro modifications, no more than 3 2'-fluoro modifications, or no more than 2 2'-fluoro modifications) on the antisense strand. In other embodiments, all of the nucleotides of an iRNA of the invention are modified and the iRNA comprises no more than 8 2'-fluoro modifications (e.g., no more than 7 2'-fluoro modifications, no more than 6 2'-fluoro modifications, no more than 5 2'-fluoro modification, no more than 4 2'-fluoro modifications, no more than 3 2'-fluoro modifications, or no more than 2 2'-fluoro modifications) on the sense strand and no more than 6 2'-fluoro modifications (e.g., no more than 5 2'-fluoro modifications, no more than 4 2'-fluoro modifications, no more than 3 2'-fluoro modifications, or no more than 2 2'-fluoro modifications) on the antisense strand. iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE 39,464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science*, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)_2.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

The RNA of an iRNA of the invention can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxythymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more bicyclic sugar moieties. A "bicyclic sugar" is a furanosyl ring modified by the bridging of two atoms. A"bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C (CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-0-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose.

CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PC publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification.

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

A. Modified iRNAs Comprising Motifs of the Invention

In certain aspects of the invention, the double stranded RNAi agents of the invention include chemical modifications as disclosed, for example, in U.S. Provisional Application No. 61/561,710, filed on Nov. 18, 2011, or in PCT/US2012/065691, filed on Nov. 16, 2012, the entire contents of each of which are incorporated herein by reference.

More specifically, it has been surprisingly discovered that when the sense strand and antisense strand of the double stranded RNAi agent are modified to have one or more motifs of three identical modifications on three consecutive nucleotides at or near the cleavage site of at least one strand of an RNAi agent, the gene silencing activity of the RNAi agent was superiorly enhanced.

Accordingly, the invention provides double stranded RNAi agents capable of inhibiting the expression of a target gene (i.e., TTR gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but not limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TI can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. In one embodiment, all of the nucleotides of an iRNA of the invention are modified and the iRNA comprises no more than 8 2'-fluoro modifications (e.g., no more than 7 2'-fluoro modifications, no more than 6 2'-fluoro modifications, no more than 5 2'-fluoro modifications, no more than 4 2'-fluoro modifications, no more than 3 2'-fluoro modifications, or no more than 2 2'-fluoro modifications) on the sense strand and no more than 6 2'-fluoro modifications (e.g., no more than 5 2'-fluoro modifications, no more than 4 2'-fluoro modifications, no more than 3 2'-fluoro modifications, or no more than 2 2'-fluoro modifications) on the antisense strand. Optionally, the RNAi agent further comprises a ligand (preferably GalNAc$_3$).

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisenese strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5' end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one embodiment, the sense strand sequence may be represented by formula (I):

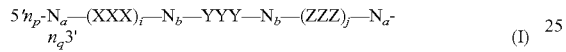

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the 1st nucleotide, from the 5'-end; or optionally, the count starting at the 1st paired nucleotide within the duplex region, from the 5'-end.

In one embodiment, i is 1 and j is 0, or i is 0 and j is 1, or both i and j are 1. The sense strand can therefore be represented by the following formulas:

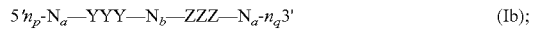

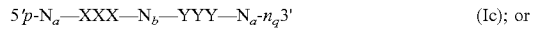

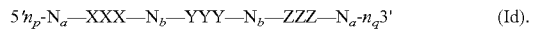

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides. Each of X, Y and Z may be the same or different from each other.

In other embodiments, i is 0 and j is 0, and the sense strand may be represented by the formula:

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

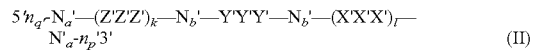

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1st nucleotide, from the 5'-end; or optionally, the count starting at the 1st paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

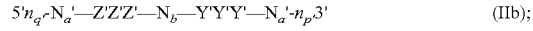

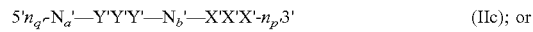

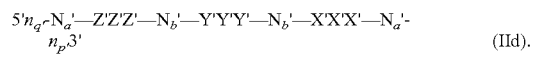

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

$$5'n_p\text{-}N_a\text{—}Y'Y'Y'\text{—}N_a\text{-}n_q 3' \qquad (Ia).$$

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:
i, j, k, and l are each independently 0 or 1;
p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

$5'n_p\text{-}N_a\text{—}YYY\text{—}N_a\text{-}n_q 3'$ $3'n_p'\text{-}N_a'\text{—}Y'Y'Y'\text{—}N_a'n_q' 5' \qquad (IIIa)$ $5'n_p\text{-}N_a\text{—}YYY\text{—}N_b\text{—}ZZZ\text{—}N_a\text{-}n_q 3'$ $3'n_p'\text{-}N_a'\text{—}Y'Y'Y'\text{—}N_b'\text{—}Z'Z'Z'\text{—}N_a'n_q' 5' \qquad (IIIb)$ $5'n_p\text{-}N_a\text{—}XXX\text{—}N_b\text{—}YYY\text{—}N_a\text{-}n_q 3'$ $3'n_p'\text{-}N_a'\text{—}X'X'X'\text{—}N_b'\text{—}Y'Y'Y'\text{—}N_a'\text{-}n_q' 5' \qquad (IIIc)$ $5'n_p\text{-}N_a\text{—}XXX\text{—}N_b\text{—}YYY\text{—}N_b\text{—}ZZZ\text{—}N_a\text{-}n_q 3'$ $3'n_p'\text{-}N_a'\text{—}X'X'X'\text{—}N_b'\text{—}Y'Y'Y'\text{—}N_b'\text{—}Z'Z'Z'\text{—}N_a\text{-}n_q' 5' \qquad (IIId)$ $5'\text{-}N_a\text{—}YYY\text{—}N_b\text{-}3'$ $3'n_p'\text{-}N_a'\text{—}Y'Y'Y'\text{—}N_b' 5' \qquad (IIIe)$ When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

When the RNAi agent is represented as formula (IIIe), each $N_a$, $N_a'$, $N_b$, and $N_b'$ independently represents an oligonucleotide sequence comprising 0-25 nucleotides which are either modified or unmodified or combinations thereof, each sequence comprising at least two differently modified nucleotides.

Each of X, Y and Z in formulas (III), (IIIa), (IIIb), (IIIc), (IIId), and (IIIe) may be the same or different from each other.

When the RNAi agent is represented by formula (III), (IIIa), (IIIb), (IIIc), (IIId), and (IIIe), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, two RNAi agents represented by formula (III), (IIIa), (IIIb), (IIIc), (IIId), and (IIIe) are linked to each other at the 5' end, and one or both of the 3' ends and are optionally conjugated to to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

As described in more detail below, the RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the RNAi agent, e.g., for use in the methods of the invention, is an agent selected from the group of agents listed in any one of Tables 1, 3, 5, 6, and 7. These agents may further comprise a ligand.

In certain embodiments, the RNAi agent of the invention is an agent selected from the group consisting of AD-66016, AD-65492, AD-66017, and AD-66018.

IV. IRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med.* Chem. Let., 1994, 4:1053-1060), a thioether, e.g., beryl-S-tritylthiol (Manoharan et al., *Ann. N.Y. Acad Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, monovalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, ligands include monovalent or multivalent galactose. In certain embodiments, ligands include cholesterol.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 11). An RFGF analogue (e.g., amino acid sequence AALLPVLLAAP (SEQ ID NO: 12) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) (SEQ ID NO: 13) and the *Drosophila* Antennapedia protein (RQIKIWFQNRRMK-WKK) (SEQ ID NO: 14) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include TTR and above (e.g., TTR, C6, C7, or C8) sugars; di- and trisaccharides include sugars having two or three monosaccharide units (e.g., TTR, C6, C7, or C8).

In one embodiment, a carbohydrate conjugate for use in the compositions and methods of the invention is a monosaccharide. In another embodiment, a carbohydrate conjugate for use in the compositions and methods of the invention is selected from the group consisting of:

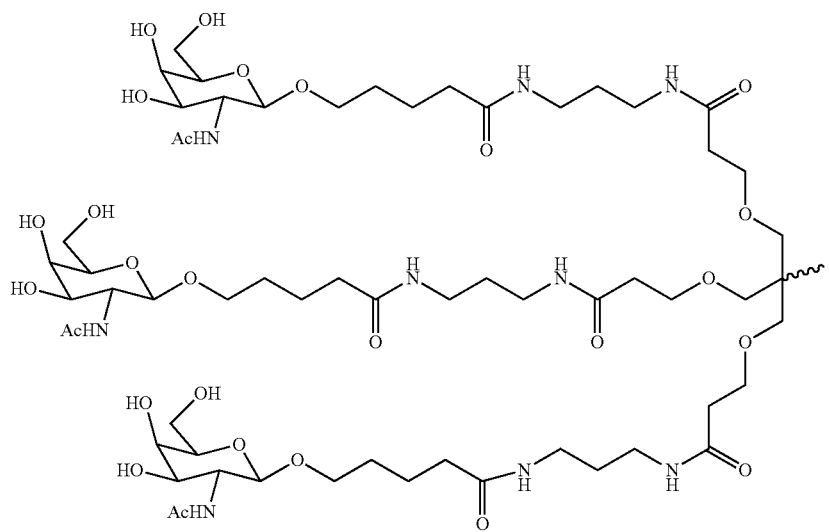

Formula II

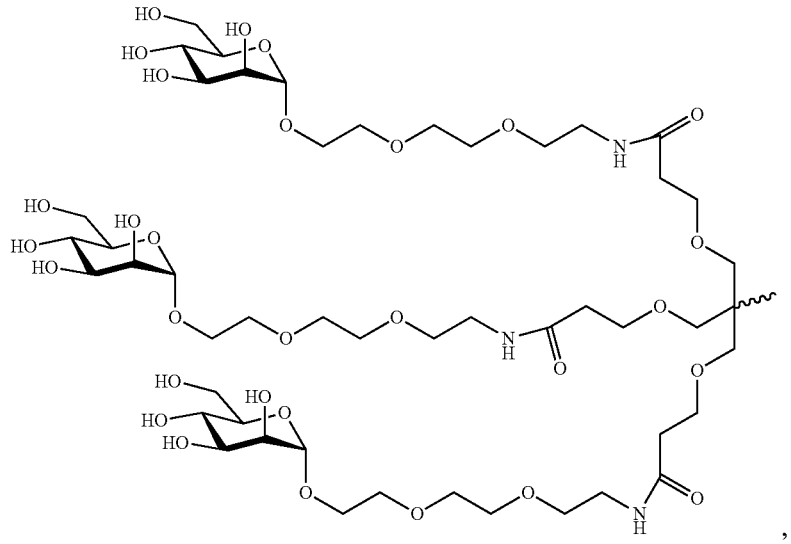

Formula III

-continued
Formula IV
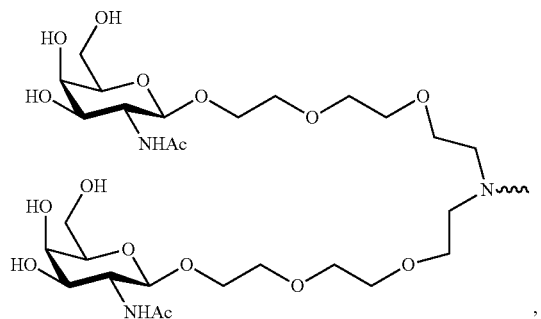
Formula V
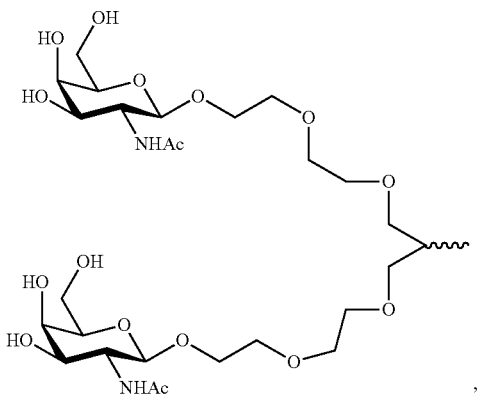
Formula VI
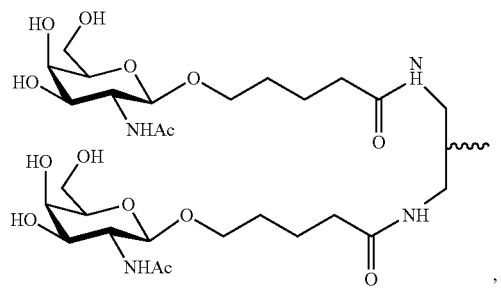
Formula VII
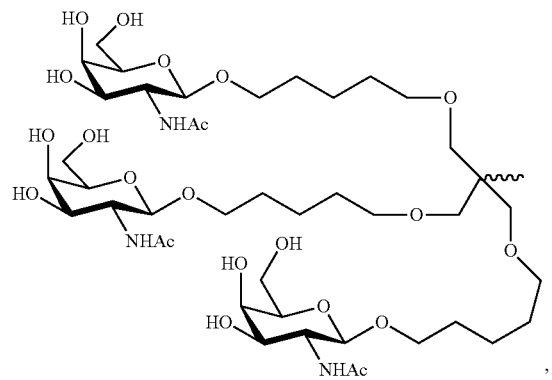
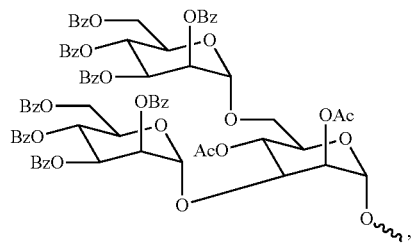
Formula VIII
Formula IX
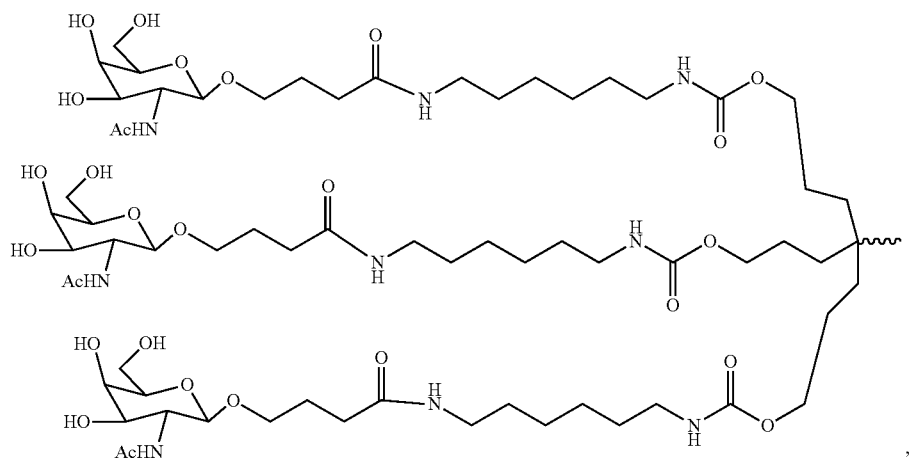

-continued
Formula X
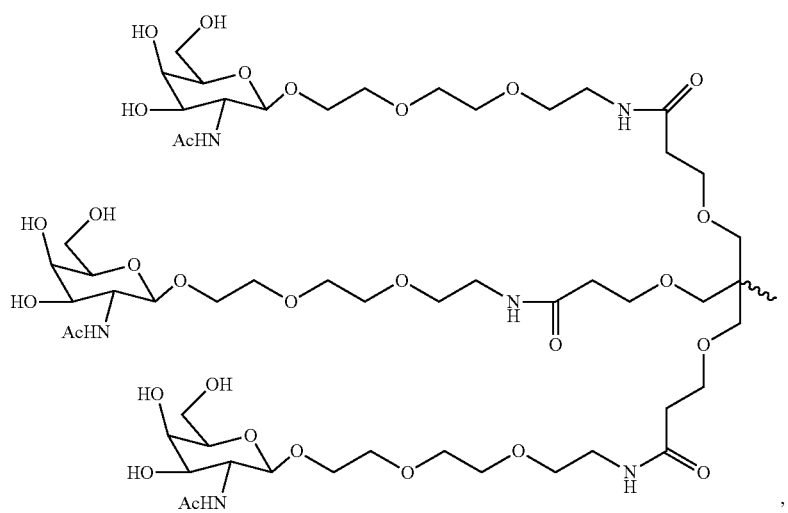
Formula XI
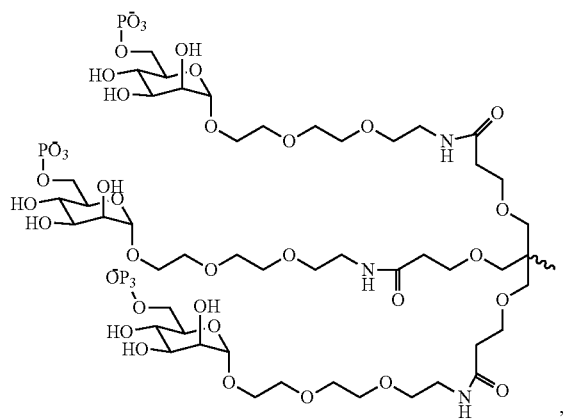
Formula XII
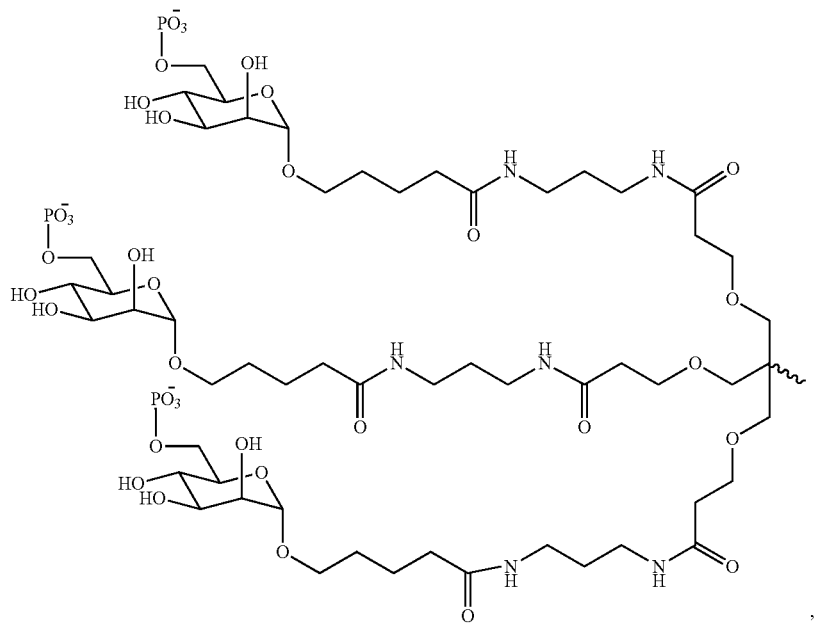

-continued
Formula XIII
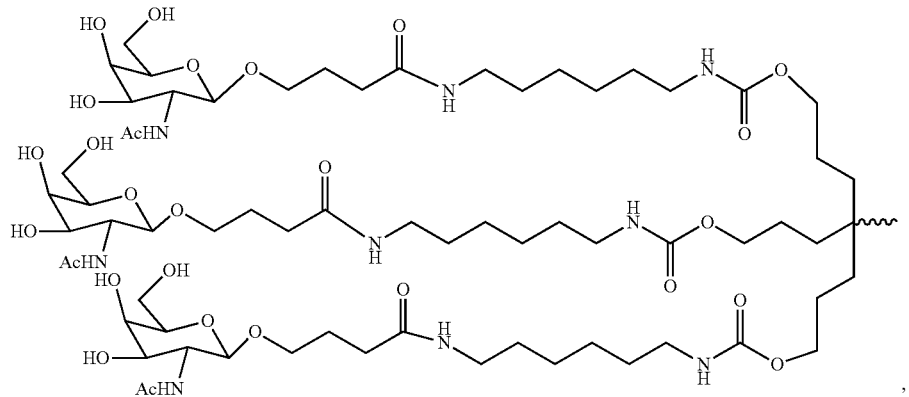
Formula XIV
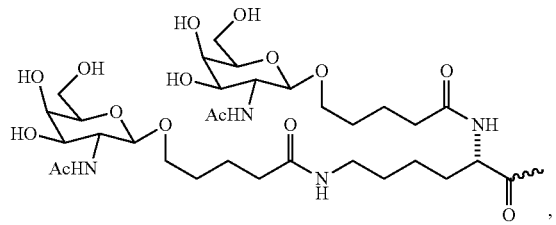
Formula XV
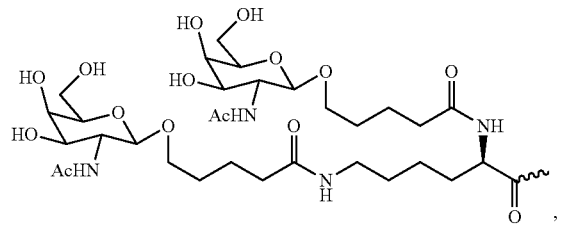
Formula XVI
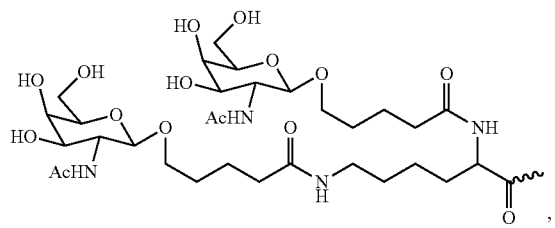
Formula XVII
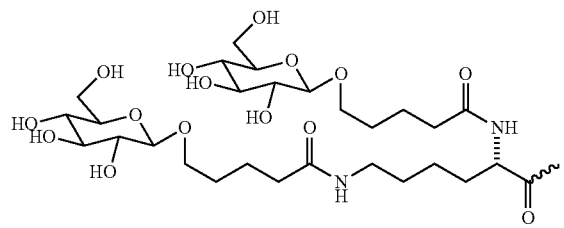
Formula XVIII
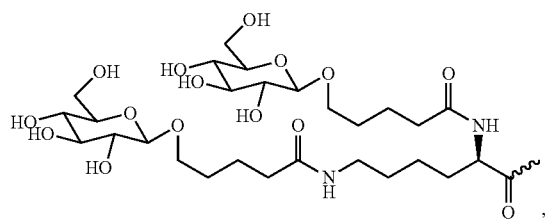
Formula XIX
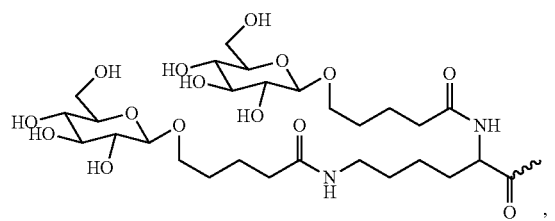
Formula XX
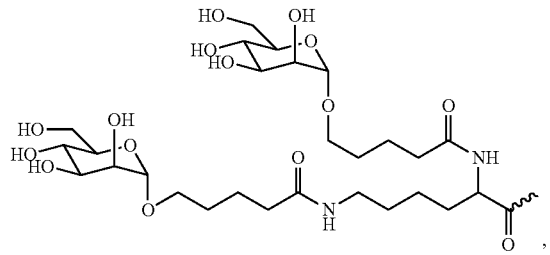
Formula XXI
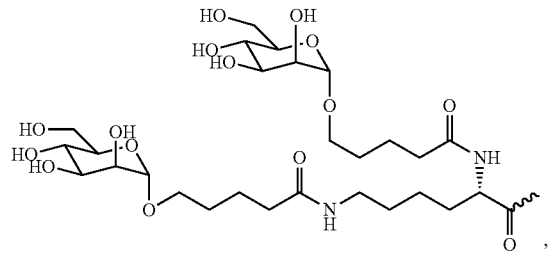

-continued
Formula XXII
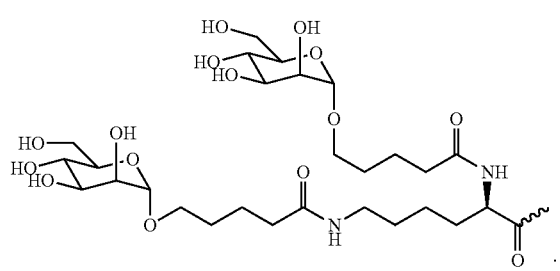
In one embodiment, the monosaccharide is an N-acetyl-galactosamine, such as
Formula II
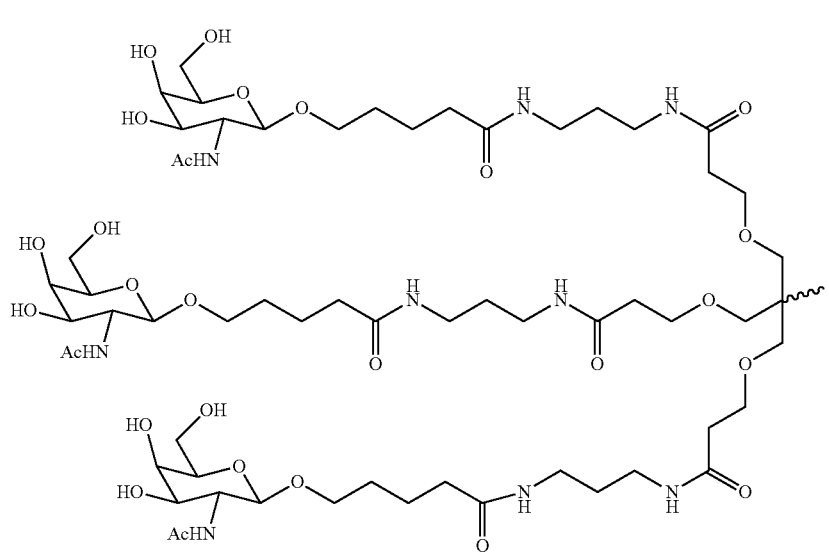
40
Another representative carbohydrate conjugate for use in the embodiments described herein includes, but is not limited to,

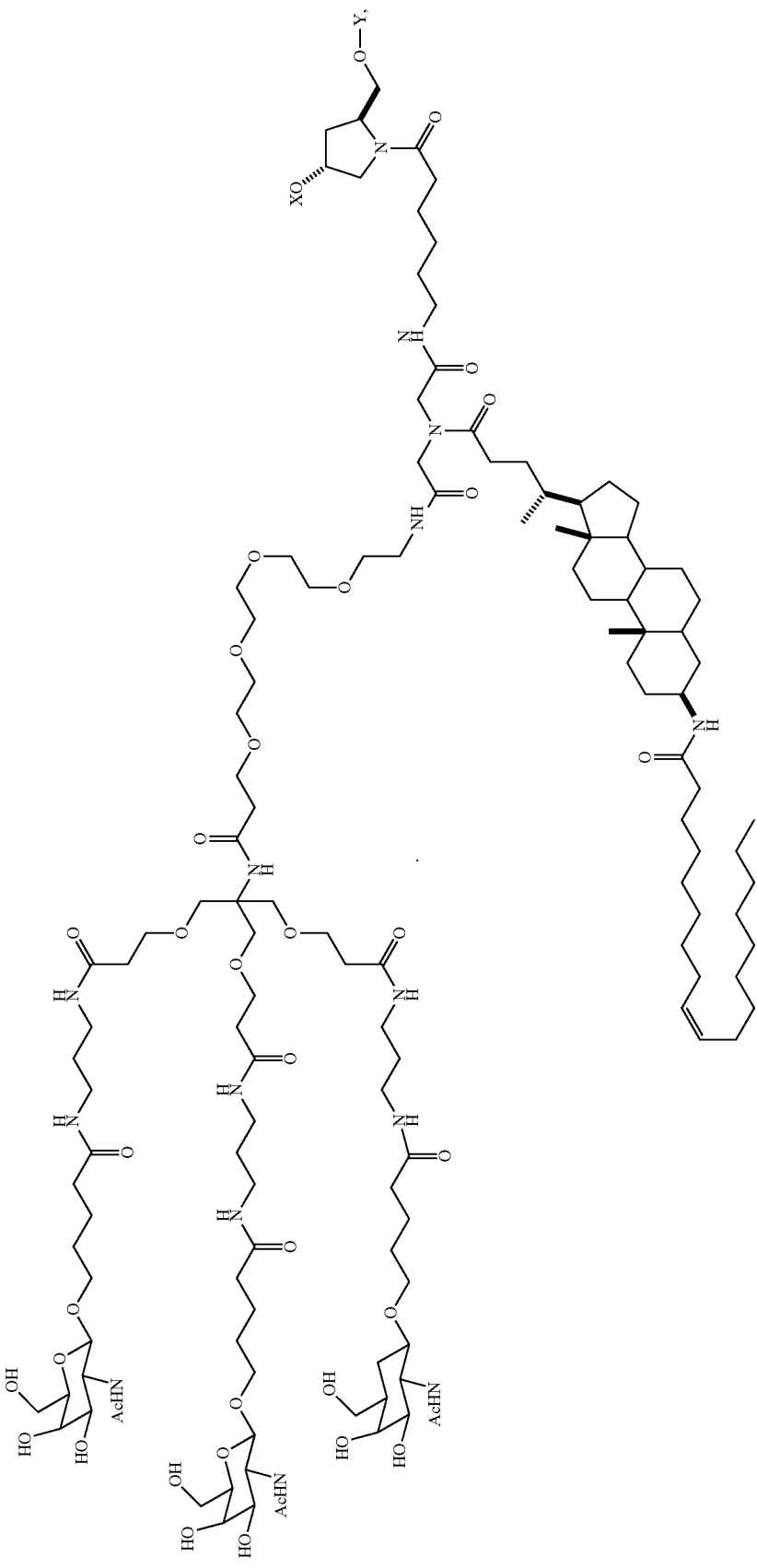
(Formula XXIII)

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the carbohydrate conjugate further comprises one or more additional ligands as described above, such as, but not limited to, a PK modulator and/or a cell permeation peptide.

Additional carbohydrate conjugates suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhererocaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)
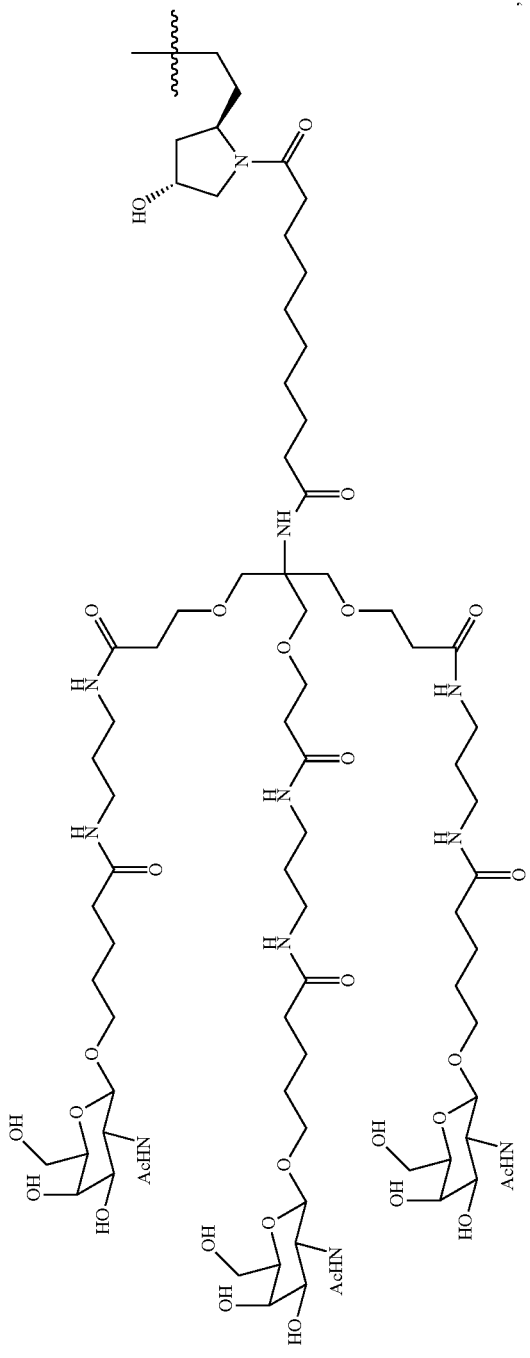
(Formula XXV)
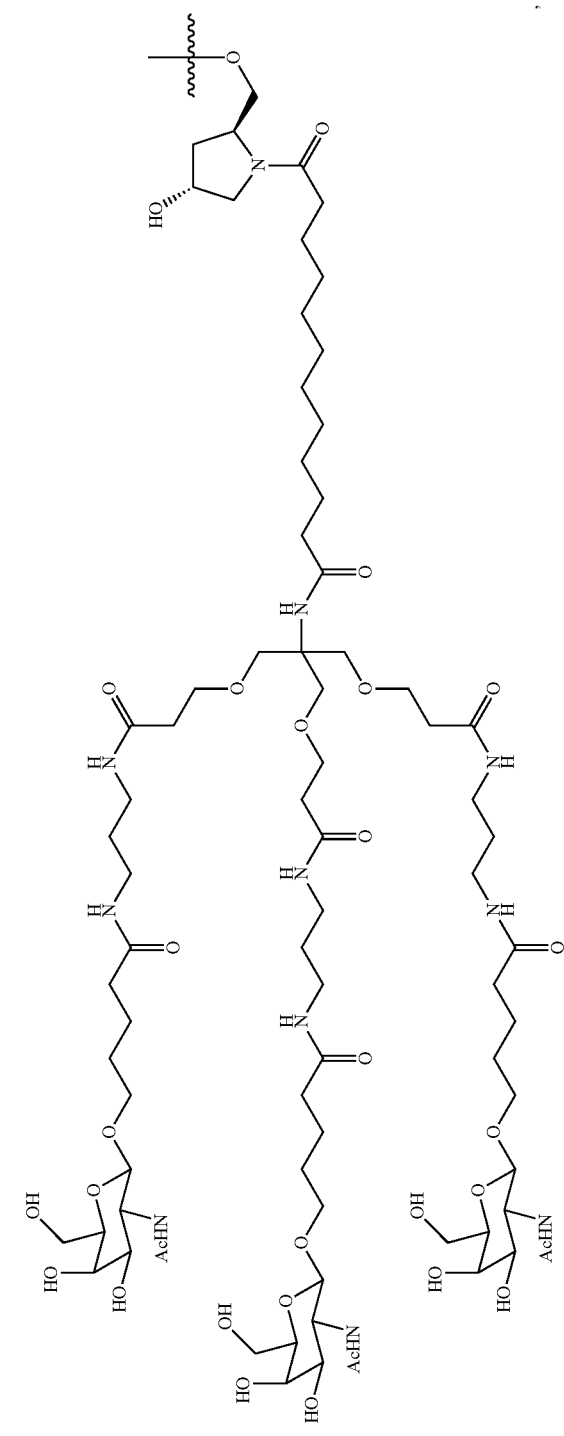

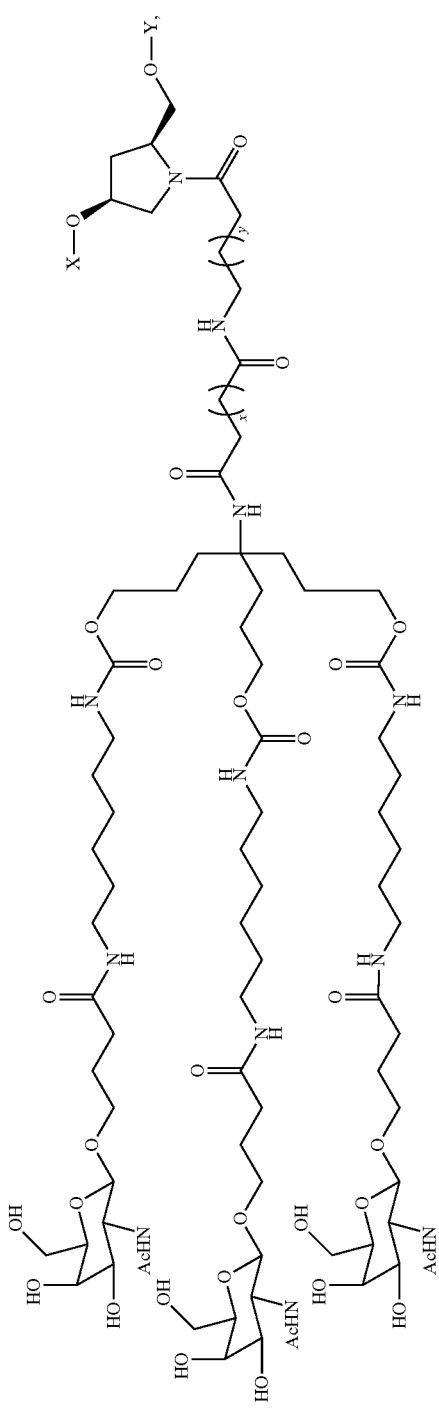
(Formula XXVI)
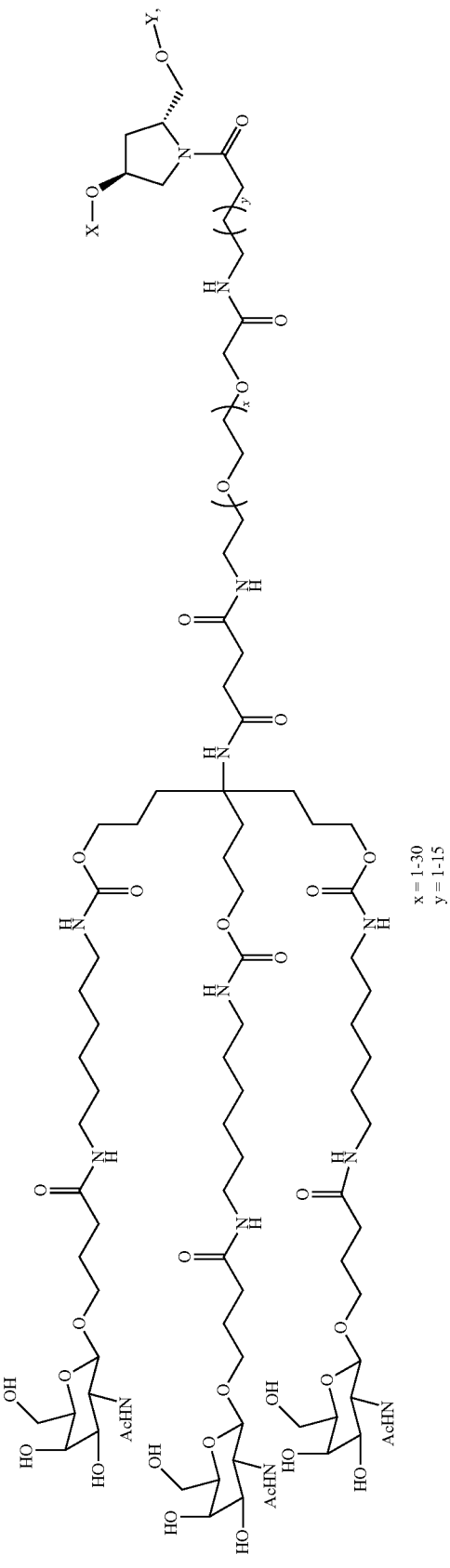
(Formula XXVII)
x = 1-30
y = 1-15

-continued
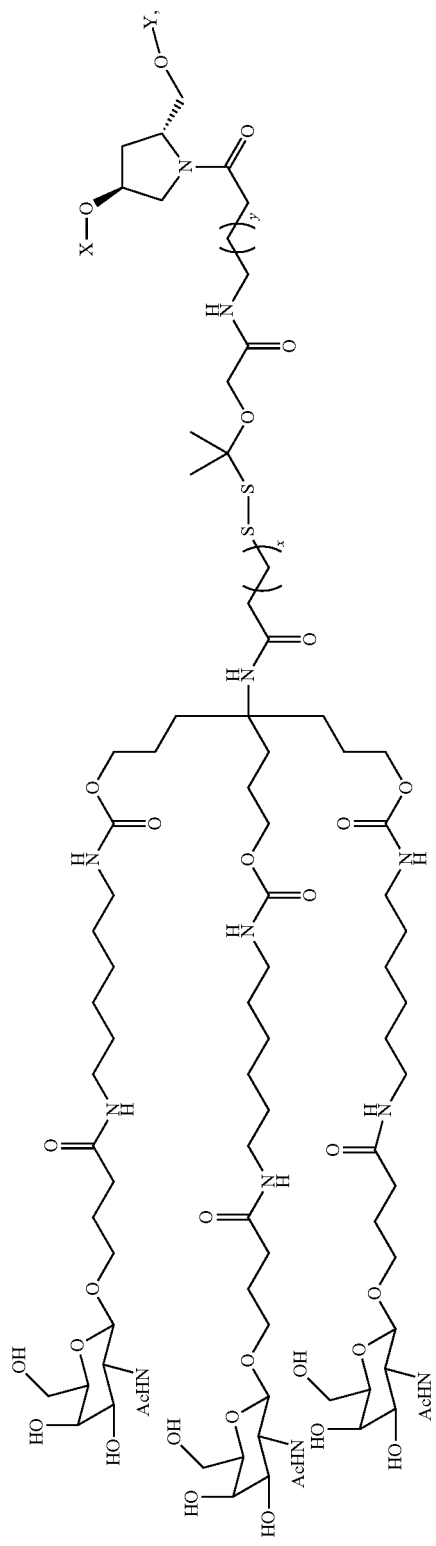
(Formula XXVIII)
x = 1-30
y = 1-15
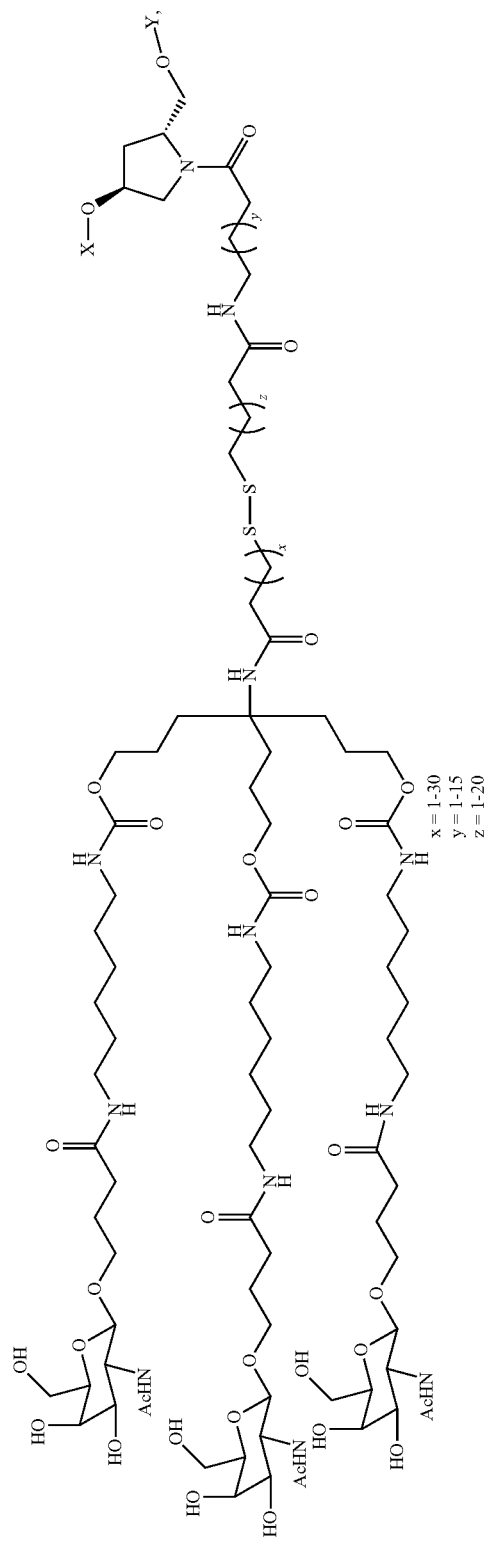
(Formula XXIX)
x = 1-30
y = 1-15
z = 1-20

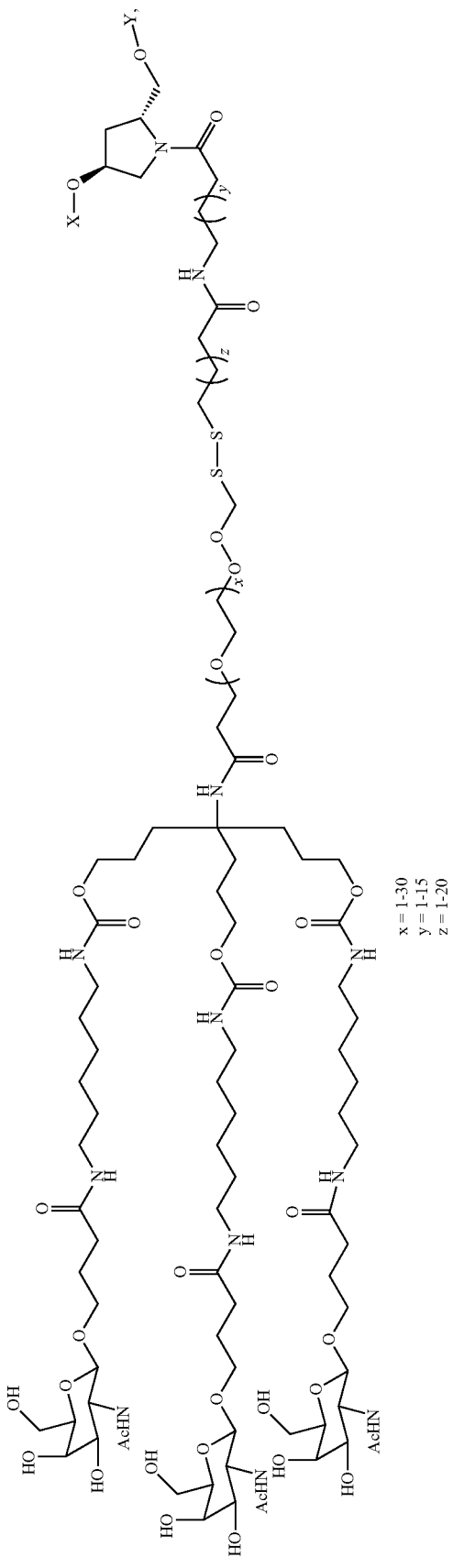
(Formula XXX)
x = 1-30
y = 1-15
z = 1-20
and
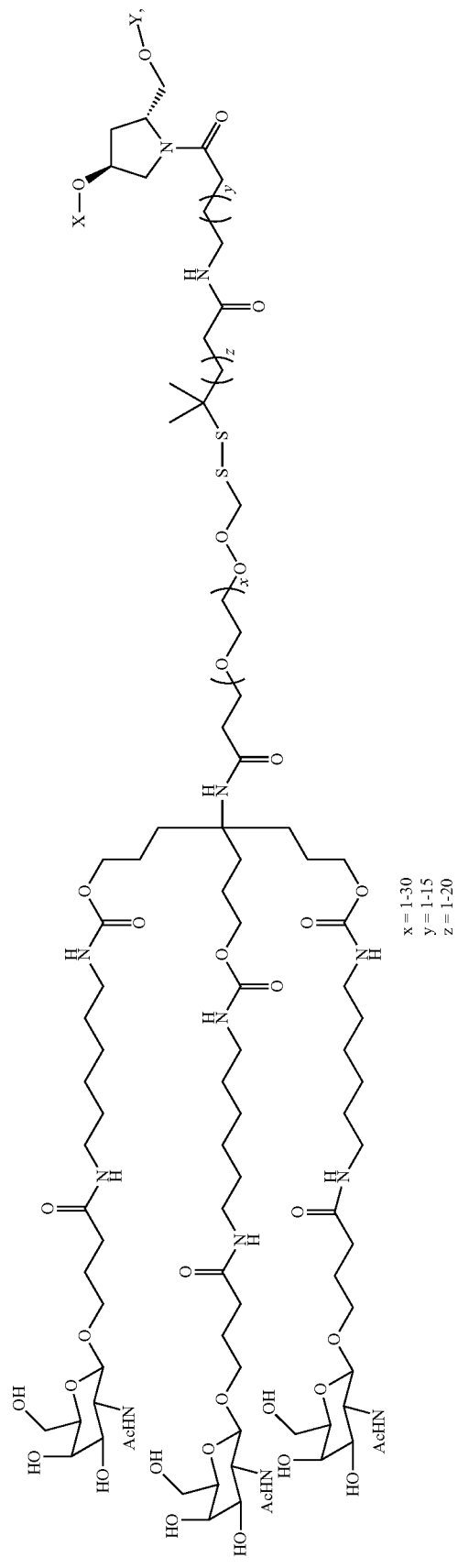
(Formula XXXI)
x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

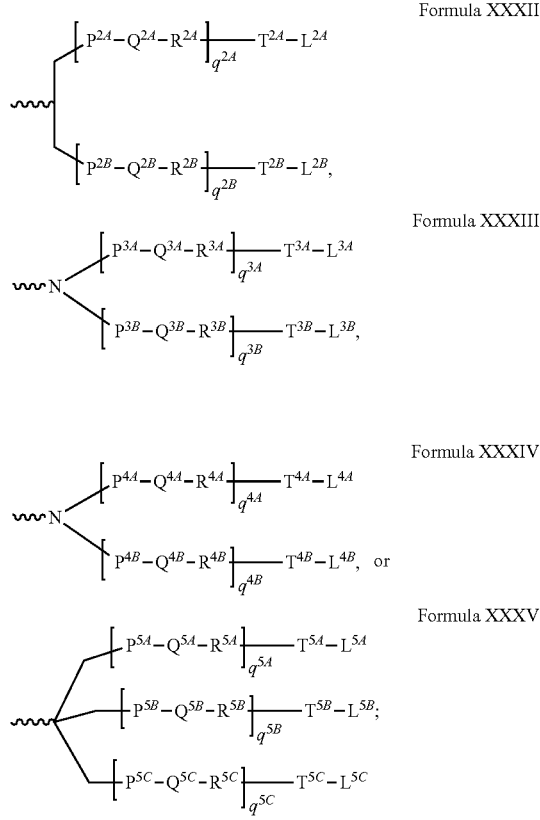

Formula XXXII

Formula XXXIII

Formula XXXIV

Formula XXXV wherein:

q2A, q2B, q3A, q3B, q4A, q4B, q5A, q5B and q5C represent independently for each occurrence q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO,

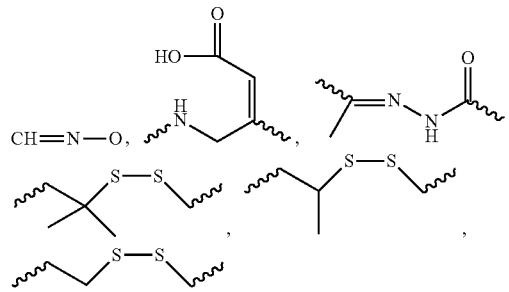

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXVI):

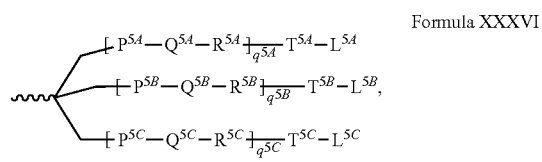

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an IRNA of the Invention

The delivery of an iRNA of the invention to a cell e.g., a cell within a subject, such as a human subject (e.g., a subject in need thereof, such as a subject having a disease, disorder or condition associated with TTR) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) Clin. *Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the TTR gene can be expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J*. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or HI RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VI. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a TTR gene. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a TTR gene. In one embodiment, the iRNA agents of the invention, e.g., a dsRNA agent, is formulated for subcutaneous administration in a pharmaceutically acceptable carrier The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. Administration may also be repeated, for example, on a monthly basis, or on a quartlerly basis, e.g., approximately every 12 weeks. After an initial treatment regimen, the treatments can be administered on a less frequent basis. For example, after administration weekly or biweekly for three months, administration can be repeated once per month, for six months or a year or longer.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, at not more than 1, 2, 3, or 4 week intervals, or at not more than 9, 10, 11, or 12 week intervals. In some embodiments of the invention, a single dose of the pharmaceutical compositions of the invention is administered once per week. In other embodiments of the invention, a single dose of the pharmaceutical compositions of the invention is administered bimonthly. In other embodiments, a single dose of the pharmaceutical compositions of the invention is administered monthly. In still other embodiments, a single dose of the pharmaceutical compositions of the invention is administered quarterly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate iRNA. In some cases the liposomes are also specifically targeted, e.g., to direct the iRNA to particular cell types.

A liposome containing an iRNA agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA agent preparation is then added to the micelles that include the lipid component. The cationic groups on the lipid interact with the iRNA agent and condense around the iRNA agent to form a liposome. After condensation, the detergent is removed, e.g., by dialysis, to yield a liposomal preparation of iRNA agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., Proc. Natl. Acad. Sci., USA 8:7413-7417, 1987; U.S. Pat. Nos. 4,897,355; 5,171,678; Bangham, et al. M. Mol. Biol. 23:238, 1965; Olson, et al. Biochim. Biophys. Acta 557:9, 1979; Szoka, et al. Proc. Natl. Acad. Sci. 75: 4194, 1978; Mayhew, et al. Biochim. Biophys. Acta 775:169, 1984; Kim, et al. Biochim. Biophys. Acta 728:339, 1983; and Fukunaga, et al. Endocrinol. 115:757, 1984. Commonly used techniques for preparing lipid aggregates of appropriate size for use as delivery vehicles include sonication and freeze-thaw plus extrusion (see, e.g., Mayer, et al. Biochim. Biophys. Acta 858:161, 1986). Microfluidization can be used when consistently small (50 to 200 nm) and relatively uniform aggregates are desired (Mayhew, et al. Biochim. Biophys. Acta 775:169, 1984). These methods are readily adapted to packaging iRNA agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNA agents to macrophages.

Further advantages of liposomes include: liposomes obtained from natural phospholipids are biocompatible and biodegradable; liposomes can incorporate a wide range of water and lipid soluble drugs; liposomes can protect encapsulated iRNA agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.*

179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA agent into the skin. In some implementations, liposomes are used for delivering iRNA agent to epidermal cells and also to enhance the penetration of iRNA agent into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA agent can be delivered, for example, subcutaneously by infection in order to deliver iRNA agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in PCT Publication No. WO 2008/042973, the entire contents of which are incorporated herein by reference.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane:

10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

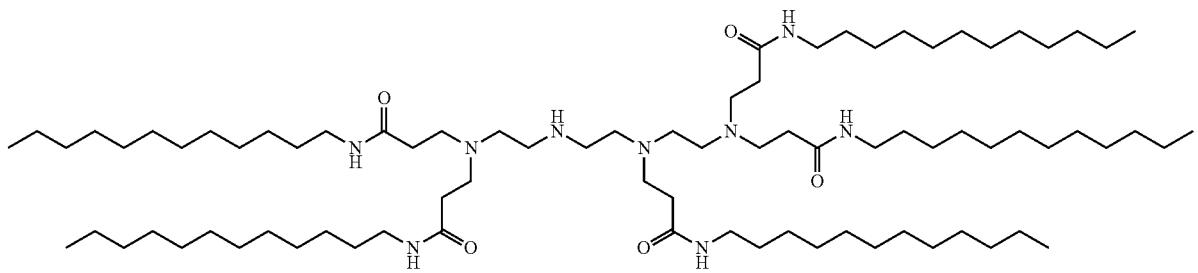

ND98 Isomer I

LNP01 formulations are described, e.g., in International Application Publication No. WO 2008/042973, which is hereby incorporated by reference.

Additional exemplary lipid-dsRNA formulations are described in Table 1.

TABLE A

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |

TABLE A-continued

| | Ionizable/Cationic Lipid | cationic lipid/non-cationic lipid/cholesterol/PEG-lipid conjugate Lipid:siRNA ratio |
|---|---|---|
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described in PCT Publication No. WO 2010/088537, the entire contents of which are hereby incorporated herein by reference.

MC3 comprising formulations are described, e.g., in U.S. Publication No. 2010/0324120, filed Jun. 10, 2010, the entire contents of which are hereby incorporated by reference.

ALNY-100 comprising formulations are described in PCT Publication No. WO 2010/054406, the entire contents of which are hereby incorporated herein by reference.

C12-200 comprising formulations are described in PCT Publication No. WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include polyamino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An iRNA agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-20 alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), iRNAMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), Trans-Pass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-iRNA mechanism and which are useful in treating a hemolytic disorder. Examples of such agents include, but are not limited to an anti-inflammatory agent, anti-steatosis agent, anti-viral, and/or anti-fibrosis agent.

In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by TTR expression. In any event, the administering physician can adjust the amount and timing of iRNA administration on the basis of results observed using standard measures of efficacy known in the art or described herein.

VII. Methods for Inhibiting TTR Expression

The present invention also provides methods of inhibiting expression of a transthyretin (TTR) in a cell. The methods include contacting a cell with an RNAi agent, e.g., double stranded RNAi agent, in an amount effective to inhibit expression of TTR in the cell, thereby inhibiting expression of TTR in the cell.

Contacting of a cell with an RNAi agent, e.g., a double stranded RNAi agent, may be done in vitro or in vivo. Contacting a cell in vivo with the RNAi agent includes contacting a cell or group of cells within a subject, e.g., a human subject, with the RNAi agent. Combinations of in vitro and in vivo methods of contacting a cell or group of cells are also possible. Contacting a cell or a group of cells may be direct or indirect, as discussed above. Furthermore, contacting a cell or a group of cells may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest, e.g., the liver of a subject.

The term "inhibiting," as used herein, is used interchangeably with "reducing," "silencing," "downregulating", "suppressing", and other similar terms, and includes any level of inhibition. Preferably inhibiting includes a statistically significant or clinically significant inhibition.

The phrase "inhibiting expression of a TTR" is intended to refer to inhibition of expression of any TTR gene (such as, e.g., a mouse TTR gene, a rat TTR gene, a monkey TTR gene, or a human TTR gene) as well as variants or mutants of a TTR gene. Thus, the TTR gene may be a wild-type TTR gene, a mutant TTR gene (such as a mutant TTR gene giving rise to amyloid deposition), or a transgenic TTR gene in the context of a genetically manipulated cell, group of cells, or organism.

"Inhibiting expression of a TTR gene" includes any level of inhibition of a TTR gene, e.g., at least partial suppression of the expression of a TTR gene. The expression of the TTR gene may be assessed based on the level, or the change in the level, of any variable associated with TTR gene expression, e.g., TTR mRNA level, TTR protein level, or the number or extent of amyloid deposits. This level may be assessed in an individual cell or in a group of cells, including, for example, a sample derived from a subject.

Inhibition may be assessed by a decrease in an absolute or relative level of one or more variables that are associated with TTR expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a TTR gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, at least about 99%%, or to below the level of detection of the assay. In some embodiments, the inhibition of expression of a TTRgene results in normalization of the level of the TTR gene such that the difference between the level before treatment and a normal control level is reduced by at least 30%, 35%, 40%, 45%, 50%, 55%, 60%, 65%, 70%, 75%, 80%, 85%, 90%, or 95%. In some embodiments, the inhibition is a clinically relevant inhibition.

Inhibition of the expression of a TTR gene may be manifested by a reduction of the amount of mRNA expressed by a first cell or group of cells (such cells may be present, for example, in a sample derived from a subject) in which a TTR gene is transcribed and which has or have been treated (e.g., by contacting the cell or cells with an RNAi agent of the invention, or by administering an RNAi agent of the invention to a subject in which the cells are or were present) such that the expression of a TTR gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a TTR gene may be assessed in terms of a reduction of a parameter that is functionally linked to TTR gene expression, e.g., TTR protein expression, retinol binding protein level, vitamin A level, or presence of amyloid deposits comprising TTR. TTR gene silencing may be determined in any cell expressing TTR, either constitutively or by genomic engineering, and by any assay known in the art. The liver is the major site of TTR expression. Other significant sites of expression include the choroid plexus, retina and pancreas.

Inhibition of the expression of a TTR protein may be manifested by a reduction in the level of the TTR protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a TTR gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of TTR mRNA that is expressed by a cell or group of cells, or the level of circulating TTR mRNA, may be determined using any method known in the art for assessing mRNA expression. In one embodiment, the level of expression of TTR in a sample is determined by detecting a transcribed polynucleotide, or portion thereof, e.g., mRNA of the TTR gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis. Circulating TTR mRNA may be detected using methods the described in PCT/US2012/043584, the entire contents of which are hereby incorporated herein by reference.

In one embodiment, the level of expression of TTR is determined using a nucleic acid probe. The term "probe", as used herein, refers to any molecule that is capable of selectively binding to a specific TTR. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to TTR mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of TTR mRNA.

An alternative method for determining the level of expression of TTR in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of TTR is determined by quantitative fluorogenic RT-PCR (i.e., the TaqMan™ System).

The expression levels of TTR mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of TTR expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of TTR protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

In some embodiments, the efficacy of the methods of the invention can be monitored by detecting or monitoring a reduction in an amyloid TTR deposit. Reducing an amyloid TTR deposit, as used herein, includes any decrease in the size, number, or severity of TTR deposits, or to a prevention or reduction in the formation of TTR deposits, within an organ or area of a subject, as may be assessed in vitro or in vivo using any method known in the art. For example, some methods of assessing amyloid deposits are described in Gertz, M. A. & Rajukumar, S. V. (Editors) (2010), *Amyloidosis: Diagnosis and Treatment*, New York: Humana Press. Methods of assessing amyloid deposits may include biochemical analyses, as well as visual or computerized assessment of amyloid deposits, as made visible, e.g., using immunohistochemical staining, fluorescent labeling, light microscopy, electron microscopy, fluorescence microscopy, or other types of microscopy. Invasive or noninvasive imaging modalities, including, e.g., CT, PET, or NMR/MRI imaging may be employed to assess amyloid deposits.

The methods of the invention may reduce TTR deposits in any number of tissues or regions of the body including but not limited to the heart, liver, spleen, esophagus, stomach, intestine (ileum, duodenum and colon), brain, sciatic nerve, dorsal root ganglion, kidney and retina.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organis. In certain embodiments, samples may be derived from the liver (e.g., whole liver or certain segments of liver or certain types of cells in the liver, such as, e.g., hepatocytes), the retina or parts of the retina (e.g., retinal pigment epithelium), the central nervous system or parts of the central nervous system (e.g., ventricles or choroid plexus), or the pancreas or certain cells or parts of the pancreas. In preferred embodiments, a "sample derived from a subject" refers to blood drawn from the subject or plasma derived therefrom. In further embodiments, a "sample derived from a subject" refers to liver tissue or retinal tissue derived from the subject.

In some embodiments of the methods of the invention, the RNAi agent is administered to a subject such that the RNAi agent is delivered to a specific site within the subject. The inhibition of expression of TTR may be assessed using measurements of the level or change in the level of TTR mRNA or TTR protein in a sample derived from fluid or tissue from the specific site within the subject. In preferred embodiments, the site is selected from the group consisting of liver, choroid plexus, retina, and pancreas. The site may also be a subsection or subgroup of cells from any one of the aforementioned sites (e.g., hepatocytes or retinal pigment epithelium). The site may also include cells that express a particular type of receptor (e.g., hepatocytes that express the asialogycloprotein receptor).

VIII. Methods for Treating or Preventing a TTR-Associated Disease

The present invention also provides methods for treating or preventing a TTR-associated disease in a subject. The methods include administering to the subject a therapeutically effective amount or prophylactically effective amount of an RNAi agent of the invention.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). A subject may include a transgenic organism.

In an embodiment, the subject is a human, such as a human being treated or assessed for a disease, disorder or condition that would benefit from reduction in TTR gene expression; a human at risk for a disease, disorder or condition that would benefit from reduction in TTR gene expression; a human having a disease, disorder or condition that would benefit from reduction in TTR gene expression; and/or human being treated for a disease, disorder or condition that would benefit from reduction in TTR gene expression, as described herein.

In some embodiments, the subject is suffering from a TTR-associated disease. In other embodiments, the subject is a subject at risk for developing a TTR-associated disease, e.g., a subject with a TTR gene mutation that is associated with the development of a TTR associated disease (e.g., before the onset of signs or symptoms suggesting the development of TTR amyloidosis), a subject with a family history of TTR-associated disease (e.g., before the onset of signs or symptoms suggesting the development of TTR amyloidosis), or a subject who has signs or symptoms suggesting the development of TTR amyloidosis.

A "TTR-associated disease," as used herein, includes any disease caused by or associated with the formation of amyloid deposits in which the fibril precursors consist of variant or wild-type TTR protein. Mutant and wild-type TTR give rise to various forms of amyloid deposition (amyloidosis). Amyloidosis involves the formation and aggregation of misfolded proteins, resulting in extracellular deposits that impair organ function. Clinical syndromes associated with TTR aggregation include, for example, senile systemic amyloidosis (SSA); systemic familial amyloidosis; familial amyloidotic polyneuropathy (FAP); familial amyloidotic cardiomyopathy (FAC); and leptomeningeal amyloidosis, also known as leptomeningeal or meningocerebrovascular amyloidosis, central nervous system (CNS) amyloidosis, or amyloidosis VII form.

In one embodiment, the RNAi agents of the invention are administered to subjects suffering from familial amyloidotic cardiomyopathy (FAC). In another embodiment, the RNAi agents of the invention are administered to subjects suffering from FAC with a mixed phenotype, i.e., a subject having both cardiac and neurological impairments. In yet another embodiment, the RNAi agents of the invention are administered to subjects suffering from FAP with a mixed phenotype, i.e., a subject having both neurological and cardiac impairments. In one embodiment, the RNAi agents of the invention are administered to subjects suffering from FAP that has been treated with an orthotopic liver transplantation (OLT). In another embodiment, the RNAi agents of the invention are administered to subjects suffering from senile systemic amyloidosis (SSA). In other embodiments of the methods of the invention, RNAi agents of the invention are administered to subjects suffering from familial amyloidotic cardiomyopathy (FAC) and senile systemic amyloidosis (SSA). Normal-sequence TTR causes cardiac amyloidosis in people who are elderly and is termed senile systemic amyloidosis (SSA) (also called senile cardiac amyloidosis (SCA) or cardiac amyloidosis). SSA often is accompanied by microscopic deposits in many other organs. TTR mutations accelerate the process of TTR amyloid formation and are the most important risk factor for the development of clinically significant TTR amyloidosis (also called ATTR (amyloidosis-transthyretin type)). More than 85 amyloidogenic TTR variants are known to cause systemic familial amyloidosis.

In some embodiments of the methods of the invention, RNAi agents of the invention are administered to subjects suffering from transthyretin (TTR)-related familial amyloidotic polyneuropathy (FAP). Such subjects may suffer from ocular manifestations, such as vitreous opacity and glaucoma. It is known to one of skill in the art that amyloidogenic transthyretin (ATTR) synthesized by retinal pigment epithelium (RPE) plays important roles in the progression of ocular amyloidosis. Previous studies have shown that panretinal laser photocoagulation, which reduced the RPE cells, prevented the progression of amyloid deposition in the vitreous, indicating that the effective suppression of ATTR expression in RPE may become a novel therapy for ocular amyloidosis (see, e.g., Kawaji, T., et al., Ophthalmology. (2010) 117: 552-555). The methods of the invention are useful for treatment of ocular manifestations of TTR related FAP, e.g., ocular amyloidosis. The RNAi agent can be delivered in a manner suitable for targeting a particular tissue, such as the eye. Modes of ocular delivery include retrobulbar, subcutaneous eyelid, subconjunctival, subtenon, anterior chamber or intravitreous injection (or internal injection or infusion). Specific formulations for ocular delivery include eye drops or ointments.

Another TTR-associated disease is hyperthyroxinemia, also known as "dystransthyretinemic hyperthyroxinemia" or "dysprealbuminemic hyperthyroxinemia". This type of hyperthyroxinemia may be secondary to an increased association of thyroxine with TTR due to a mutant TTR molecule with increased affinity for thyroxine. See, e.g., Moses et al. (1982) *J. Clin. Invest.*, 86, 2025-2033.

The RNAi agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof.

In preferred embodiments, the agents are administered to the subject subcutaneously. In some embodiments, a subject is administered a single dose of an RNAi agent via subcutaneous injection, e.g., abdominal, thigh, or upper arm injection. In other embodiments, a subject is administered a split dose of an RNAi agent via subcutaneous injection. In one embodiment, the split dose of the RNAi agent is administered to the subject via subcutaneous injection at two different anatomical locations on the subject. For example, the subject may be subcutaneously injected with a split dose of about 250 mg (e.g., about half of a 500 mg dose) in the right arm and about 250 mg in the left arm. In some embodiments of the invention, the subcutaneous administration is self-administration via, e.g., a pre-filled syringe or auto-injector syringe. In some embodiments, a dose of the RNAi agent for subcutaneous administration is contained in a volume of less than or equal to one ml of, e.g., a pharmaceutically acceptable carrier.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of TTR, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

In embodiments in which the RNAi agent is administered via a subcutaneous infusion pump, a single dose of the RNAi agent may be administered to the subject over a period of time of about 45 minutes to about 5 minutes, e.g., about 45 minutes, about 40 minutes, about 35 minutes, about 30 minutes, about 25 minutes, about 20 minutes, about 15 minutes, about 10 minutes, or about 5 minutes.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

In some embodiments, the RNAi agent is administered to a subject in an amount effective to inhibit TTR expression in a cell within the subject. The amount effective to inhibit TTR expression in a cell within a subject may be assessed using methods discussed above, including methods that involve assessment of the inhibition of TTR mRNA, TTR protein, or related variables, such as amyloid deposits.

In some embodiments, the RNAi agent is administered to a subject in a therapeutically or prophylactically effective amount.

"Therapeutically effective amount," as used herein, is intended to include the amount of an RNAi agent that, when administered to a patient for treating a TTR associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by TTR expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a TTR-associated disease, but who may be predisposed to the disease, is sufficient to prevent or ameliorate the disease or one or more symptoms of the disease. Symptoms that may be ameliorated include sensory neuropathy (e.g., paresthesia, hypesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi agents employed in the methods of the present invention may be administered in a sufficient amount to produce a reasonable benefit/risk ratio applicable to such treatment.

As used herein, the phrases "therapeutically effective amount" and "prophylactically effective amount" also include an amount that provides a benefit in the treatment, prevention, or management of pathological processes or symptom(s) of pathological processes mediated by TTR expression. Symptoms of TTR amyloidosis include sensory neuropathy (e.g. paresthesia, hypesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy.

In one embodiment, for example, when the subject has FAP, FAP with mixed phenotype, FAC with mixed phenotype, or FAP and has had an OLT, treatment of the subject with a dsRNA agent of the invention slows the progression of neuropathy. In another embodiment, for example, when the subject has FAP, FAP with mixed phenotype, FAC with mixed phenotype, SSA, or FAP and has had an OLT, treatment of the subject with a dsRNA agent of the invention slows the progression of neuropathy and cardiomyopathy.

For example, in one embodiment, the methods of the invention slow, reduce or arrest neurological impairment. Any suitable measure of neurological impairment can be used to determine whether a subject has reduced, slowed, or arrested neurological impairment.

One suitable measure is a Neuropathy Impairment Score (NIS). NIS refers to a scoring system that measures weakness, sensation, and reflexes, especially with respect to peripheral neuropathy. The NIS score evaluates a standard group of muscles for weakness (1 is 25% weak, 2 is 50% weak, 3 is 75% weak, 3.25 is movement against gravity, 3.5 is movement with gravity eliminated, 3.75 is muscle flicker without movement, and 4 is paralyzed), a standard group of muscle stretch reflexes (0 is normal, 1 is decreased, 2 is absent), and touch-pressure, vibration, joint position and motion, and pinprick (all graded on index finger and big toe: 0 is normal, 1 is decreased, 2 is absent). Evaluations are corrected for age, gender, and physical fitness.

In one embodiment, the methods of the invention reduce a NIS by at least 10%. In other embodiments, the methods of the invention result in a reduction of NIS by at least 5, 10, 15, 20, 25, 30, 40, or by at least 50%. In other embodiments, the methods arrest an increasing NIS score, e.g., the method results in a 0% increase of the NIS score. In yet other embodiments, the methods of the invention slow the rate at which an NIS score increase, e.g., the rate of increase of an NIS score in a subject treated with an RNAi agent of the invention as compared to the rate of increase of an NIS score in a subject that is not treated with an RNAi agent of the invention.

Methods for determining an NIS in a human subject are well known to one of skill in the art and can be found in, for example, Dyck, P J et al., (1997) *Neurology* 1997. 49(1): pgs. 229-239); Dyck P J. (1988) *Muscle Nerve*. January; 11(1):21-32.

Another suitable measurement of neurological impairment is a Modified Neuropathy Impairment Score (mNIS+7). As known to one of ordinary skill in the art, mNIS+7 refers to a clinical exam-based assessment of neurologic impairment (NIS) combined with electrophysiologic measures of small and large nerve fiber function (NCS and QST), and measurement of autonomic function (postural blood pressure). The mNIS+7 score is a modification of the NIS+7 score (which represents NIS plus seven tests). NIS+7 analyzes weakness and muscle stretch reflexes. Five of the seven tests include attributes of nerve conduction. These attributes are the peroneal nerve compound muscle action potential amplitude, motor nerve conduction velocity and motor nerve distal latency (MNDL), tibial MNDL, and sural sensory nerve action potential amplitudes. These values are corrected for variables of age, gender, height, and weight. The remaining two of the seven tests include vibratory detection threshold and heart rate decrease with deep breathing.

The mNIS+7 score modifies NIS+7 to take into account the use of Smart Somatotopic Quantitative Sensation Testing, new autonomic assessments, and the use of compound muscle action potential of amplitudes of the ulnar, peroneal, and tibial nerves, and sensory nerve action potentials of the ulnar and sural nerves (Suanprasert, N. et al., (2014) *J. Neurol. Sci.,* 344(1-2): pgs. 121-128).

In one embodiment, the methods of the invention reduce an mNIS+7 by at least 10%. In other embodiments, the methods of the invention result in a reduction of an mNIS+7 score by at least 5, 10, 15, 20, 25, 30, 40, or by at least 50%. In other embodiments, the methods arrest an increasing mNIS+7, e.g., the method results in a 0% increase of the mNIS+7. In yet other embodiments, the methods of the invention slow the rate at which an NIS+7 score increase, e.g., the rate of increase of an NIS+7 score in a subject treated with an RNAi agent of the invention as compared to the rate of increase of an NIS+7 score in a subject that is not treated with an RNAi agent of the invention.

The therapeutic and prophylactic methods of the present invention may also improve other clinical parameters, such a walking ability, in the subject being treated. For example, during or following a treatment period a subject may have an increased exercise capacity or activity.

Any suitable measure of exercise capacity can be used to determine whether a subject has an increased exercise capacity or activity. One suitable measure is a 6-minute walk test (6MWT), which measures how far the subject can walk in 6 minutes, i.e., the 6-minute walk distance (6MWD). In one embodiment, the methods of the invention provide to the subject an increase from baseline in the 6MWD by at least about 10 minutes, e.g., about 10, 15, 20, or about 30 minutes.

A therapeutically effective amount and prophylactically effective amount of an RNAi agent of the invention also includes an amount that improves one or more quality of life parameters versus baseline, for example an increase in score on at least one of the SF-36® health survey functional scales; and/or an increased longevity; and/or decreased hospitalization.

Any suitable measure quality of life may be used. For example, the SF-36® health survey provides a self-reporting, multi-item scale measuring eight health parameters: physical functioning, role limitations due to physical health problems, bodily pain, general health, vitality (energy and fatigue), social functioning, role limitations due to emotional problems, and mental health (psychological distress and psychological well-being). The survey also provides a physical component summary and a mental component summary. In one embodiment, the methods of the invention provide to the subject an improvement versus baseline in at least one of the SF-36 physical health related parameters (physical health, role-physical, bodily pain and/or general health) and/or in at least one of the SF-36 mental health related parameters (vitality, social functioning, role-emotional and/or mental health). Such an improvement can take the form of an increase of at least 1, for example at least 2 or at least 3 points, on the scale for any one or more parameters.

The methods of the present invention may also improve the prognosis of the subject being treated. For example, the methods of the invention may provide to the subject a reduction in probability of a clinical worsening event during the treatment period.

The dose of an RNAi agent that is administered to a subject may be tailored to balance the risks and benefits of a particular dose, for example, to achieve a desired level of TTR gene suppression (as assessed, e.g., based on TTR mRNA suppression, TTR protein expression, or a reduction in an amyloid deposit, as defined above) or a desired therapeutic or prophylactic effect, while at the same time avoiding undesirable side effects.

In one embodiment, an iRNA agent of the invention is administered to a subject as a weight-based dose. A "weight-based dose" (e.g., a dose in mg/kg) is a dose of the iRNA agent that will change depending on the subject's weight. In another embodiment, an iRNA agent is administered to a subject as a fixed dose. A "fixed dose" (e.g., a dose in mg) means that one dose of an iRNA agent is used for all subjects regardless of any specific subject-related factors, such as weight. In one particular embodiment, a fixed dose of an iRNA agent of the invention is based on a predetermined weight or age.

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.25 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 10 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In some embodiments, for example, when a composition of the invention comprises a dsRNA as described herein and an N-acetylgalactosamine, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.15 mg/kg to about 3 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 3 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 0.6 mg/kg to about 3 mg/kg, about 1 mg/kg to about 3 mg/kg, about 1 mg/kg to about 5 mg/kg, about 1 mg/kg to about 10 mg/kg, about 1.25 mg/kg to about 3 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, about 9.5 mg/kg to about 10 mg/kg. Values and ranges intermediate to the recited values are also intended to be part of this invention.

For example, the dsRNA may be administered at a dose of about 0.1, 0.15, 0.2, 0.3, 0.4, 0.5, 0.6, 0.7, 0.8, 0.9, 1, 1.1, 1.2, 1.25, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.25, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In some embodiments, the RNAi agent is administered as a fixed dose of between about 25 mg to about 900 mg, e.g., between about 25 mg to about 850 mg, between about 25 mg to about 800 mg, between about 25 mg to about 750 mg, between about 25 mg to about 700 mg, between about 25 mg to about 650 mg, between about 25 mg to about 600 mg, between about 25 mg to about 550 mg, between about 25 mg to about 500 mg, between about 100 mg to about 850 mg, between about 100 mg to about 800 mg, between about 100 mg to about 750 mg, between about 100 mg to about 700 mg, between about 100 mg to about 650 mg, between about 100 mg to about 600 mg, between about 100 mg to about 550 mg, between about 100 mg to about 500 mg, between about 200 mg to about 850 mg, between about 200 mg to about 800 mg, between about 200 mg to about 750 mg, between about 200 mg to about 700 mg, between about 200 mg to about 650 mg, between about 200 mg to about 600 mg, between about 200 mg to about 550 mg, between about 200 mg to about 500 mg, between about 300 mg to about 850 mg, between about 300 mg to about 800 mg, between about 300 mg to about 750 mg, between about 300 mg to about 700 mg, between about 300 mg to about 650 mg, between about 300 mg to about 600 mg, between about 300 mg to about 550 mg, between about 300 mg to about 500 mg, between about 400 mg to about 850 mg, between about 400 mg to about 800 mg, between about 400 mg to about 750 mg, between about 400 mg to about 700 mg, between about 400 mg to about 650 mg, between about 400 mg to about 600 mg, between about 400 mg to about 550 mg, or between about 400 mg to about 500 mg.

In some embodiments, the RNAi agent is administered as a fixed dose of about 12.5 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 125 mg, about 130 mg, about 140 mg, about 150 mg, about 160 mg, about 170 mg, about 175 mg, about 180 mg, about 190 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg.

In certain embodiments, the RNAi agent is administered to a subject as a fixed dose of about 20, 25, 50, 75, 100, 125, 150, 175, 200, 225, 250, 275, 300, 325, 350, 375, 400, 425, 450, 475, 500, 525, 550, 575, or about 600 mg once every three months (i.e., once a quarter). In one embodiment, the administration is subcutaneous administration, e.g., self-administration via, e.g., a pre-filled syringe or auto-injector syringe. In some embodiments, a dose of the RNAi agent for subcutaneous administration is contained in a volume of less than or equal to one ml of, e.g., a pharmaceutically acceptable carrier.

In some embodiments, the RNAi agent is administered in two or more doses. If desired to facilitate repeated or frequent infusions, implantation of a delivery device, e.g., a pump, semi-permanent stent (e.g., intravenous, intraperitoneal, intracisternal or intracapsular), or reservoir may be advisable. In some embodiments, the number or amount of subsequent doses is dependent on the achievement of a desired effect, e.g., the suppression of a TTR gene, or the achievement of a therapeutic or prophylactic effect, e.g., reducing an amyloid deposit or reducing a symptom of a TTR-associated disease.

In some embodiments, the RNAi agent is administered according to a schedule. For example, the RNAi agent may be administered twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, monthly, or quarterly. In one embodiment, a dosage of 0.3 mg/kg, 0.6 mg/kg, 1 mg/kg, 1.25 mg/kg, 1.5 mg/kg, 2, 2.5 mg/kg, or 3 mg/kg is administered monthly. In another embodiment, a dosage of 0.3 mg/kg, 0.6 mg/kg, 1 mg/kg, 1.25 mg/kg, 1.5 mg/kg, 2.2.5 mg/kg, or 3 mg/kg is administered quarterly.

In other embodiments, the schedule involves closely spaced administrations followed by a longer period of time during which the agent is not administered. For example, the schedule may involve an initial set of doses that are administered in a relatively short period of time (e.g., about every 6 hours, about every 12 hours, about every 24 hours, about every 48 hours, or about every 72 hours) followed by a longer time period (e.g., about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks) during which the RNAi agent is not administered. In one embodiment, the RNAi agent is initially administered hourly and is later administered at a longer interval (e.g., daily, weekly, biweekly, monthly, or quarterly). In another embodiment, the RNAi agent is initially administered daily and is later administered at a longer interval (e.g., weekly, biweekly, monthly, or quarterly). In certain embodiments, the longer interval increases over time or is determined based on the achievement of a desired effect.

In a specific embodiment, the RNAi agent is administered once daily during a first week, followed by weekly, monthly or quarterly dosing starting on the eighth day of administration. In another specific embodiment, the RNAi agent is administered every other day during a first week followed by weekly, monthly or quarterly dosing starting on the eighth day of administration. In another embodiment, the RNAi agent is administered once daily for five days during a first week, followed by weekly, monthly or quarterly dosing administration.

Any of these schedules may optionally be repeated for one or more iterations. The number of iterations may depend on the achievement of a desired effect, e.g., the suppression of a TTR gene, retinol binding protein level, vitamin A level, and/or the achievement of a therapeutic or prophylactic effect, e.g., reducing an amyloid deposit or reducing a symptom of a TTR-associated disease.

In some embodiments, the RNAi agent is administered with other therapeutic agents or other therapeutic regimens. For example, other agents or other therapeutic regimens suitable for treating a TTR-associated disease may include a liver transplant, which can reduce mutant TTR levels in the body; Tafamidis (Vyndaqel), which kinetically stabilizes the TTR tetramer preventing tetramer dissociation required for TTR amyloidogenesis; and diuretics, which may be employed, for example, to reduce edema in TTR amyloidosis with cardiac involvement.

In one embodiment, a subject is administered an initial dose and one or more maintenance doses of an RNAi agent. The maintenance dose or doses can be the same or lower than the initial dose, e.g., one-half of the initial dose. A maintenance regimen can include treating the subject with a dose or doses ranging from 0.01 µg to 15 mg/kg of body weight per day, e.g., 1 mg/kg, 1.25 mg/kg, 1.5 mg/kg, 2 mg/kg, 2.5 mg/kg, 3 mg/kg, 4 mg/kg, 5 mg/kg, 10 mg/kg, 0.1 mg/kg, 0.15 mg/kg, 0.3 mg/kg, 0.6 mg/kg, 0.01 mg/kg, 0.001 mg/kg, or 0.00001 mg/kg of bodyweight per day, or a dose or doses of about 12.5 mg to about 900 mg, e.g., about 25 mg, about 30 mg about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg per week. The maintenance doses are, for example, administered no more than once every 2 days, once every 5 days, once every 7 days, once every 10 days, once every 14 days, once every 21 days, once every 30 days, or once every 90 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once every 5 or 8 days. Following treatment, the patient can be monitored for changes in his/her condition. The dosage of the RNAi agent may either be increased in the event the patient does not respond significantly to current dosage levels, or the dose may be decreased if an alleviation of the symptoms of the disease state is observed, if the disease state has been ablated, or if undesired side-effects are observed.

VI. Kits

The present invention also provides kits for performing any of the methods of the invention. Such kits include one or more RNAi agent(s) and instructions for use, e.g., instructions for inhibiting expression of a TTR in a cell by contacting the cell with the RNAi agent(s) in an amount effective to inhibit expression of the TTR. The kits may optionally further comprise means for contacting the cell with the RNAi agent (e.g., an injection device or an infusion pump), or means for measuring the inhibition of TTR (e.g., means for measuring the inhibition of TTR mRNA or TTR protein). Such means for measuring the inhibition of TTR may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Suitable RNAi agents for inclusion in the kits of the invention include any one of the RNAi agents listed in any one of Tables 1, 3, 5, 6, or 7. In one embodiment, the RNAi agent is selected from the group consisting of AD-66016, AD-65492, AD-66017, and AD-66018.

The RNAi agent may be provided in any convenient form, such as a solution in sterile water for injection. For example, the RNAi agent may be provided as a 500 mg/ml, 450 mg/ml, 400 mg/ml, 350 mg/ml, 300 mg/ml, 250 mg/ml, 200 mg/ml, 150 mg/ml, 100 mg/ml, or 50 mg/ml solution in sterile water for injection.

This invention is further illustrated by the following examples which should not be construed as limiting. The contents of all references and published patents and patent applications cited throughout the application are hereby incorporated herein by reference.

EXAMPLES

Example 1: In Vitro Stability and Silencing Activity of Chemically Modified RNAI Agents that Target TTR The following experiments demonstrated the beneficial effects of certain chemical modifications, including no more than 8 2'-fluoro modifications on the sense strand, no more than 6 2'-fluoro modifications on the antisense strand, six phosphorothioate nucleotide linkages, and a ligand, e.g., a GalNAc$_3$ ligand, on the silencing activity of RNAi agents that target TTR. The sequences of the agents investigated are provided in Table 1 below.

TTR siRNA sequences were synthesized at a 1 μmol scale on a Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, Wis.) and Hongene (China). 2'F, 2'-O-Methyl, GNA (glycol nucleic acids), 5'phosphate and abasic modifications were introduced employing the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 minutes employing 5-Ethylthio-1H-tetrazole (ETT) as the activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, Mass., USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 μL Aqueous Methylamine reagents at 60° C. for 20 minutes. At the end of cleavage and deprotection step, the synthesis plate was allowed to come to room temperature and was precipitated by addition of 1 mL of acetontile:ethanol mixture (9:1). The plates were cooled at −80 C for 2 hrs, supernatant decanted carefully with the aid of a multi channel pipette. The oligonucleotide pellet was re-suspended in 20 mM NaOAc buffer and was desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples was analysed by IEX chromatography to determine purity.

Annealing of TTR single strands was performed on a Tecan liquid handling robot. Equimolar mixtures of sense and antisense single strands were combined and annealed in 96 well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 μM in 1×PBS.

These duplexes were assayed for in vitro metabolic stability using a rat cytosol stability assay. For such an assay, female rat liver cytosol (Xenotech Cat. # R1500.C) was thawed to room temperature and diluted to 1 mg/mL in 50 mM Tris buffer: HCl pH 7.4, 5 mM MgCl2. Twenty-four hour samples were prepared by mixing 100 μL of 1 mg/mL Cytosol with 25 μL of 0.4 mg/mL siRNA sample in a microcentrifuge tube and incubating for 24 hours in an eppendorf Thermomixer set to 37° C. and 300 rpm. After 24 hours of incubation 300 μL of Phenomenex Lysis Loading Buffer (Cat. # ALO-8498) and 12.5 μL of a 0.4 mg/mL internal standard siRNA were added to each sample. Zero hour samples were prepared by mixing 100 μL of 1 mg/mL Cytosol with 25 μL of 0.4 mg/mL siRNA sample, 300 μL of Phenomenex Lysis Loading Buffer, and 12.5 μL of a 0.4 mg/mL internal standard siRNA. siRNA was extracted from 24 hour samples and 0 hour samples using a Phenomenex Clarity OTX Starter Kit (Cat. # KSO-8494). After the samples were extracted they were transferred to a microcentrifuge tube and dried down using a Labconco CentriVap Concentrator (Cat. #7810010). The samples were then resuspended with 500 μL of nuclease free water. Fifty μL of each sample was run on an Agilent Technologies 1260 Infinity Binary LC with Agilent Technologies 6130 Quadrupole LC/MS. The analysis was run using double column setup in regeneration mode. The Quaternary pump method was run for 12.20 minutes at 0.400 mL/min with the following timetable:

| Time Function | Parameter |
|---|---|
| 0.20 | 5% Buffer A(16 mM TEA 200 mM HFIP), 95% Buffer B (100% Methanol) |
| 2.50 | 5% Buffer A(16 mM TEA 200 mM HFIP), 95% Buffer B (100% Methanol) |
| 3.00 | 100% Buffer A(16 mM TEA 200 mM HFIP) |

The Binary Pump method was run for 12.20 min at 0.700 mL/min with the following timetable:
Time FunctionParameter

| Time Function | Parameter |
|---|---|
| 0.00 | 100% Buffer A(16 mM TEA 200 mM HFIP) |
| 0.40 | 100% Buffer A(16 mM TEA 200 mM HFIP) |
| 10.00 | 60% Buffer A(16 mM TEA 200 mM HFIP), 40% Buffer B (100% ACN) |
| 10.10 | 100% Buffer A(16 mM TEA 200 mM HFIP) |
| 12.20 | 100% Buffer A(16 mM TEA 200 mM HFIP) |

Both the left and right column was set at 75.00° C. The UV signal was measured at 260 nm wavelength. The percent remaining of each strand was calculated using the following equation:

% Strand remaining=100*(Peak Area$_{Strand\ 24\ h}$/Peak Area$_{Strand\ 0\ h}$*(Peak Area$_{Standard\ 24\ h}$/Peak Area$_{Standard\ 0\ h}$)).

The results of these twenty-four hour cytosol stability assays demonstrate that all of the duplexes are highly stable.

A subset of these agents was also assessed for in vitro metabolic stability using a tritosome stability assay. For the tritosome stability assays, rat liver tritosomes (Xenotech custom product PR14044) were thawed to room temperature and diluted to 0.5 units/mL Acid Phosphatase in 20 mM Sodium Citrate pH 5.0 Buffer. Twenty-four hour samples were prepared by mixing 100 μL of 0.5 units/mL Acid Phosphatase Tritosomes with 25 μL of 0.4 mg/mL siRNA sample in a microcentrifuge tube and incubating for twenty-four hours in an eppendorf Thermomixer set to 37° C. and 300 rpm. After twenty-four hours of incubation, 300 μL of Phenomenex Lysis Loading Buffer (Cat. # ALO-8498) and 12.5 μL of a 0.4 mg/mL internal standard siRNA were added to each sample. Time 0 hour samples were prepared by mixing 100 μL of 0.5 units/mL Acid Phosphatase Tritosomes with 25 μL of 0.4 mg/mL siRNA sample, 300 μL of Phenomenex Lysis Loading Buffer, and 12.5 μL of a 0.4 mg/mL internal standard siRNA. siRNA was extracted from twenty-four hour samples and 0 hour samples using a Phenomenex Clarity OTX Starter Kit (Cat. # KSO-8494).

After the samples were extracted, they were transferred to a microcentrifuge tube and dried down using a Labconco CentriVap Concentrator (Cat. #7810010). The samples were then resuspended with 500 µL of nuclease free water. Fifty µL of each sample was run on an Agilent Technologies 1260 Infinity Binary LC with Agilent Technologies 6130 Quadrupole LC/MS. The analysis was run using double column setup in regeneration mode. The Quaternary pump method was run for 12.20 minutes at 0.400 mL/min with the following timetable:

| Time Function | Parameter |
|---|---|
| 0.20 | 5% Buffer A(16 mM TEA 200 mM HFIP), 95% Buffer B (100% Methanol) |
| 2.50 | 5% Buffer A(16 mM TEA 200 mM HFIP), 95% Buffer B (100% Methanol) |
| 3.00 | 100% Buffer A(16 mM TEA 200 mM HFIP) |

The Binary Pump method was run for 12.20 min at 0.700 mL/min with the following timetable:

| Time Function | Parameter |
|---|---|
| 0.00 | 100% Buffer A(16 mM TEA 200 mM HFIP) |
| 0.40 | 100% Buffer A(16 mM TEA 200 mM HFIP) |
| 10.00 | 60% Buffer A(16 mM TEA 200 mM HFIP), 40% Buffer B (100% ACN) |
| 10.10 | 100% Buffer A(16 mM TEA 200 mM HFIP) |
| 12.20 | 100% Buffer A(16 mM TEA 200 mM HFIP) |

Both the left and right column was set at 75.00° C. The UV signal was measured at 260 nm wavelength. The percent remaining of each strand was calculated using the following equation:

$$\% \text{ Strand remaining} = 100 * (\text{Peak Area}_{Strand\ 24\ h} / \text{Peak Area}_{Strand\ 0\ h} * (\text{Peak Area}_{Standard\ 24\ h} / \text{Peak Area}_{Standard\ 0\ h})).$$

The results of the twenty-four hour tritosome stability assays, provided in FIG. 1, demonstrate that all of the duplexes are highly stable in tritosomes.

TABLE 1

Modified Sense and Antisense Strand Sequences of TTR dsRNAs

| Duplex ID | Sense ID | Sense sequence 5' to 3' | SEQ ID NO | Antisense ID |
|---|---|---|---|---|
| AD-51547 | A-106305 | UfgGfgAfuUfuCfAfUfgUfaacCfaAfgAfL96 | 15 | A-102978 |
| AD-58142 | A-117240 | UfsgsGfgAfuUfuCfAfUfgUfaacCfaAfgAfL96 | 16 | A-117241 |
| AD-64527 | A-128512 | usgsggauuucadTguaacaaagaL96 | 17 | A-128525 |
| AD-65367 | A-128499 | usgsggAfuUfuCfAfUfgUfaaccaagAfL96 | 18 | A-128520 |
| AD-65489 | A-131365 | usgggauuucadTguaacaaagaL96 | 19 | A-128520 |
| AD-65481 | A-131354 | usgsggauUfuCfAfUfguaaccaagaL96 | 20 | A-131364 |
| AD-65488 | A-131354 | usgsggauUfuCfAfUfguaaccaagaL96 | 21 | A-131358 |
| AD-65496 | A-131354 | usgsggauUfuCfAfUfguaaccaagaL96 | 22 | A-131360 |
| AD-65491 | A-128557 | usgsggauuucadTguaacY34aagaL96 | 23 | A-128525 |
| AD-65495 | A-131353 | usgsggauUfuCfAfUfguaaCfcaagaL96 | 24 | A-128516 |
| AD-65367 | A-128499 | usgsggAfuUfuCfAfUfgUfaaccaagAfL96 | 25 | A-128520 |
| AD-65493 | A-128512 | usgsggauuucadTguaacaaagaL96 | 26 | A-131366 |
| AD-65494 | A-128512 | usgsggauuucadTguaacaaagaL96 | 27 | A-128526 |
| AD-64527 | A-128512 | usgsggauuucadTguaacaaagaL96 | 28 | A-128525 |

| Duplex ID | Antisense sequence 5' to 3' | SEQ ID NO |
|---|---|---|
| AD-51547 | uCfuUfgGfUfUfaCfaugAfaAfuCfcCfasUfsc | 29 |
| AD-58142 | usCfsuUfgGfUfUfaCfaugAfaAfuCfcCfasusc | 30 |
| AD-64527 | usdCsuuggUuadCaugdAaaucccasusc | 31 |
| AD-65367 | usCfsuugguuacaugAfaaucccasusc | 32 |
| AD-65489 | usCfsuugguuacaugAfaaucccasusc | 33 |
| AD-65481 | UfsCfsuugGfuuacaugAfaAfucccasusc | 34 |
| AD-65488 | PusCfsuugGfuuacaugAfaAfucccasusc | 35 |

TABLE 1-continued

Modified Sense and Antisense Strand Sequences of TTR dsRNAs

| | | |
|---|---|---|
| AD-65496 | PusCfsuugGfuuAfcaugAfaAfucccasusc | 36 |
| AD-65491 | usdCsuugguuadCaugdAaaucccasusc | 37 |
| AD-65495 | usCfsuugGfuUfAfcaugAfaAfucccasusc | 38 |
| AD-65367 | usCfsuugguuacaugAfaaucccasusc | 39 |
| AD-65493 | PusCfsuugguuacaugAfaaucccasusc | 40 |
| AD-65494 | PusdCsuugguuadCaugdAaaucccasusc | 41 |
| AD-64527 | usdCsuugguuadCaugdAaaucccasusc | 42 |

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methylthymine-3'-phosphate |
| ts | 2'-O-methyl-5-methylthymine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| dA | deoxy-adenosine |
| dC | deoxy-cytodine |
| dG | deoxy-guanosine |
| (dT) | 2'-deoxythymidine-3'-phosphate |
| Y34 | 2-hydroxymethyl-tetrahydrofurane-4-methoxy-3-phosphate (abasic 2'-OMe furanose) |
| Y44 | 2-hydroxymethyl-tetrahydrofurane-5-phosphate |
| (Cgn) | Cytidine-glycol nucleic acid (GNA) |
| P | Phosphate |
| VP | Vinyl-phosphate |

An additional set of agents targeting TTR were designed and synthesized. The sequences of these agents are provided in Table 3, below.

These additional agents were evaluated in in vitro assays. In particular, the $IC_{50}$ for each iRNA agent was determined in Hep3B cells (a human hepatoma cell line) or primary cynomologous hepatocytes (Life Technologies) by standard reverse transfection using Lipofectamine RNAiMAX. Hep3b cells were cultured in EMEM with 10% FBS, while primary cynomologous hepatocytes were thawed immediately prior to use and cultured in WMEM with 10% FBS. Reverse transfection was carried out by adding 5 µL of RNA duplex per well into a 384-well plate along with 4.9 µL of Opti-MEM plus 0.1 µL of Lipofectamine RNAiMax per well (Invitrogen, Carlsbad Calif. cat #13778-150) and incubating at room temperature for 15-20 minutes. Following incubation, 40 µL of complete growth media without antibiotic containing 5,000 Hep3B cells or primary cynomologous hepatocytes was then added to each well. Collagen-coated plates were used for the primary hepatocytes. Cells were incubated for 24 hours at 37° C. in an atmosphere of 5% $CO_2$ prior to lysis and analysis of TTR and GAPDH mRNA by RT-qPCR. Eight different siRNA concentrations ranging from 10 nM to 0.38 fM were assessed for $IC_{50}$ determination and TTR/GAPDH for siRNA transfected cells was normalized to cells transfected with 10 nM Luciferase siRNA.

Free uptake silencing in primary cynomolgus hepatocytes was assessed following incubation with TTR siRNA for 24 hours. The method was similar to that described above, with the exception that 5 µL complete growth medium was substituted for the 5 µL containing Lipofectamine RNAiMax and Optimem. Downstream analysis for TTR and GAPDH mRNA was performed as described above. For a typical dose response curve, siRNAs were titrated from 500 nM to 0.1.8 pM by eight-point 6-fold serial dilution.

The results of these assays (provided in Table 4) demonstrate that all of the duplexes potently inhibit TTR mRNA expression.

The in vitro stability of these additional agents was also assessed using the cytosol and tritosome stability assays described above.

Figure 2A:
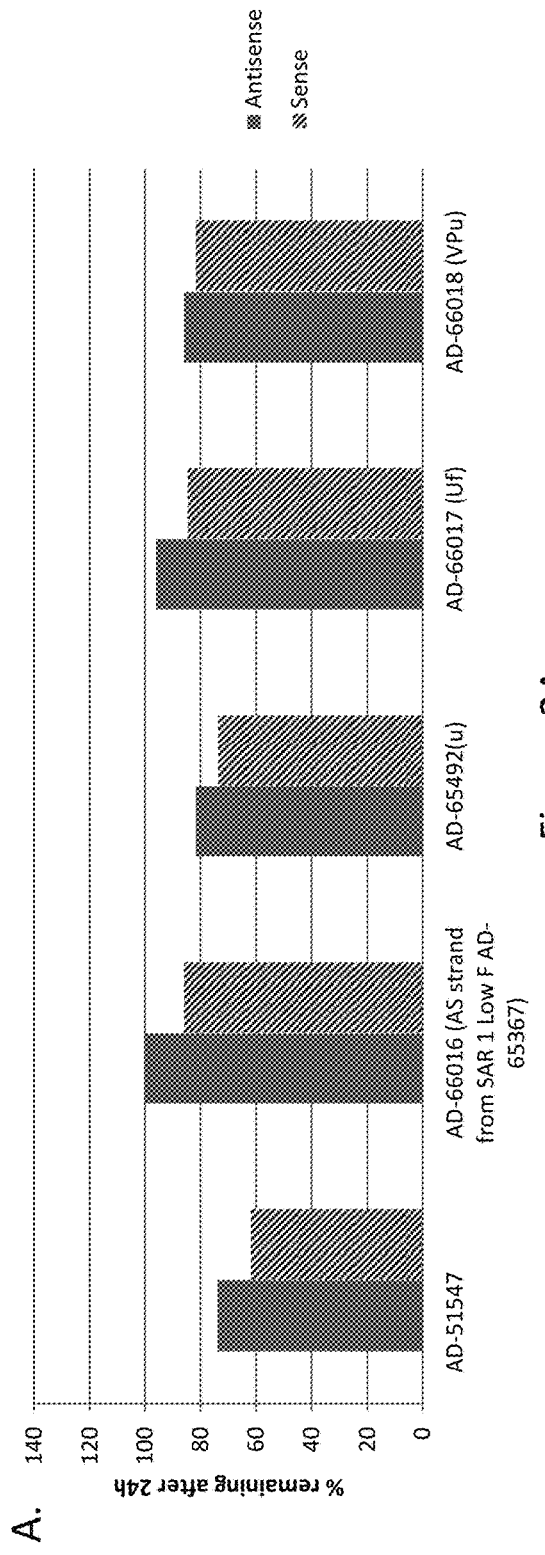
FIG. 2A is a graph depicting the stability of the indicated RNAi agents in a twenty-four hour rat cytosol stability assay and FIG. 2B is a graph depicting the stability of the indicated RNAi agents in a twenty-four hour tristosome stability assay.
Figure 2B:
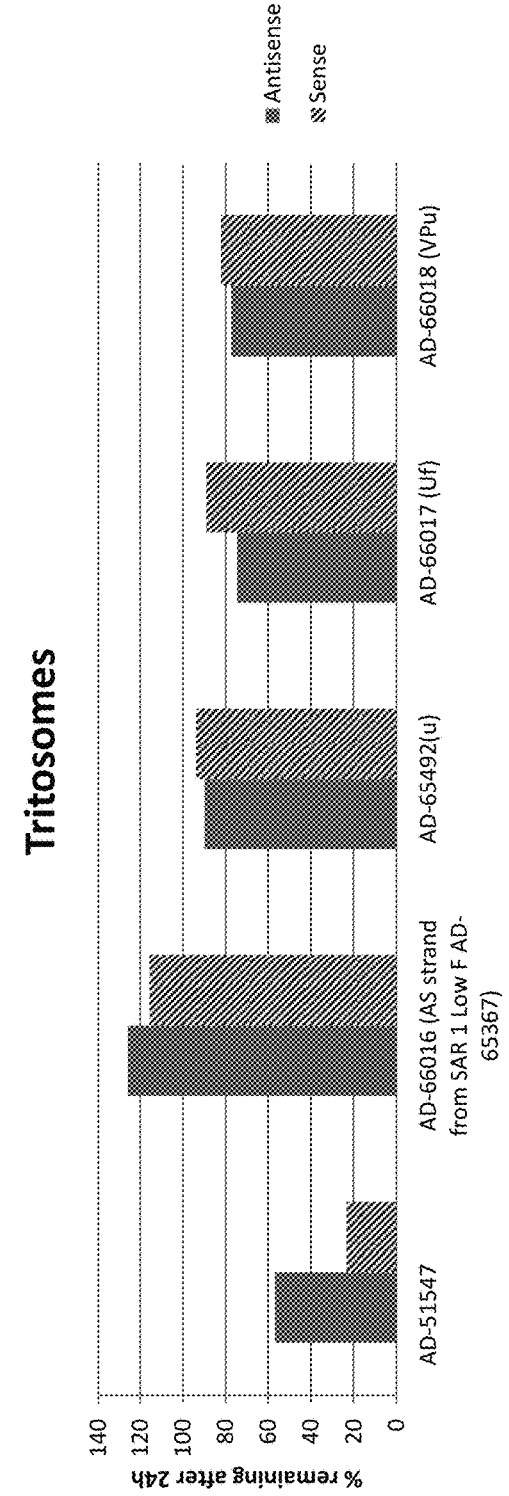

The results of the twenty-four hour cytosol stability assay are provided in FIG. 2A and the results of the twenty-four hour tritosome stability assay are provided in FIG. 2B and demonstrate that all of the duplexes are highly stable in tritosomes and rat cytosol.

TABLE 3

Modified Sense and Antisense Strand Sequences of TTR dsRNAs

| Duplex ID | Sense ID | Sense sequence 5' to 3' | SEQ ID NO | Antisense ID | Antisense sequence 5' to 3' | SEQ ID NO |
|---|---|---|---|---|---|---|
| AD-66016 | A-131354 | usgsggauUfuCfAfUfguaaccaagaL96 | 43 or 10 | A-128520 | usCfsuugguuacaugAfaaucccasusc | 47 or 6 |
| AD-65492 | A-131354 | usgsggauUfuCfAfUfguaaccaagaL96 | 44 or 10 | A-131359 | usCfsuugGfuuAfcaugAfaAfucccasusc | 48 or 7 |
| AD-66017 | A-131354 | usgsggauUfuCfAfUfguaaccaagaL96 | 45 or 10 | A-131903 | UfsCfsuugGfuuAfcaugAfaAfucccasusc | 49 or 8 |
| AD-66018 | A-131354 | usgsggauUfuCfAfUfguaaccaagaL96 | 46 or 10 | A-131902 | VPusCfsuugGfuuAfcaugAfaAfucccasusc | 50 or 9 |

TABLE 4

In vitro Activity of Additional TTR RNAi Agents

| IC50 (nM) | AD-66016 (65367 AS) | | AD-65492 (u) | | AD-66017 (Uf) | | AD-66018 (VPu) | |
|---|---|---|---|---|---|---|---|---|
| | Transfection | Free Uptake | Transfection | Free Uptake | Transfection | Free Uptake | Transfection | Free Uptake |
| Hep3b | 0.931 | N/A | 0.722 | N/A | 0.108 | N/A | 0.053 | N/A |
| Cyno Hepatocytes | 0.235 | 5.157 | 0.21 | 3.629 | 0.026 | 0.284 | 0.015 | 0.191 |

Example 2. In Vivo TTR Silencing

The in vivo efficacy of the additional agents described above was assessed in transgenic mice that express the valine 30 methionine variant of human TTR (V30M hTTR) (see, e.g., Nagata, et al. (1995) *J Biochem.* 117:169-175; Kohno, et al. (1997) *Am J Pathol.* 150(4):1497-508). The V30M variant of TTR is known to cause familial amyloid polyneuropathy type I in humans. See, e.g., Lobato, L. (2003) *J Nephrol.*, 16(3):438-42.

Eleven- to thirteen-month old TTR V30m mice were subcutaneously administered a single 1 mg/kg or 2.5 mg/kg dose of the agents and the level of TTR was determined in the serum of the animals pre-dose and at days 3, 7, 10, 14, 21, 28, 35, 42, 56, 70 and 84 post-dose. Briefly, TTR levels were assayed using a validated TTR enzyme-linked immunosorbent assay (ELISA) (see, e.g., Coelho, et al. (2013) *N Engl J Med* 369:819). Ninety-six-well immuno-microplates were coated at 4° with rabbit anti-human TTR pAb (Abcam) 24 hours prior to the start of the TTR Serum Protein ELISA assay. On the day of assay, plates were washed in TBS-T, and blocked in 1× Powerblock (Biogenex) for 2 hours at room temperature. Serum samples were diluted 15,000 fold in 1× Powerblock. A 12-point human TTR standard curve employing a human TTR protein standard (Sigma-Aldrich, P1742), was generated using 1.6× serial dilutions, ranging from 250 to 0 ng/mL. Following the block, 100 µL volumes of standards and samples were added to the plate and allowed to incubate for 2 hours at room temperature. Plates were washed in TBS-T, and incubated for 1 hour at room temperature with Sheep Anti-hTTR primary antibody (AbCam) diluted 1:2500 in 1× Powerblock. After a TBS-T wash, plates were incubated for 1 hour at room temperature with Donkey anti-sheep-Alkaline phosphatase secondary antibody (AbCam) diluted 3:10000 in 1× Powerblock. Plates were washed in TBS-T and 100 µL volume of prepared substrate (SIGMAFAST™ p-Nitrophenyl phosphate Tablets) was added per well and allowed to react for 30 minutes at room temperature in the dark. Reactions were quenched with 0.05 ml per well of 1 M NaOH. Absorbance at 405 nm was read on a SpectraMax plate reader, and data were fit to a 4-parameter curve to determine serum TTR protein levels in µg/mL. Protein levels from individual animals were normalized to their respective individual pre-dose plasma protein values to determine the fraction TTR remaining relative to pre-dose.

Figure 3:
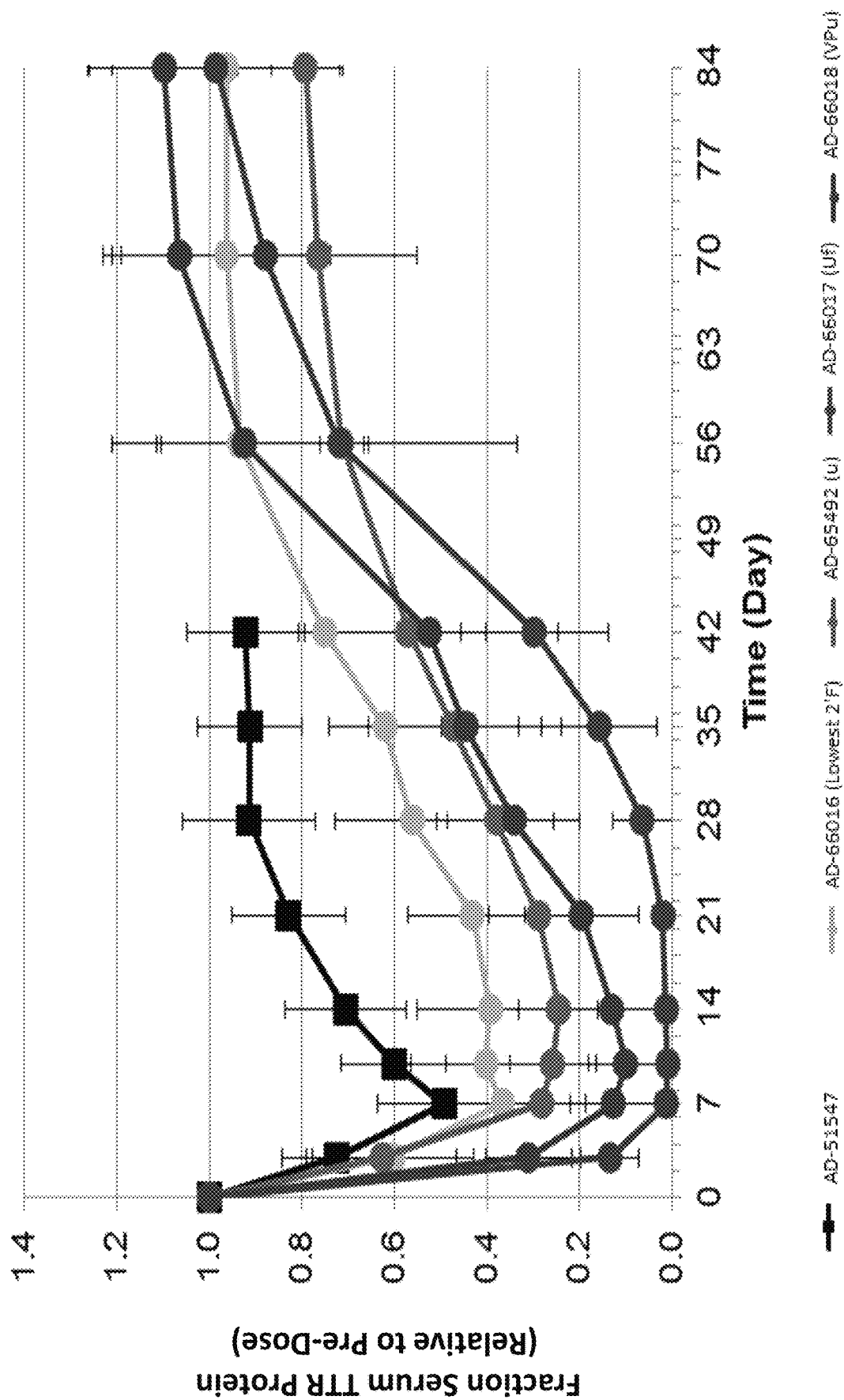
FIG. 3 is a graph depicting TTR protein suppression in transgenic mice that express V30M variant of human TTR (V30M hTTR) following administration of a single subcutaneous dose of 1 mg/kg of the indicated RNAi agents.
Figure 4:
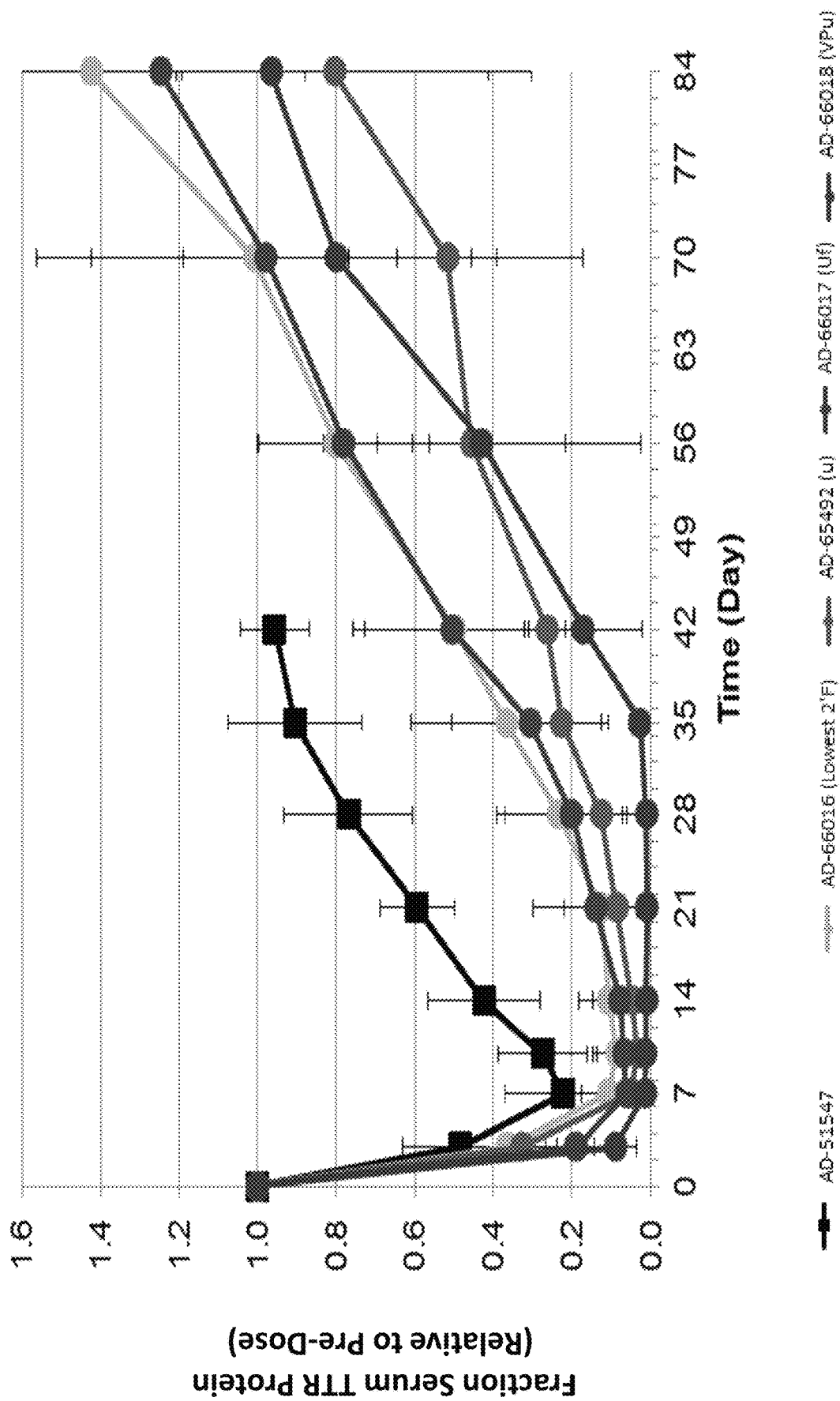
FIG. 4 is a graph depicting TTR protein suppression in transgenic mice that express hTTR V30M following administration of a single subcutaneous dose of 2.5 mg/kg of the indicated RNAi agents.

The results of the 1 mg/kg single dose experiments are provided in FIG. 3 and the results of the 2.5 mg/kg single dose experiments are provided in FIG. 4. The results demonstrate that all of the agents potently and durably inhibit TTR expression, with a nadir reached at about day 7 post-administration. The results also demonstrate that at day 42 following a single 1 mg/kg dose of AD-65492, AD-66017, or AD-66018, more than 40% serum TTR suppression remains, and at day 42 following a single 2.5 mg/kg dose of AD-65492 or AD-66018, more than 60% serum TTR suppression remains. Recovery to baseline serum TTR concentrations occurs between 56 and 84 days post-administration following a single 1 mg/kg dose, and between days 70 and 84 post-administration following a single 2.5 mg/kg dose.

The effective dose for 80% silencing in the animals (ED$_{80}$) was calculated as 1 mg/kg. These data, thus, indicate that AD-65492, AD-66016, AD-66017, and AD-66018 are effective for treating a subject having a TTR-associated disorder in low dose and/or monthly dosing regimes.

Example 3. Rat Exploratory Toxicity Study

Preclinical toxicity studies of AD-66016, AD-65492, AD-66017, and AD-66018 were also performed in rats. Briefly, at days 1, 8, and 15, five male rats per group were subcutaneously administered either a 30 mg/kg or 100 mg/kg dose of AD-66016, AD-65492, AD-66017, or AD-66018. Control animals were administered a placebo at days 1, 8, and 15. At day 16, all of the animals were sacrificed. Prior to sacrifice, the animals were monitored daily for any clinical symptoms and body weights were measured weekly. After sacrifice, the animals were necropsied, and samples were analyzed by complete serum chemistry, hematology and coagulation panels, by histopathology of the liver and kidney, and for liver transaminase concentration.

The results of these analyses demonstrate that AD-66016, AD-65492, AD-66017, and AD-66018 are well-tolerated clinically with no adverse clinical signs or body weight changes.

Example 4. Efficacy of Multi-Dose Administration of AD-65492 and AD-66017

The effect of a multi-dose regimen of AD-65492 and AD-66017 on TTR protein expression in hTTR V30M transgenic (Tg) mice was evaluated.

In one set of experiments, eleven- to thirteen-month old hTTR V30M mice were subcutaneously administered a weekly 2 mg/kg dose of AD-65492 for three weeks (QW×3) and the level of TTR protein was determined in the serum of the animals pre-dose and at days 7, 14, 17, and 21 post-dose, as described above.

Figure 5:
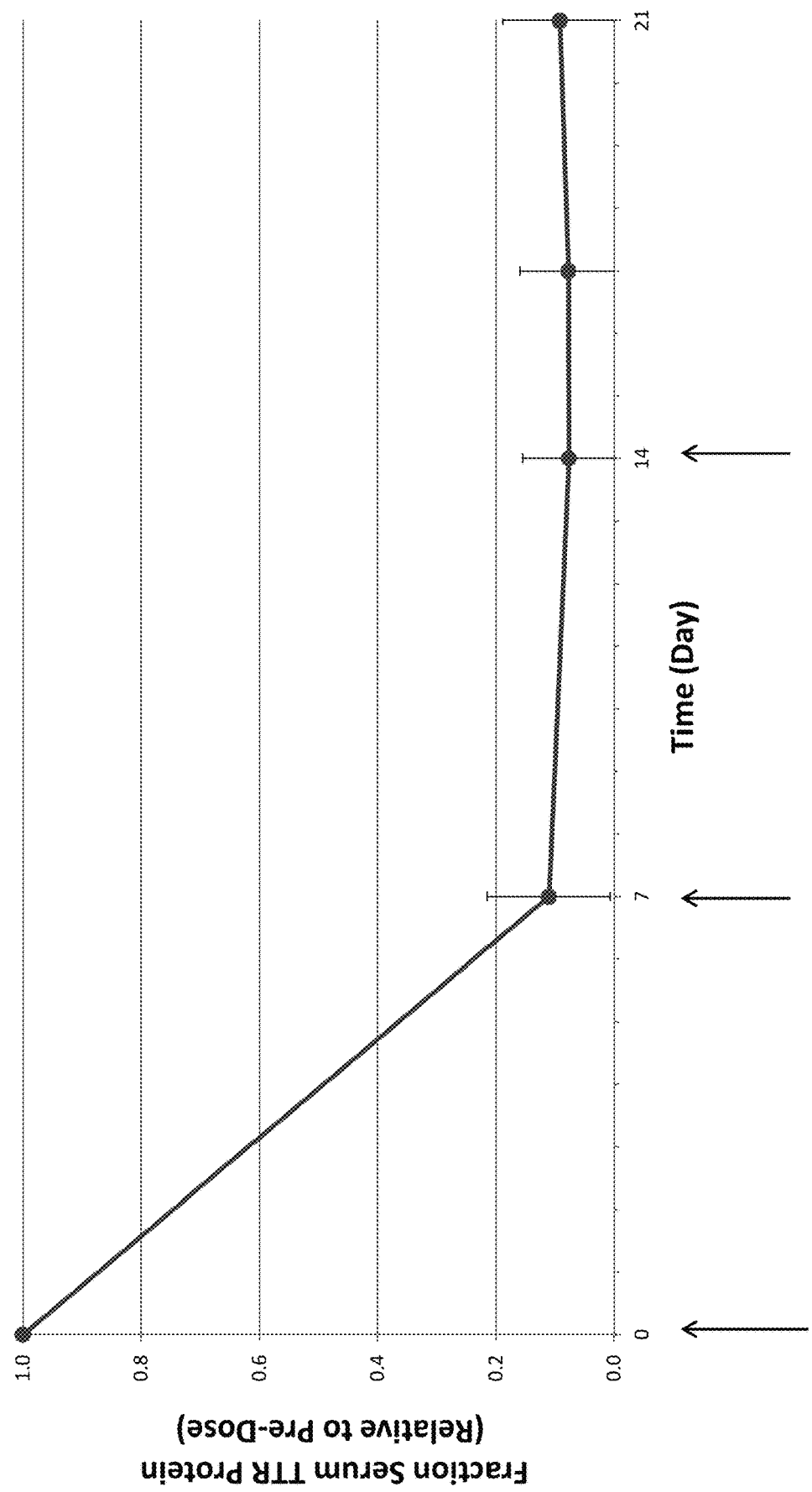
FIG. 5 is a graph depicting TTR protein suppression in transgenic mice that express hTTR V30M following administration of a weekly 2 mg/kg dose of AD-65492 for three weeks (QW×3).

FIG. 5 demonstrates that administration of AD-65492 in a QW×3 dosing regimen to hTTR V30M Tg mice achieved and sustained a greater than 90% suppression of serum TTR protein expression.

In another set of experiments, AD-65492 and AD-66017 were subcutaneously administered to eleven- to thirteen-month old hTTR V30M Tg mice at a 0.3 mg/kg dose once a month for four months (QM×4 @ 0.3 mg/kg), at a 1 mg/kg dose once a month for four months (QM4 @ 1 mg/kg), or at a 3 mg/kg dose once a month for four months (QM4 @ 3 mg/kg). Serun TTR protein levels were determined as described above pre-dose and at days 7, 14, 21, 28, 35, 42, 49, 56, 63, 70, 84, 91, 98, and 185 post-dose.

Figure 6B:
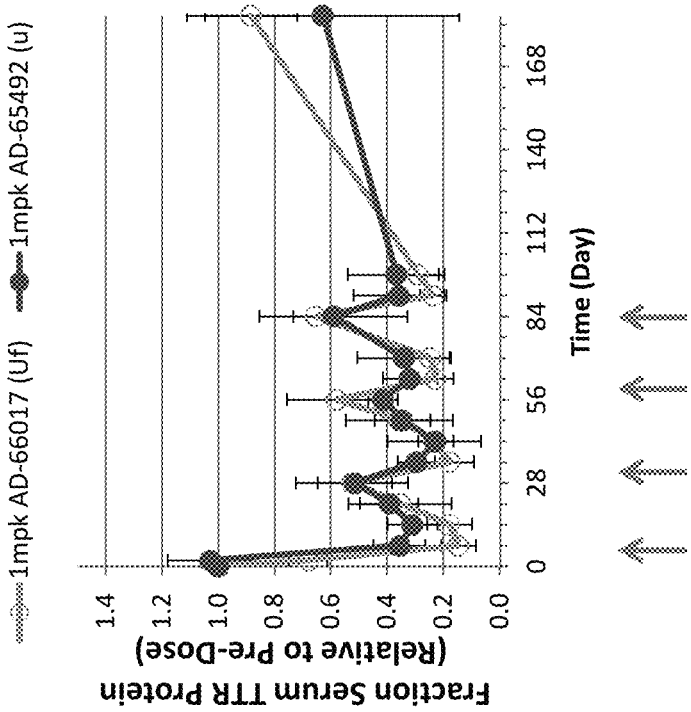
FIG. 6B is graph depicting TTR protein suppression in transgenic mice that express hTTR V30M following subcutaneous administration of a monthly 1 mg/kg dose of the indicated RNAi agents for four months (QM×4 @ 1 mg/kg).
Figure 6A:
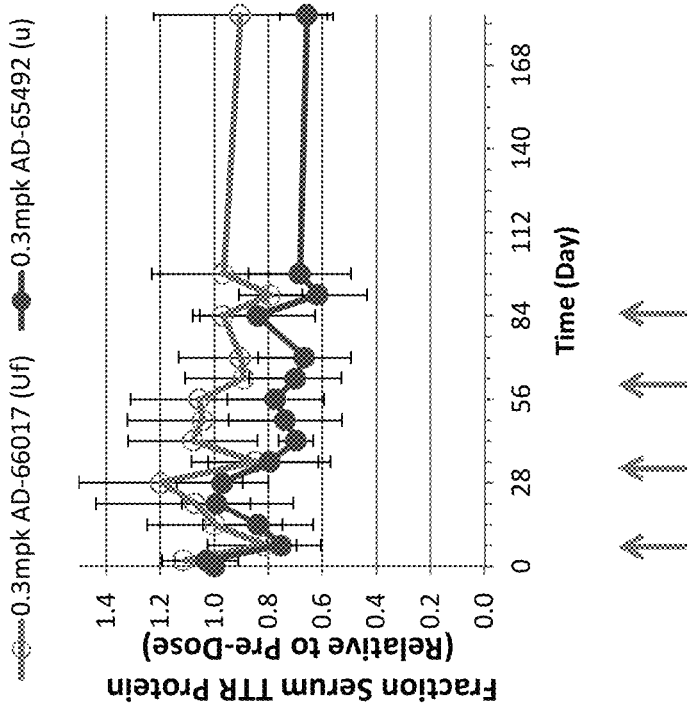
FIG. 6A is graph depicting TTR protein suppression in transgenic mice that express hTTR V30M following subcutaneous administration of a monthly 0.3 mg/kg dose of the indicated RNAi agents for four months (QM×4 @ 0.3 mg/kg).

As shown in FIGS. 6A-6C, the TTR knockdown levels at day 7 post-dose were similar post-second, third and fourth doses and the nadir of TTR expression achieved at the 3 mg/kg, 1 mg/kg and 0.3 mg/kg dose is greater than 80%, about 70-85%, and about 25-35%, respectively. These graphs also demonstrate that AD-65492 provides a more sustained level of TTR silencing than AD-66017, to more than 100 days post final dose, with about 60%, 40%, and about 35% remaining TTR suppression at 3 mg/kg, 1 mg/kg, and 0.3 mg/kg, respectively. Furthermore, for AD-65492, multi-dosing (QM×4) is additive at the 0.3 mg/kg dose resulting in about 40% TTR knockdown after the fourth monthly dose as compared to the first dose having a knockdown of about 25-35%. In addition, although there was some recovery of TTR protein levels prior to each monthly dose across all dose levels for each agent, like a single subcutaneous dose, the effective dose to achieve 80% knockdown ($ED_{80}$) for the multi-dose regimens was calculated as about 1 mg/kg. Thus, the pharmacodynamic activity and kinetics of both compounds in all three dosing regimens was comparable to the pharmacodynamic activity and kinetics of the same compounds when administered as a single dose.

Example 5. TTR Silencing in Non-Human Primates

As demonstrated in the Examples above, AD-65492 and AD-66017 are well-tolerated and potently and durably suppress TTR protein levels in vivo.

Accordingly, the efficacy of AD-65492 and AD-66017 was further studied by administration of different doses and different dosing regimens of these iRNA agents in Cynomologous monkeys. FIG. 7 provides an outline of this study. Briefly, four Groups, Groups 1, 2, 4, and 5, were subcutaneously administered either a single 0.3 mg/kg dose (Groups 1 and 4) or a single 1 mg/kg dose of the iRNA agent (Groups 2 and 5). Four other Groups, Groups 3 and 6-8, were administered a monthly dose of either 1 mg/kg for 4 months (QM×4) (Groups 7 and 8) or a monthly dose of 3 mg/kg for 4 months (QM×4) (Groups 3 and 6). Serum was collected on Days −7 and −1 pre-dose and days 3, 7, 10, 14, 21, 28, 35, 42, 49, 56, 63, 70, 77, 84, 91, 105, and 119 post-dose; plasma was collected on day 1 pre-dose, and 0.5, 1, 2, 4, 8, 24, 48, 96 and 168 hours post dose. The serum level of TTR protein was determined as described above.

Figure 8A:
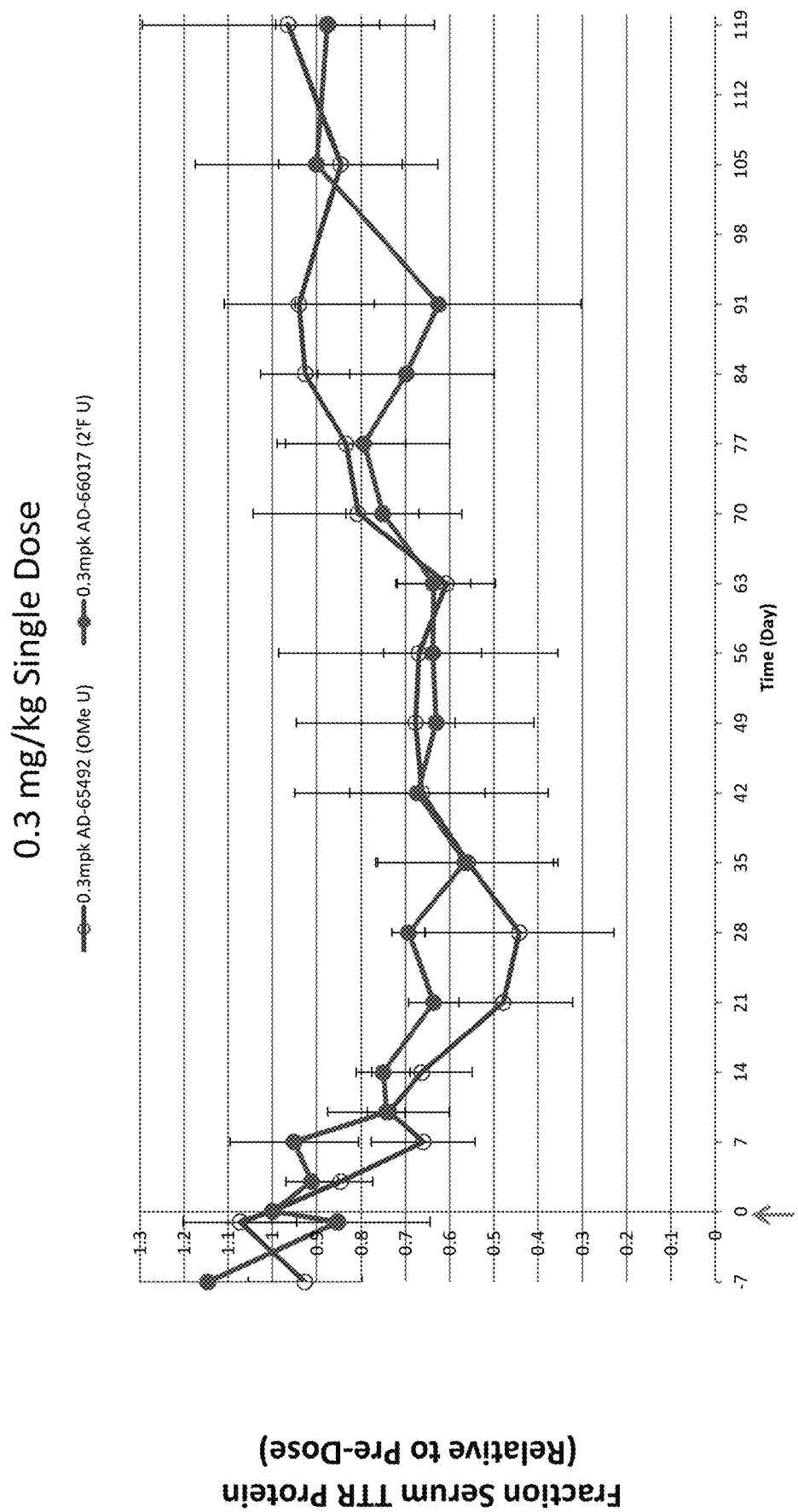
FIG. 8A is a graph depicting TTR protein suppression in Cynomologous monkeys following administration of a single subcutaneous dose of 0.3 mg/kg of the indicated RNAi agents.
Figure 8B:
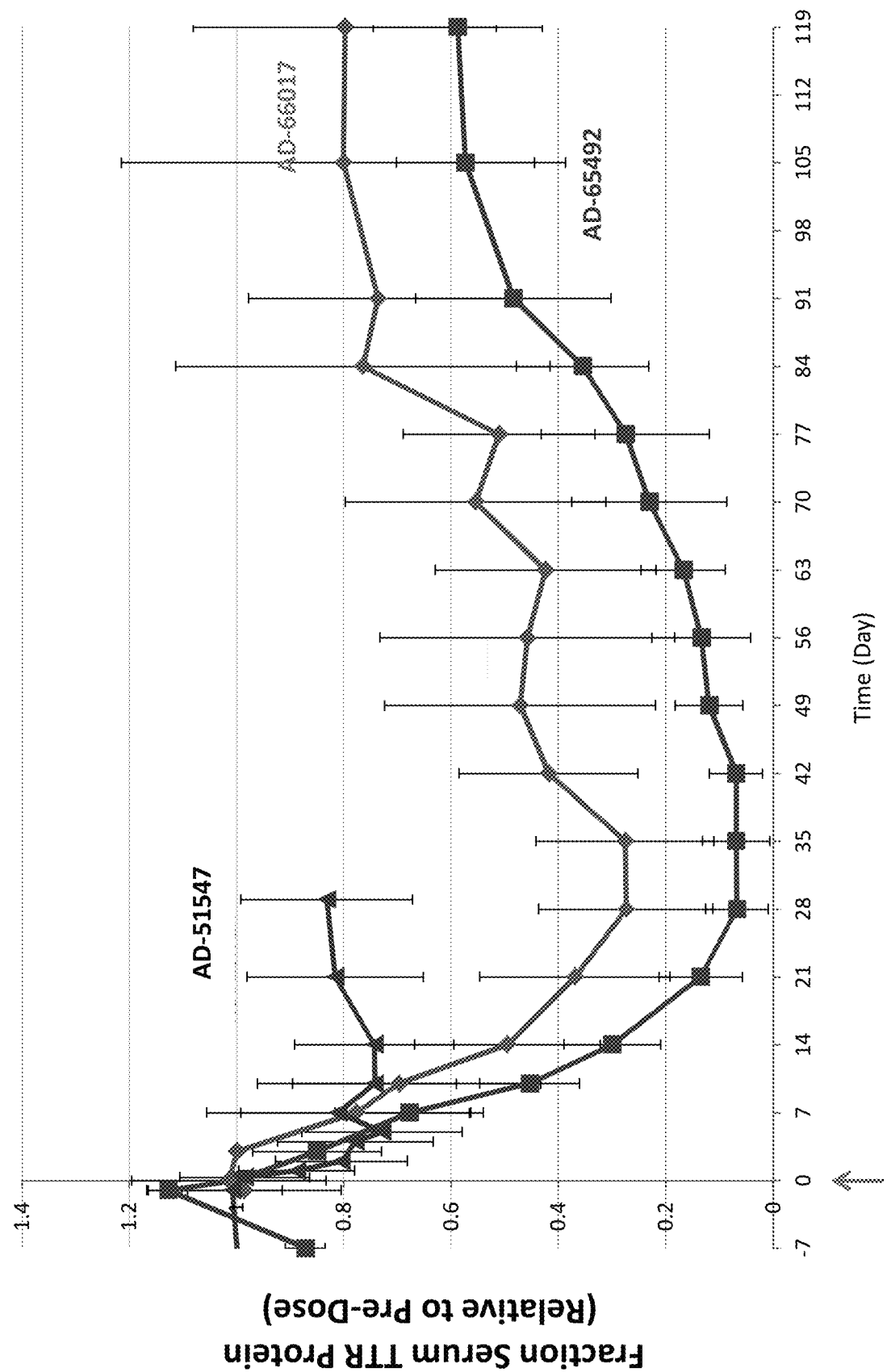
FIG. 8B is a graph depicting TTR protein suppression in Cynomologous monkeys following administration of a single subcutaneous dose of 1 mg/kg of AD-65492, a single subcutaneous dose of 1 mg/kg of AD-66017, or a single subcutaneous dose of 2.5 mg/kg of AD-51547.
Figure 8C:
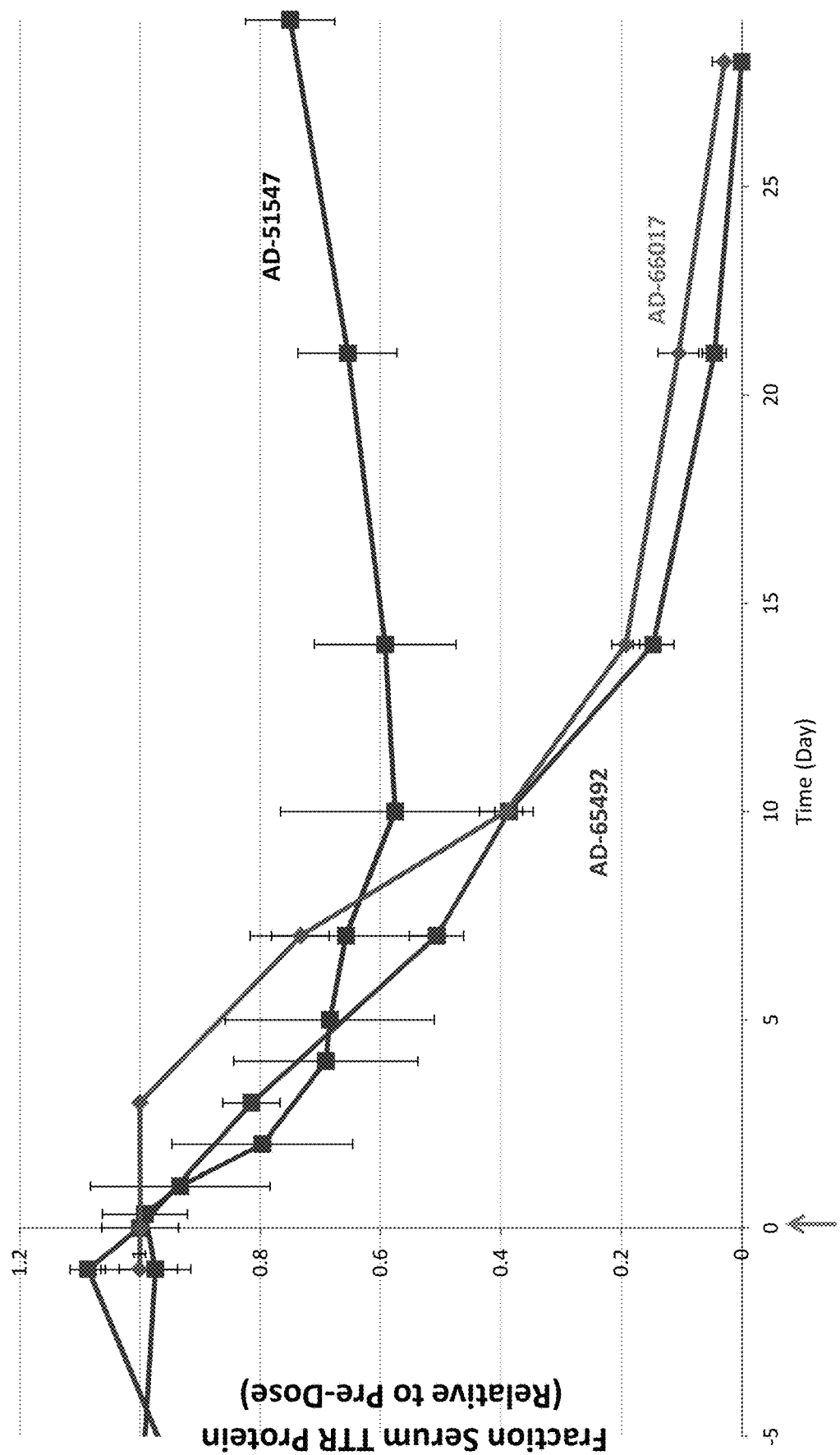
FIG. 8C is a graph depicting TTR protein suppression in Cynomologous monkeys following administration of a single subcutaneous dose of 3 mg/kg of AD-65492, a single subcutaneous dose of 3 mg/kg of AD-66017, or a single subcutaneous dose of 5 mg/kg of AD-51547.

FIG. 8A provides the results of the 0.3 mg/kg single dose study, FIG. 8B provides the results of the 1 mg/kg single dose study, and FIG. 8C provides the results of the 3 mg/kg single dose study. For comparison purposes, FIG. 8B also depicts the effect of administration of a single subcutaneous 2.5 mg/kg dose of AD-51547 on TTR expression in Cynomologous monkeys, and FIG. 8C also depicts the effect of administration of a single subcutaneous 5 mg/kg dose of AD-51547 on TTR expression in Cynomologous monkeys. These graphs demonstrate that the $ED_{50}$ for both AD-65492 and AD-66017 iRNA agents is about 0.3 mg/kg, that the nadir of TTR expression is reached at about day 28 for both doses and for both iRNA agents, and that AD-65492 is more effective at suppressing TTR protein expression than AD-66017 at the higher dose level with a single dose. The graphs also demonstrate that AD-65942 provides greater than 90% sustained suppression of TTR expression through Day 42 following a single 1 mg/kg dose and greater than 80% TTR suppression through Day 63, with about 40% remaining TTR suppression by day 119 post-dose, and that AD-66017 provides a maximum of 73% suppression of TTR expression following a single 1 mg/kg dose, with recovery of TTR expression beginning before Day 35 and recovery to within about 20% of baseline by day 119 post-dose.

Figure 9A:
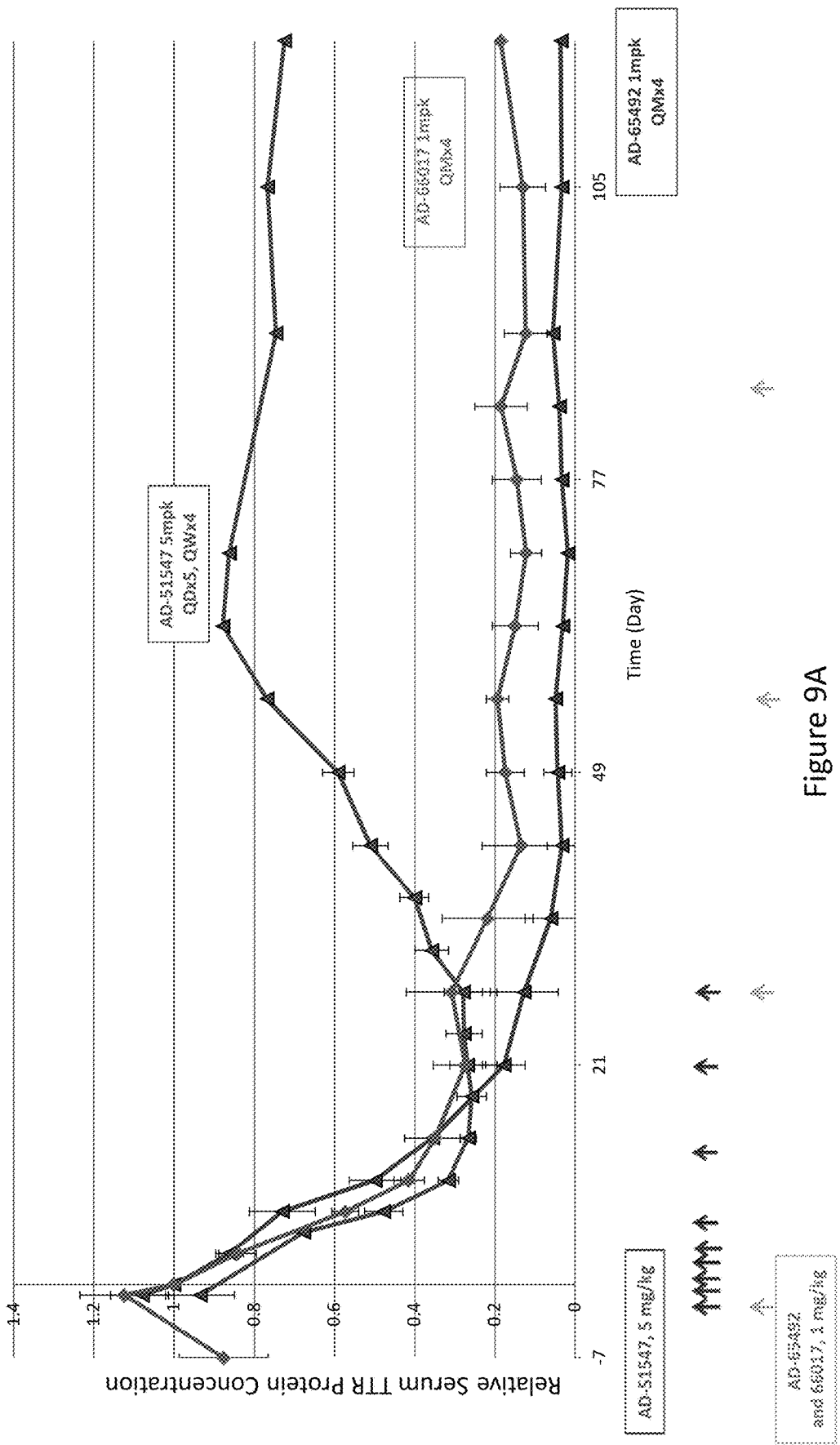
FIG. 9A is a graph depicting TTR protein suppression in Cynomologous monkeys following administration of a monthly subcutaneous dose of 1 mg/kg for four months (QM×4) of AD-65492, a monthly subcutaneous dose of 1 mg/kg for four months (QM×4) of AD-66017, or a daily dose of 5 mg/kg for five days, followed by a weekly 5 mg/kg dose for four weeks (QD×5, QW×4) of AD-51547.
Figure 9B:
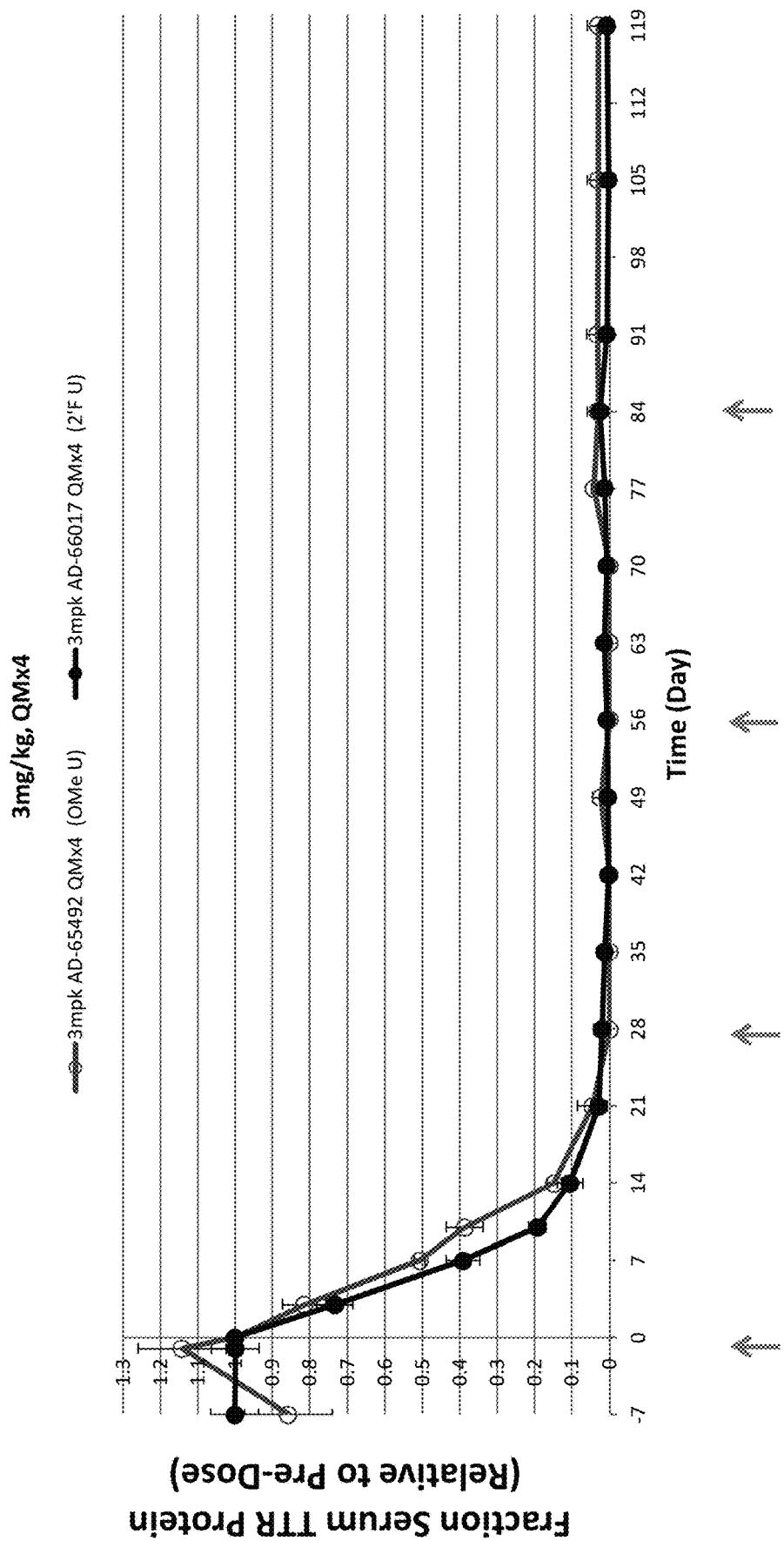
FIG. 9B is a graph depicting TTR protein suppression in Cynomologous monkeys following administration of a monthly subcutaneous dose of 3 mg/kg for four months (QM×4) of the indicated RNAi agents.

FIG. 9A provides the results of the 1 mg/kg multi-dose study and FIG. 9B provides the results of the 3 mg/kg multi-dose study for AD-65492 and AD-66017. For comparison purposes, FIG. 9A also depicts the effect of the administration of a daily 5 mg/kg dose of AD-51547 for 5 days (first five arrows at days 0-4), followed by a weekly 5 mg/kg dose for four weeks (arrows at days 7, 14, 21, and 28) (QD×5, QW×4) on TTR expression in Cynomologous monkeys. The graphs demonstrate that both iRNA agents provide robust TTR protein suppression and that both iRNA agents completely suppress TTR protein expression between Days 21 and 28 at the 3 mg/kg dose. The graphs also demonstrate that AD-65492 is more efficacious that AD-66017 at the 1 mg/kg dose. In addition, the graphs demonstrate that the nadir of TTR expression is achieved between Days 35 and 42 for both iRNA agents at 1 mg/kg, with greater than 85% suppression prior to the second monthly dose of AD-65492, and about 70% suppression prior to the second monthly dose of AD-66017. Maintenance of about 95% and 85% suppression following the third and fourth monthly doses for AD-65492 and AD-66017, respectively, was achieved.

Figure 10A:
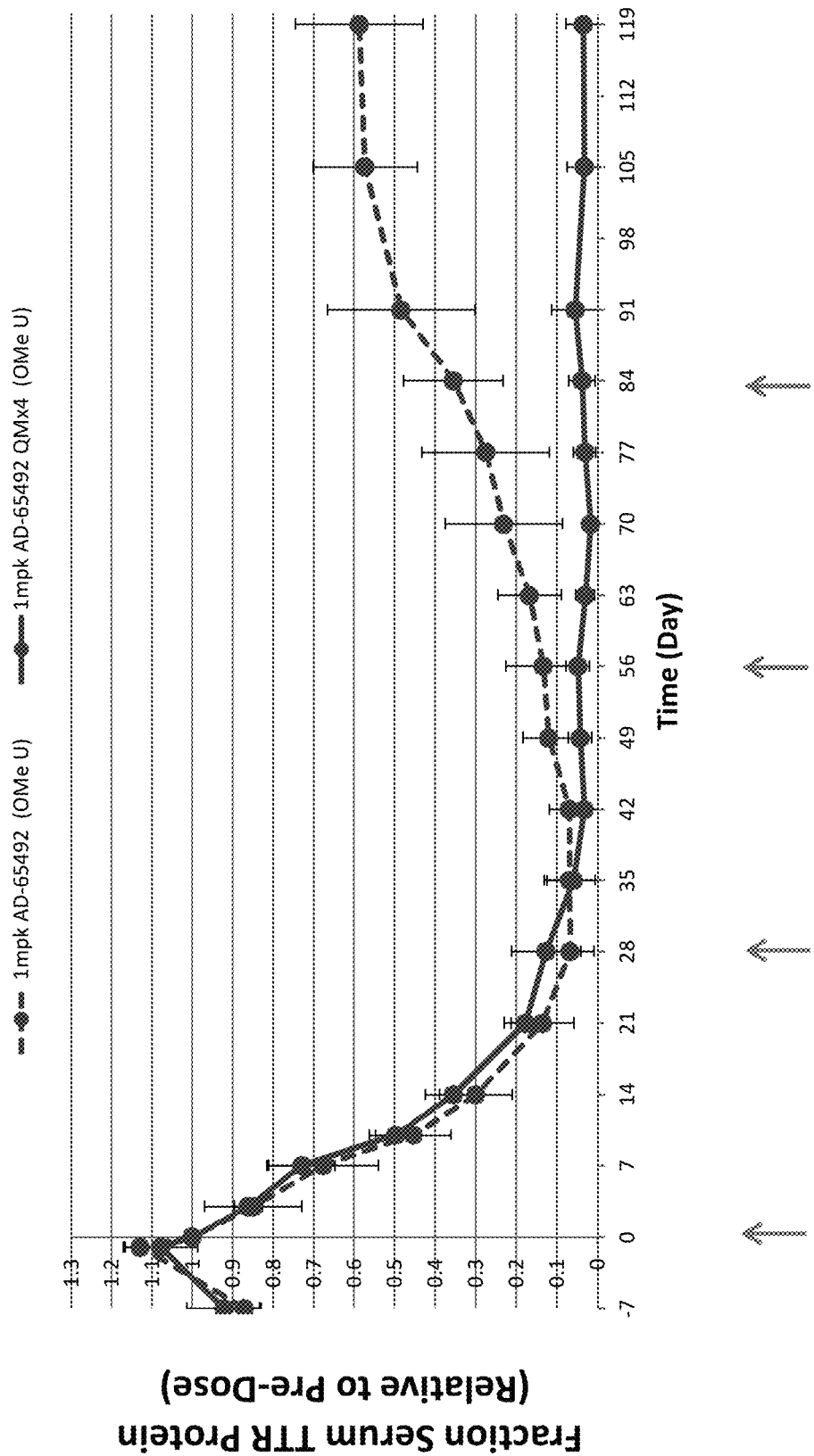
FIG. 10A is a graph depicting the maintenance of TTR suppression by subcutaneous administration of a monthly 1 mg/kg dose of AD-65492 for four months (QM×4; solid line) compared to TTR suppression after a single 1 mg/kg subcutaneous dose of AD-65492 (dashed line) in Cynomologous monkeys.
Figure 10B:
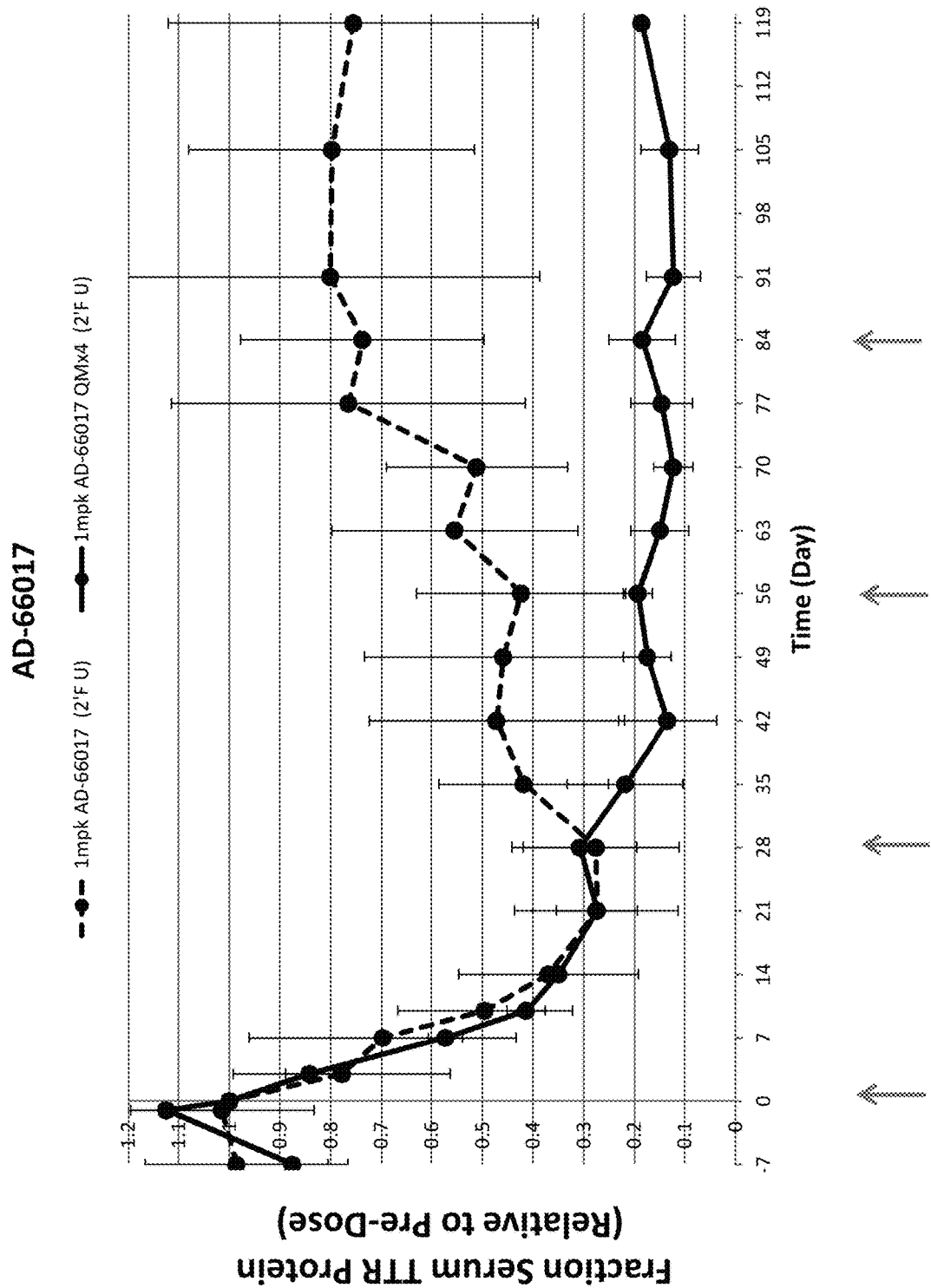
FIG. 10B is a graph depicting an additive effect of subcutaneous administration of a monthly 1 mg/kg dose of AD-66017 for four months (QM×4; solid line) on TTR protein suppression compared to a single subcutaneous dose of 1 mg/kg of AD-66017 (dashed line) in Cynomologous monkeys.

Furthermore, as demonstrated in FIG. 10A, monthly dosing (QM×4) of AD-65492 results in maintenance of greater than 95% TTR suppression and, as demonstrated in FIG. 10B, multi-dosing (QM×4) of AD-66017 is additive at the 1 mg/kg dose. FIG. 10B also demonstrates that there is 85% suppression of TTR protein expression following the second monthly dose of AD-66017 and that this suppression is maintained with the third and fourth monthly doses.

Example 6. Design and Synthesis of Chemically Modified Agents Targeting TTR

Additional double stranded RNAi agents targeting TTR in which substantially all of the sense strand nucleotides and substantially all of the antisense strand nucleotides are modified nucleotides and comprising an antisense strand comprising a region of complementary to SEQ ID NO:2 were designed and synthesized as described above.

The nucleotide sequences of the sense and antisense strands of these agents are provided in Table 5.

Example 7. Design and Synthesis of Chemically Modified Agents Targeting TTR

Additional double stranded RNAi agents targeting TTR were designed and synthesized as described above.

The nucleotide sequences of the unmodified sense and antisense strands of these agents are provided in Table 6, and the nucleotide sequences of the modified sense and antisense strands of these agents are provided in Table 7.

TABLE 5

Modified Sense and Antisense Strand Sequences of TTR dsRNAs

| Duplex ID | Sense strand ID | Sense sequence 5'-3' | SEQ ID NO | Antisense ID | Antisense sequence 5'-3' | SEQ ID NO |
|---|---|---|---|---|---|---|
| AD-65496 | A-131354 | usgsggauUfuCfAfUfguaaccaagaL96 | 51 | A-131360 | PusCfsuugGfuuAfcaugAfaAfucccasusc | 93 |
| AD-65488 | A-131354 | usgsggauUfuCfAfUfguaaccaagaL96 | 52 | A-131358 | PusCfsuugGfuuacaugAfaAfucccasusc | 94 |
| AD-65474 | A-131354 | usgsggauUfuCfAfUfguaaccaagaL96 | 53 | A-131362 | PusCfsuugGfuuAfcaugAfAfaucccasusc | 95 |
| AD-65478 | A-131354 | usgsggauUfuCfAfUfguaaccaagaL96 | 54 | A-131363 | UfsCfsuugGfuuAfcaugAfAfaucccasusc | 96 |
| AD-65493 | A-128512 | usgsggauuucadTguaacaaagaL96 | 55 | A-131366 | PusCfsuugguuacaugAfaaucccasusc | 97 |
| AD-65481 | A-131354 | usgsggauUfuCfAfUfguaaccaagaL96 | 56 | A-131364 | UfsCfsuugGfuuacaugAfaAfucccasusc | 98 |
| AD-65489 | A-131365 | usgggauuucadTguaacaaagaL96 | 57 | A-128520 | usCfsuugguuacaugAfaaucccasusc | 99 |
| AD-65495 | A-131353 | usgsggauUfuCfAfUfguaaCfcaagaL96 | 58 | A-128516 | usCfsuugGfuUfAfcaugAfaAfucccasusc | 100 |
| AD-65482 | A-131373 | usasggauUfuCfAfUfguaaccaagaL96 | 59 | A-131374 | usCfsuugGfuuacaugAfaAfuccuasusu | 101 |
| AD-65468 | A-131354 | usgsggauUfuCfAfUfguaaccaagaL96 | 60 | A-128516 | usCfsuugGfuUfAfcaugAfaAfucccasusc | 102 |
| AD-65367 | A-128499 | usgsggAfuUfuCfAfUfgUfaaccaagAfL96 | 61 | A-128520 | usCfsuugguuacaugAfaaucccasusc | 103 |
| AD-65485 | A-128512 | usgsggauuucadTguaacaaagaL96 | 62 | A-128520 | usCfsuugguuacaugAfaaucccasusc | 104 |
| AD-65470 | A-131367 | gsgsauUfuCfAfUfguaaccaagaL96 | 63 | A-131369 | usCfsuugguuacaugAfaauccscsa | 105 |
| AD-65469 | A-131354 | usgsggauUfuCfAfUfguaaccaagaL96 | 64 | A-131361 | usCfsuugGfuuAfcaugAfAfaucccasusc | 106 |
| AD-65473 | A-131355 | usgggauUfuCfAfUfguaaccaagaL96 | 65 | A-131356 | usCfuugGfuUfAfcaugAfaAfucccasusc | 107 |
| AD-65484 | A-131355 | usgggauUfuCfAfUfguaaccaagaL96 | 66 | A-131357 | usCfuugGfuuacaugAfaAfucccasusc | 108 |
| AD-65477 | A-131353 | usgsggauUfuCfAfUfguaaCfcaagaL96 | 67 | A-128517 | usCfsuugGfuuacaugAfaAfucccasusc | 109 |
| AD-65497 | A-131367 | gsgsauUfuCfAfUfguaaccaagaL96 | 68 | A-131368 | usCfsuugguuacaugAfaauccsusa | 110 |
| AD-65475 | A-131370 | gsgauUfuCfAfUfguaaccaagaL96 | 69 | A-131371 | usCfuugguuacaugAfaauccscsa | 111 |
| AD-65480 | A-131354 | usgsggauUfuCfAfUfguaaccaagaL96 | 70 | A-128517 | usCfsuugGfuuacaugAfaAfucccasusc | 112 |
| AD-65479 | A-131372 | gsgsauuucAfUfguaaccaagaL96 | 71 | A-131369 | usCfsuugguuacaugAfaauccscsa | 113 |
| AD-65492 | | usgsggauUfuCfAfUfguaaccaagaL96 | 72 | | usCfsuugGfuuAfcaugAfaAfucccasusc | 114 |
| AD-65494 | A-1285120 | usgsggauuucadTguaacaaagaL96 | 73 | A-128526 | PusdCsuuggvuadCaugdAaaucccasusc | 115 |
| AD-65499 | A-128557 | usgsggauuucadTguaacY34aagaL96 | 74 | A-128526 | PusdCsuuggvuadCaugdAaaucccasusc | 116 |
| AD-65491 | A-128557 | usgsggauuucadTguaacY34aagaL96 | 75 | A-128525 | usdCsuuggvuadCaugdAaaucccasusc | 117 |
| AD-65498 | A-1285121 | usgsggauuucadTguaacaaagaL96 | 76 | A-131375 | UfsdCsuuggvuadCaugdAaaucccasusc | 118 |
| AD-65490 | A-128512 | usgsggauuucadTguaacaaagaL96 | 77 | A-128553 | usdCsuuggvuadCsaugdAsaaucccasusc | 119 |
| AD-64520 | A-128557 | usgsggauuucadTguaacY34aagaL96 | 78 | A-128553 | usdCsuuggvuadCsaugdAsaaucccasusc | 120 |
| AD-64527 | A-128512 | usgsggauuucadTguaacaaagaL96 | 79 | A-128525 | usdCsuuggvuadCaugdAaaucccasusc | 121 |

TABLE 5-continued

Modified Sense and Antisense Strand Sequences of TTR dsRNAs

| Sense strand DuplexID | ID | Sense sequence 5'-3' | SEQ ID NO | Antisense ID | Antisense sequence 5'-3' | SEQ ID NO |
|---|---|---|---|---|---|---|
| AD-65472 | A-131376 | gsgsauuucadTguaacaaagaL96 | 80 | A-131377 | usdCsuugguuadCaugdAaauccscsa | 122 |
| AD-65486 | A-128557 | usgsggauuucadTguaacY34aagaL96 | 81 | A-128520 | usCfsuugguuacaugAfaauccccasusc | 123 |
| AD-65472 | A-131376 | gsgsauuucadTguaacaaagaL96 | 82 | A-131377 | usdCsuugguuadCaugdAaauccscsa | 124 |
| AD-64515 | | usgsggauuucadTguaac(Cgn)aagaL96 | 83 | | usdCsuugguuadCaugdAaaucccasusc | 125 |
| AD-64536 | | usgsggauuucadTguaac(Cgn)aagaL96 | 84 | | usdCsuugguuadCsaugdAsaaucccasusc | 126 |
| AD-65471 | | usgsggauuucadTguaac(Cgn)aagaL96 | 85 | | usCfsuugguuacaugAfaaucccasusc | 127 |
| AD-65483 | | usgsggauuucadTguaac(Cgn)aagaL96 | 86 | | PusdCsuugguuadCaugdAaaucccasusc | 128 |
| AD-59152 | A-106305 | UfgGfgAfuUfuCfAfUfgUfaacCfaAfgAfL96 | 87 | A-119923 | PuCfuUfgGfUfUfaCfaugAfaAfuCfcCfasUfsc | 129 |
| AD-65476 | A-106305 | UfgGfgAfuUfuCfAfUfgUfaacCfaAfgAfL96 | 88 | A-131351 | UfCfuUfgGfUfUfaCfaugAfaAfuCfcCfasUfsc | 130 |
| AD-64480 | A-128493 | UfsgsGfgAfuUfuCfAfUfgUfaAfcCfaAfgAfL96 | 89 | A-128495 | PusCfsuUfgGfuUfaCfaugAfaAfuCfcCfasusc | 131 |
| AD-51547 | A-106305 | UfgGfgAfuUfuCfAfUfgUfaacCfaAfgAfL96 | 90 | A-1029782 | uCfuUfgGfUfUfaCfaugAfaAfuCfcCfasUfsc | 132 |
| AD-65487 | A-1284937 | UfsgsGfgAfuUfuCfAfUfgUfaAfcCfaAfgAfL96 | 91 | A-131352 | UfsCfsuUfgGfUfUfaCfaugAfaAfuCfcCfasusc | 133 |
| AD-64474 | A-1284935 | UfsgsGfgAfuUfuCfAfUfgUfaAfcCfaAfgAfL96 | 92 | A-1284947 | usCfsuUfgGfuUfaCfaugAfaAfuCfcCfasusc | 134 |

TABLE 6

Unmodified Sense and Antisense Strand Sequences of TTR dsRNAs

| Duplex ID | Sense sequence (5' to 3') | SEQ ID NO | Antisense Start Site Relative to NM_000371.2 | Antisense sequence (5' to 3') | SEQ ID NO |
|---|---|---|---|---|---|
| AD-68322 | AUGGGAUUUCAUGUAACCAAA | 135 | 504 | UUUGGUUACAUGAAAUCCCAUCC | 167 |
| AD-60668 | AUGGGAUUUCAUGUAACCAAA | 136 | 504 | UUUGGUUACAUGAAAUCCCAUCC | 168 |
| AD-68330 | AUGGGAUUUCAUGUAACCAAA | 137 | 504 | UUUGGUUACAUGAAAUCCCAUCC | 169 |
| AD-64474 | UGGGAUUUCAUGUAACCAAGA | 138 | 505 | UCUUGGUUACAUGAAAUCCCAUC | 170 |
| AD-65468 | UGGGAUUUCAUGUAACCAAGA | 139 | 505 | UCUUGGUUACAUGAAAUCCCAUC | 171 |
| AD-65492 | UGGGAUUUCAUGUAACCAAGA | 140 | 505 | UCUUGGUUACAUGAAAUCCCAUC | 172 |
| AD-65480 | UGGGAUUUCAUGUAACCAAGA | 141 | 505 | UCUUGGUUACAUGAAAUCCCAUC | 173 |
| AD-60636 | UUUCAUGUAACCAAGAGUAUU | 142 | 510 | AAUACUCUUGGUUACAUGAAAUC | 174 |
| AD-68320 | UUUCAUGUAACCAAGAGUAUU | 143 | 510 | AAUACUCUUGGUUACAUGAAAUC | 175 |
| AD-68326 | UUUCAUGUAACCAAGAGUAUU | 144 | 510 | AAUACUCUUGGUUACAUGAAAUC | 176 |
| AD-60611 | UGUAACCAAGAGUAUUCCAUU | 145 | 515 | AAUGGAAUACUCUUGGUUACAUG | 177 |
| AD-68331 | UGUAACCAAGAGUAUUCCAUU | 146 | 515 | AAUGGAAUACUCUUGGUUACAUG | 178 |
| AD-68315 | UGUAACCAAGAGUAUUCCAUU | 147 | 515 | AAUGGAAUACUCUUGGUUACAUG | 179 |
| AD-68319 | AACCAAGAGUAUUCCAUUUUU | 148 | 518 | AAAAAUGGAAUACUCUUGGUUAC | 180 |
| AD-60612 | AACCAAGAGUAUUCCAUUUUU | 149 | 518 | AAAAAUGGAAUACUCUUGGUUAC | 181 |

TABLE 6-continued

Unmodified Sense and Antisense Strand Sequences of TTR dsRNAs

| Duplex ID | Sense sequence (5' to 3') | SEQ ID NO | Antisense Start Site Relative to NM_000371.2 | Antisense sequence (5' to 3') | SEQ ID NO |
|---|---|---|---|---|---|
| AD-68316 | AACCAAGAGUAUUCCAUUUUU | 150 | 518 | AAAAAUGGAAUACUCUUGGUUAC | 182 |
| AD-60664 | UUUUUACUAAAGCAGUGUUUU | 151 | 534 | AAAACACUGCUUUAGUAAAAAUG | 183 |
| AD-68321 | UUUUUACUAAAGCAGUGUUUU | 152 | 534 | AAAACACUGCUUUAGUAAAAAUG | 184 |
| AD-68318 | UUUUUACUAAAGCAGUGUUUU | 153 | 534 | AAAACACUGCUUUAGUAAAAAUG | 185 |
| AD-60665 | UUACUAAAGCAGUGUUUUCAA | 154 | 537 | UUGAAAACACUGCUUUAGUAAAA | 186 |
| AD-60642 | CUAAAGCAGUGUUUUCACCUA | 155 | 540 | UAGGUGAAAACACUGCUUUAGUA | 187 |
| AD-68329 | CUAAAGCAGUGUUUUCACCUA | 156 | 540 | UAGGUGAAAACACUGCUUUAGUA | 188 |
| AD-68334 | CUAAAGCAGUGUUUUCACCUA | 157 | 540 | UAGGUGAAAACACUGCUUUAGUA | 189 |
| AD-68328 | GGCAGAGACAAUAAAACAUUA | 158 | 582 | UAAUGUUUUAUUGUCUCUGCCUG | 190 |
| AD-68333 | GGCAGAGACAAUAAAACAUUA | 159 | 582 | UAAUGUUUUAUUGUCUCUGCCUG | 191 |
| AD-60639 | GGCAGAGACAAUAAAACAUUA | 160 | 582 | UAAUGUUUUAUUGUCUCUGCCUG | 192 |
| AD-60643 | CAGAGACAAUAAAACAUUCCU | 161 | 584 | AGGAAUGUUUUAUUGUCUCUGCC | 193 |
| AD-68317 | CAGAGACAAUAAAACAUUCCU | 162 | 584 | AGGAAUGUUUUAUUGUCUCUGCC | 194 |
| AD-68335 | CAGAGACAAUAAAACAUUCCU | 163 | 584 | AGGAAUGUUUUAUUGUCUCUGCC | 195 |
| AD-68327 | CAAUAAAACAUUCCUGUGAAA | 164 | 590 | UUUCACAGGAAUGUUUUAUUGUC | 196 |
| AD-68332 | CAAUAAAACAUUCCUGUGAAA | 165 | 590 | UUUCACAGGAAUGUUUUAUUGUC | 197 |
| AD-60637 | CAAUAAAACAUUCCUGUGAAA | 166 | 590 | UUUCACAGGAAUGUUUUAUUGUC | 198 |

TABLE 7

Modified Sense and Antisense Strand Sequences of TTR dsRNAs

| Duplex ID | Sense sequence (5' to 3') | SEQ ID NO | Antisense sequence (5' to 3') | SEQ ID NO |
|---|---|---|---|---|
| AD-68322 | asusgggaUfuUfCfAfuguaaccaaaL96 | 199 | usUfsuggUfuAfCfaugaAfaUfcccauscsc | 231 |
| AD-60668 | AfsusGfgGfaUfuUfCfAfuGfuAfaCfcAfaAfL96 | 200 | usUfsuGfgUfuAfcAfugaAfaUfcCfcAfuscsc | 232 |
| AD-68330 | asusgggaUfuUfCfAfuguaaccaaaL96 | 201 | usUfsuggUfuacaugaAfaUfcccauscsc | 233 |
| AD-64474 | UfsgsGfgAfuUfuCfAfUfgUfaAfcCfaAfgAfL96 | 202 | usCfsuUfgGfuUfaCfaugAfaAfuCfcCfasusc | 234 |
| AD-65468 | usgsgggauUfuCfAfAfUfguaaccaagaL96 | 203 | usCfsuugGfuUfAfcaugAfaAfucccasusc | 235 |
| AD-65492 | usgsgggauUfuCfAfAfUfguaaccaagaL96 | 204 | usCfsuugGfuuAfcaugAfaAfucccasusc | 236 |
| AD-65480 | usgsgggauUfuCfAfAfUfguaaccaagaL96 | 205 | usCfsuugGfuuacaugAfaAfucccasusc | 237 |
| AD-60636 | UfsusUfcAfuGfuAfAfCfcAfaGfaGfuAfuUfL96 | 206 | asAfsuAfcUfcUfuGfguuAfcAfuGfaAfasusc | 238 |
| AD-68320 | ususucauGfuAfAfCfcaagaguauuL96 | 207 | asAfsuacUfcUfUfgguuAfcAfugaaasusc | 239 |
| AD-68326 | ususucauGfuAfAfCfcaagaguauuL96 | 208 | asAfsuacUfcuugguuAfcAfugaaasusc | 240 |
| AD-60611 | UfsgsUfaAfcCfaAfGfAfgUfaUfuCfcAfuUfL96 | 209 | asAfsuGfgAfaUfaCfucuUfgGfuUfaCfasusg | 241 |
| AD-68331 | usgsuaacCfaAfGfAfguauuccauuL96 | 210 | asAfsuggAfaUfAfcucuUfgGfuuacasusg | 242 |
| AD-68315 | usgsuaacCfaAfGfAfguauuccauuL96 | 211 | asAfsuggAfauacucuUfgGfuuacasusg | 243 |
| AD-68319 | asasccaaGfaGfUfAfuuccauuuuuL96 | 212 | asAfsaaaUfgGfAfauacUfcUfugguusasc | 244 |

TABLE 7-continued

Modified Sense and Antisense Strand Sequences of TTR dsRNAs

| Duplex ID | Sense sequence (5' to 3') | SEQ ID NO | Antisense sequence (5' to 3') | SEQ ID NO |
|---|---|---|---|---|
| AD-60612 | AfsasCfcAfaGfaGfUfAfuUfcCfaUfuUfuUfL96 | 213 | asAfsaAfaUfgGfaAfuacUfcUfuGfgUfusasc | 245 |
| AD-68316 | asasccaaGfaGfUfAfuuccauuuuuL96 | 214 | asAfsaaaUfggaauacUfcUfugguusasc | 246 |
| AD-60664 | UfsusUfuUfaCfuAfAfAfgCfaGfuGfuUfuUfL96 | 215 | asAfsaAfcAfcUfgCfuuuAfgUfaAfaAfasusg | 247 |
| AD-68321 | ususuuuaCfuAfAfAfgcaguguuuuL96 | 216 | asAfsaacAfcUfGfcuuuAfgUfaaaaasusg | 248 |
| AD-68318 | ususuuuaCfuAfAfAfgcaguguuuuL96 | 217 | asAfsaacAfcugcuuuAfgUfaaaaasusg | 249 |
| AD-60665 | UfsusAfcUfaAfaGfCfAfgUfgUfuUfuCfaAfL96 | 218 | usUfsgAfaAfaCfaCfugcUfuUfaGfuAfasasa | 250 |
| AD-60642 | CfsusAfaAfgCfaGfUfGfuUfuUfcAfcCfuAfL96 | 219 | usAfsgGfuGfaAfaAfcacUfgCfuUfuAfgsusa | 251 |
| AD-68329 | csusaaagCfaGfUfGfuuuucaccuaL96 | 220 | usAfsgguGfaaaacacUfgCfuuuagsusa | 252 |
| AD-68334 | csusaaagCfaGfUfGfuuuucaccuaL96 | 221 | usAfsgguGfaAfAfacacUfgCfuuuagsusa | 253 |
| AD-68328 | gsgscagaGfaCfAfAfuaaaacauuaL96 | 222 | usAfsaugUfuuuauugUfcUfcugccsusg | 254 |
| AD-68333 | gsgscagaGfaCfAfAfuaaaacauuaL96 | 223 | usAfsaugUfuUfUfauugUfcUfcugccsusg | 255 |
| AD-60639 | GfsgsCfaGfaGfaCfAfAfuAfaAfaCfaUfuAfL96 | 224 | usAfsaUfgUfuUfuAfuugUfcUfcUfgCfcsusg | 256 |
| AD-60643 | CfsasGfaGfaCfaAfUfAfaAfaCfaUfuCfcUfL96 | 225 | asGfsgAfaUfgUfuUfauUfgUfcUfcUfgscsc | 257 |
| AD-68317 | csasgagaCfaAfUfAfaaacauuccuL96 | 226 | asGfsgaaUfguuuuauUfgUfcucugscsc | 258 |
| AD-68335 | csasgagaCfaAfUfAfaaacauuccuL96 | 227 | asGfsgaaUfgUfUfuuauUfgUfcucugscsc | 259 |
| AD-68327 | csasauaaAfaCfAfUfuccugugaaaL96 | 228 | usUfsucaCfaggaaugUfuUfuauugsusc | 260 |
| AD-68332 | csasauaaAfaCfAfUfuccugugaaaL96 | 229 | usUfsucaCfaGfGfaaugUfuUfuauugsusc | 261 |
| AD-60637 | CfsasAfuAfaAfaCfAfUfuCfcUfgUfgAfaAfL96 | 230 | usUfsuCfaCfaGfgAfaugUfuUfuAfuUfgsusc | 262 |

Example 8. Administration of AD-65492 to Cynomologous Monkeys

The efficacy of AD-65492 was further assessed by administration to Cynomologous monkeys.

In a first set of experiments, four Groups (Groups 1, 2, 3, and 7), were subcutaneously administered a single 0.3 mg/kg dose (Group 1); a single dose of 1 mg/kg (Group 2); a monthly dose of 1 mg/kg for 4 months (QM×4) (Group 7); or a monthly dose of 3 mg/kg for 4 months (QM×4) (Group 3).

Serum, plasma, and sparse liver samples were collected pre-dose and on days 3, 7, 10, 14, 21, 28, 35, 42, 49, 56, 63, 70, 77, 84, 91, 98, 112, 126, 154, 175, 203, 230, 260, 290, 310, 335, and 364 for Groups 3 and 4.

For Groups 1 and 2, serum was collected on days −7 and −1 pre-dose, and days 3, 7, 10, 14, 21, 28, 35, 42, 49, 56, 63, 70, 77, 84, 91, 105, and 119 post-dose; plasma was collected on day 1 pre-dose, and 0.5, 1, 2, 4, 8, 24, 48, 96 and 168 hours post-dose.

For Groups 3 and 7 serum was collected on days −7 and −1 pre-dose, and days 3, 7, 10, 14, 21, 28, 35, 42, 49, 56, 63, 70, 77, 84, 91, 98, 112, 127, 155, 176, 204, 232, 260, 288, 316, 344 and 372 post-dose; plasma was collected on day 1 pre-dose, and 0.5, 1, 2, 4, 8, 12, 24, 48, 96 and 168 hours post-dose; plasma was also collected on day 85 pre-dose and 0.5, 1, 2, 4, 8, 12, 24, 48, 96 and 168 hours post-dose.

For Group 7, sparse liver samples were collected on day 1, eight hours pre-dose (i.e., 8 hours before the dose of AD-65492 was administered to the subject, a sparse liver sample was collected from the subject); and on post-dose day 7; day 22; day 29, eight hours pre-dose; day 57, eight hours pre-dose; day 85, eight hours pre-dose; day 91; day 106; and day 141.

For Group 3, sparse liver samples were collected post-dose on day 29, eight hours pre-dose; day 57, eight hours pre-dose; day 85, eight hours pre-dose; day 91, day 106, and day 141.

The serum level of TTR protein was determined as described above.

Figure 11:
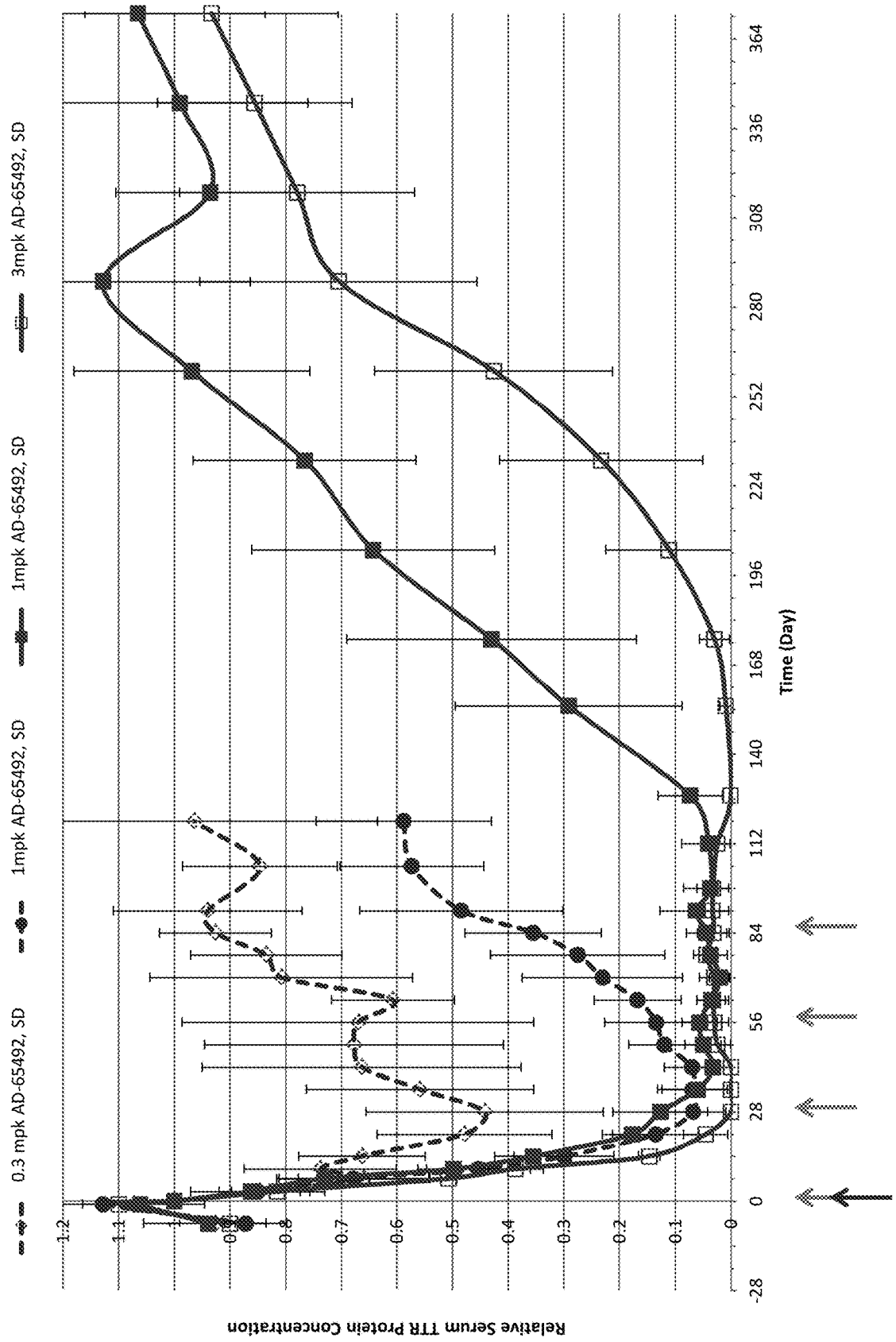
FIG. 11 is a graph depicting sustained serum TTR suppression in Cynomologous monkeys following monthly subcutaneous administration of a 1 mg/kg dose of AD-65492 for four months (QM×4), or monthly subcutaneous administration of a 3 mg/kg dose of AD-65492 for four months (QM×4) as compared to a single subcutaneously administered 1 mg/kg dose of AD-65492 or a single subcutaneously administered 0.3 mg/kg dose of AD-65492.

FIG. 11 provides the results of these studies, and shows robust suppression of TTR expression achieved by administration of AD-65492. The data demonstrate that AD-65492 provides greater than 90% sustained suppression of TTR expression for approximately 6 weeks and 17 weeks post-final dose following monthly dosing for four months (QM×4) with 1 mg/kg (Group 7) of AD-65492 or 3 mg/kg of AD-65492 (Group 3), respectively. The data also demonstrate about 40% suppression of TTR expression at 17 weeks post-final dose following monthly dosing for four months (QM×4) with 1 mg/kg of AD-65492 (Group 7).

The data indicate that quarterly dosing of human subjects with AD-65492 would be effective in suppressing TTR expression at a dose level intermediate to 1 mg/kg and 3 mg/kg, e.g., 2 mg/kg, assuming a 1:1 translation between dosing in Cynomologous monkeys and humans.

Figure 12:
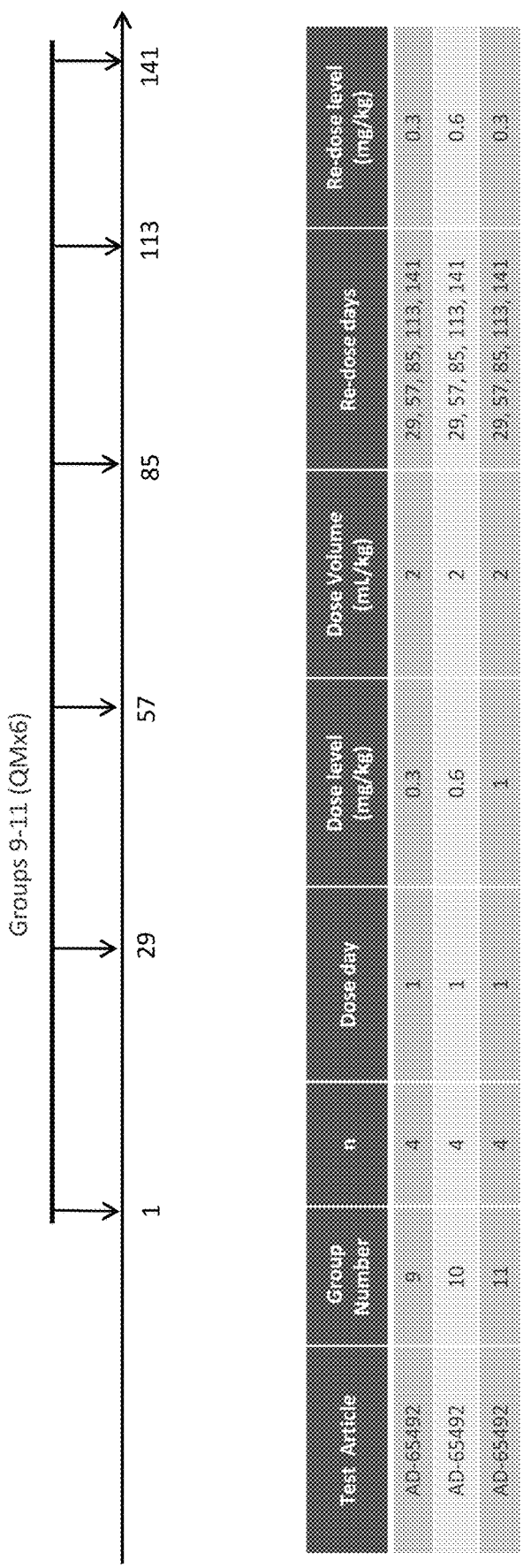
FIG. 12 depicts the study design of AD-65492 subcutaneous administration to Cynomologous monkeys.

In a second set of experiments, three Groups (Groups 9, 10, and 11; see FIG. 12), were subcutaneously administered a monthly dose of either 0.3 mg/kg for 6 months (QM×6) (Group 9); a monthly dose of 0.6 mg/kg for 6 months (QM×6) (Group 10); or an initial dose of 1 mg/kg followed by a monthly maintenance dose of 0.3 mg/kg for one month (QM×1) after the initial dose for five months (QM×5) (Group 11).

Serum samples were collected on days −7 and −1 pre-dose, and days 4, 8, 11, 15, 22, 29, 36, 43, 50, 57, 64, 71, 78, 85, 92, 99, 113, 127, 155, 176, and 204, 232, 260 and 288. post-dose. The serum level of TTR protein was determined as described above.

Figure 13:
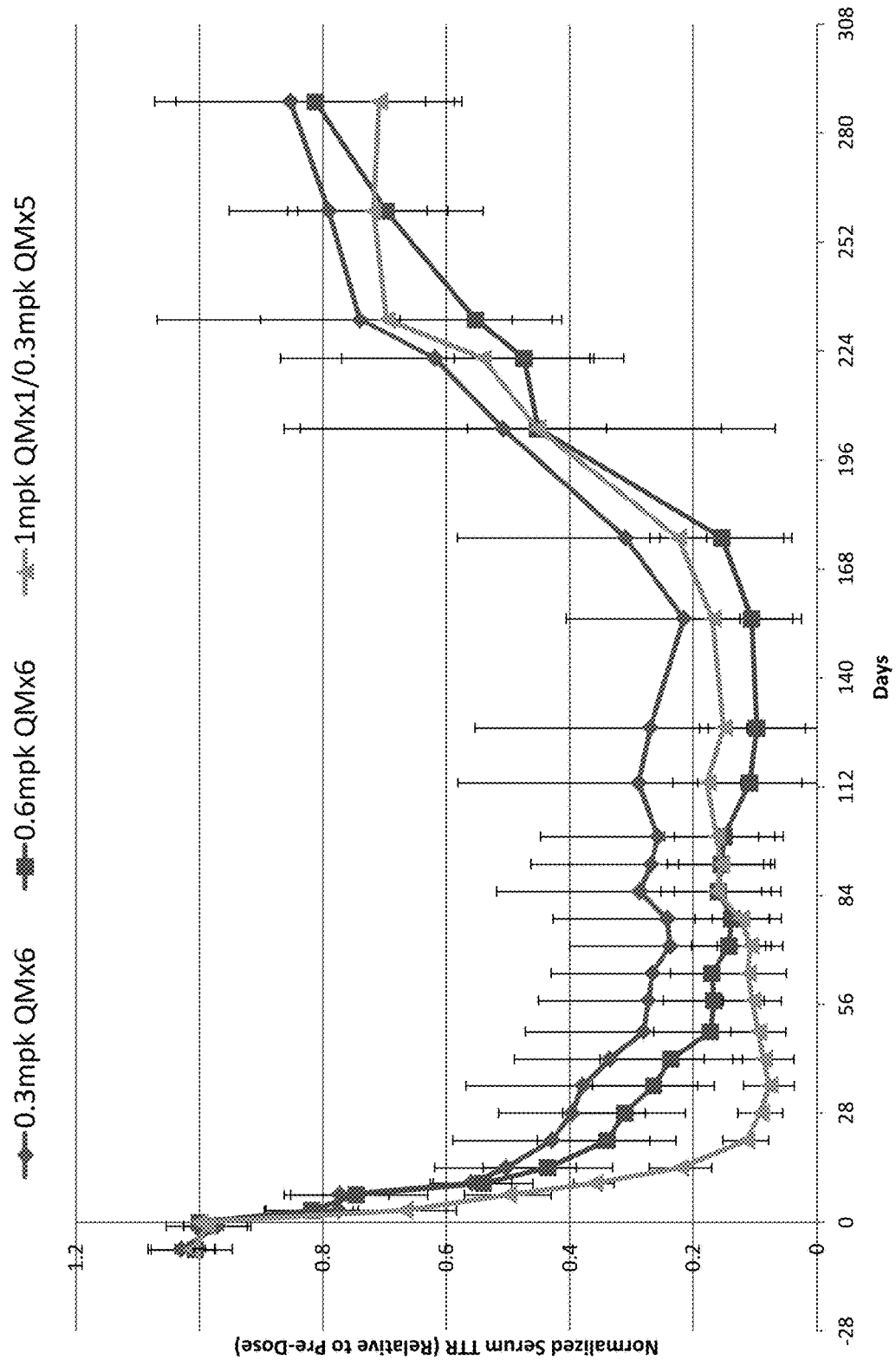
FIG. 13 is a graph depicting robust serum TTR suppression in Cynomologous monkeys following monthly subcutaneous administration of a 0.3 mg/kg dose of AD-65492 for six months (QM×6) or monthly subcutaneous administration of a 0.6 mg/kg dose of AD-65492 for six months (QM×6) or administration of a single 1 mg/kg initial dose of AD-65492 (QM×1) followed by a monthly 0.3 mg/kg dose of AD-65492 beginning at day 28 post-initial dose for five months (QM×5).

FIG. 13 provides the results of these studies, and demonstrates robust suppression of TTR achieved by AD-65492 after a monthly dose of 0.6 mg/kg for two months (QM×2), which is comparable to suppression of TTR expression following a 1 mg/kg initial dose. The data also demonstrate that AD-65492 provides about 80% sustained suppression of TTR expression after monthly dosing for two months at 0.3 mg/kg; three out of four monkeys achieved 60%-85% TTR suppression following a monthly 0.3 mg/kg does of AD-65492 for two months. Up to 90% suppression of TTR expression was demonstrated following a single 1 mg/kg dose, with a second dose of 0.3 mg/kg maintaining nadir for three weeks post dose second dose.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A method of prophylactically treating a human subject at risk for developing a TTR-associated disease, comprising administering to the subject a prophylactically effective amount of a double stranded ribonucleic acid (RNAi) agent,
    wherein the double stranded RNAi agent comprises a sense strand differing by no more than 4 modified nucleotides from the nucleotide sequence of 5'-usgsggauUfuCfAfUfguaaccaaga-3' (SEQ ID NO: 10) and an antisense strand differing by no more than 4 modified nucleotides from the nucleotide sequence 5'-usCfsuugGfuuAfcaugAfaAfucccasusc-3' (SEQ ID NO: 7),
    wherein a, c, g, and u are 2'-O-methyl (2'-OMe) A, C, G, and U; Af, Cf, Gf, and Uf are 2'-fluoro A, C, G, and U; and s is a phosphorothioate linkage,
    thereby prophylactically treating the subject.

2. The method of claim 1, wherein said subject carries a TTR gene mutation that is associated with the development of a TTR-associated disease.

3. The method of claim 1, wherein said TTR-associated disease is selected from the group consisting of senile systemic amyloidosis (SSA), systemic familial amyloidosis, familial amyloidotic polyneuropathy (FAP), familial amyloidotic cardiomyopathy (FAC), leptomeningeal/Central Nervous System (CNS) amyloidosis, and hyperthyroxinemia.

4. The method of claim 1, wherein said double stranded RNAi agent is administered to said subject by an administration means selected from the group consisting of subcutaneous, intravenous, intramuscular, intrabronchial, intrapleural, intraperitoneal, intraarterial, lymphatic, cerebrospinal, and any combinations thereof.

5. The method of claim 1, wherein said double stranded RNAi agent is administered to said subject via subcutaneous administration.

6. The method of claim 5, wherein the subcutaneous administration is self-administration.

7. The method of claim 6, wherein the self-administration is via a pre-filled syringe or auto-injector syringe.

8. The method of claim 1, wherein the double stranded RNAi agent is chronically administered to the subject.

9. The method of claim 1, wherein the sense strand differs by no more than 3 modified nucleotides from the nucleotide sequence of 5'-usgsggauUfuCfAfUfguaaccaaga-3' (SEQ ID NO: 10) and the antisense strand differs by no more than 3 modified nucleotides from the nucleotide sequence 5'-usCfsuugGfuuAfcaugAfaAfucccasusc-3' (SEQ ID NO: 7).

10. The method of claim 1, wherein the sense strand differs by no more than 2 modified nucleotides from the nucleotide sequence of 5'-usgsggauUfuCfAfUfguaaccaaga-3' (SEQ ID NO: 10) and the antisense strand differs by no more than 2 modified nucleotides from the nucleotide sequence 5'-usCfsuugGfuuAfcaugAfaAfucccasusc-3' (SEQ ID NO: 7).

11. The method of claim 1, wherein the sense strand differs by no more than 1 modified nucleotide from the nucleotide sequence of 5'-usgsggauUfuCfAfUfguaaccaaga-3' (SEQ ID NO: 10) and the antisense strand differs by no more than 1 modified nucleotide from the nucleotide sequence 5'-usCfsuugGfuuAfcaugAfaAfucccasusc-3' (SEQ ID NO: 7).

12. The method of claim 1, wherein the sense strand comprises the nucleotide sequence 5'-usgsggauUfuCfAfUfguaaccaaga-3' (SEQ ID NO: 10) and the antisense strand comprises the nucleotide sequence 5'-usCfsuugGfuuAfcaugAfaAfucccasusc-3' (SEQ ID NO: 7).

13. The method of claim 1, wherein the sense strand consists of the nucleotide sequence 5'-usgsggauUfuCfAfUfguaaccaaga-3' (SEQ ID NO: 10) and the antisense strand consists of the nucleotide sequence 5'-usCfsuugGfuuAfcaugAfaAfucccasusc-3' (SEQ ID NO: 7).

14. The method of any one of claims 1 and 9-13, wherein the double stranded RNAi agent further comprises at least one ligand.

15. The method of any one of claims 1 and 9-13, wherein the sense strand of the double stranded RNAi agent is conjugated to at least one ligand.

16. The method of claim 15, wherein the ligand is one or more GalNAc derivatives attached through a bivalent or trivalent branched linker.

17. The method of claim 15, wherein the ligand is

18. The method of claim 15, wherein the ligand is attached to the 3' end of the sense strand.

19. The method of claim 18, wherein the double stranded RNAi agent is conjugated to the ligand as shown in the following schematic

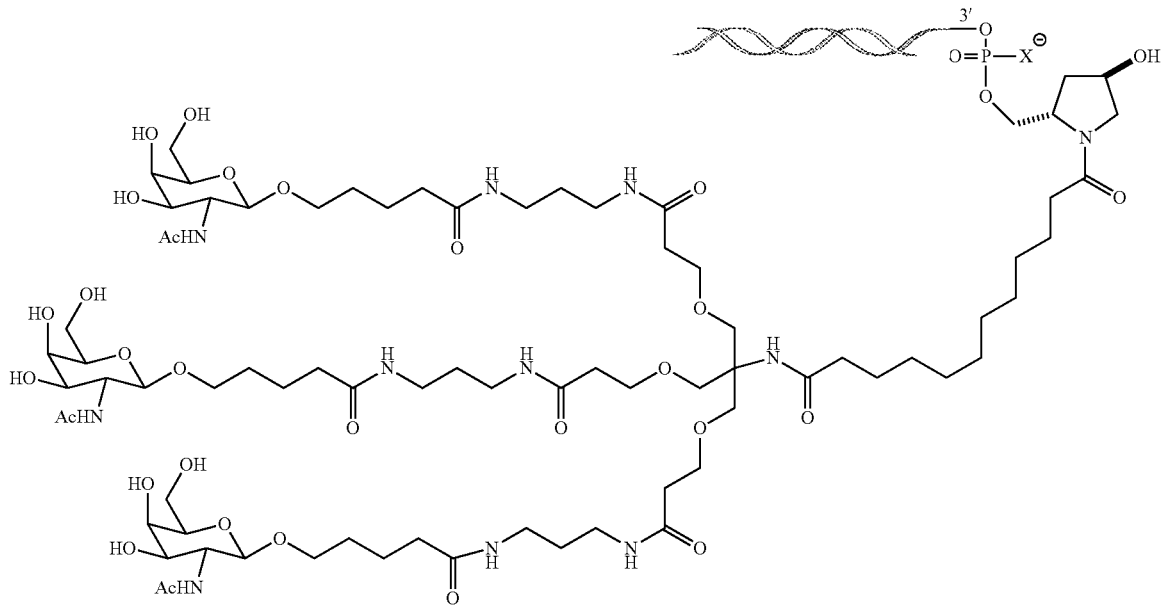

wherein X is O or S.

20. The method of claim 19, wherein the X is O.

21. A method of prophylactically treating a human subject at risk for developing a TTR-associated disease, comprising administering to the subject a prophylactically effective amount of a double stranded ribonucleic acid (RNAi) agent,
wherein the double stranded RNAi agent comprises a sense strand and an antisense strand, wherein the sense strand comprises the nucleotide sequence 5'-usgsggauUfuCfAfUfguaaccaagaL96-3' (SEQ ID NO: 10) and the antisense strand comprises the nucleotide sequence 5'-usCfsuugGfuuAfcaugAfaAfuccca-susc-3' (SEQ ID NO: 7)
wherein a, c, g, and u are 2'-O-methyl (2'-OMe) A, C, G, and U; Af, Cf, Gf, and Uf are 2'-fluoro A, C, G, and U; s is a phosphorothioate linkage; and L96 is N-[tris (GalNAc-alkyl)-amidodecanoyl)]-4-hydroxyprolinol,
thereby prophylactically treating the subject.

22. The method of claim 21, wherein the subject carries a TTR gene mutation that is associated with the development of a TTR-associated disease.

23. The method of claim 21, wherein the TTR-associated disease is selected from the group consisting of senile systemic amyloidosis (SSA), systemic familial amyloidosis, familial amyloidotic polyneuropathy (FAP), familial amyloidotic cardiomyopathy (FAC), leptomeningeal/Central Nervous System (CNS) amyloidosis, and hyperthyroxinemia.

24. The method of claim 21, wherein the double stranded RNAi agent is administered to said subject by an administration means selected from the group consisting of subcutaneous, intravenous, intramuscular, intrabronchial, intrapleural, intraperitoneal, intraarterial, lymphatic, cerebrospinal, and any combinations thereof.

25. The method of claim 21, wherein the double stranded RNAi agent is administered to the subject via subcutaneous administration.

26. The method of claim 25, wherein the subcutaneous administration is self-administration.

27. The method of claim 26, wherein the self-administration is via a pre-filled syringe or auto-injector syringe.

28. The method of claim 21, wherein the double stranded RNAi agent is chronically administered to the subject.

* * * * *

SEQUENCE LISTING

```
<160> NUMBER OF SEQ ID NOS: 262

<210> SEQ ID NO 1
<211> LENGTH: 938
<212> TYPE: DNA
<213> ORGANISM: Homo sapiens

<400> SEQUENCE: 1
gttgactaag tcaataatca gaatcagcag gtttgcagtc agattggcag ggataagcag      60
cctagctcag gagaagtgag tataaaagcc ccaggctggg agcagccatc acagaagtcc     120
actcattctt ggcaggatgg cttctcatcg tctgctcctc ctctgccttg ctggactggt     180
atttgtgtct gaggctggcc ctacgggcac cggtgaatcc aagtgtcctc tgatggtcaa     240
agttctagat gctgtccgag gcagtcctgc catcaatgtg gccgtgcatg tgttcagaaa     300
ggctgctgat gacacctggg agccatttgc ctctgggaaa accagtgagt ctggagagct     360
gcatgggctc acaactgagg aggaatttgt agaagggata tacaaagtgg aaatagacac     420
caaatcttac tggaaggcac ttggcatctc cccattccat gagcatgcag aggtggtatt     480
cacagccaac gactccggcc cccgccgcta caccattgcc gccctgctga gccctactc     540 ctattccacc acggctgtcg tcaccaatcc caaggaatga gggacttctc ctccagtgga     600
cctgaaggac gagggatggg atttcatgta accaagagta ttccatttt actaaagcag     660 tgttttcacc tcatatgcta tgttagaagt ccaggcagag acaataaaac attcctgtga     720
aaggcacttt tcattccact ttaacttgat tttttaaatt cccttattgt cccttccaaa     780
aaaaagagaa tcaaaatttt acaaagaatc aaaggaattc tagaaagtat ctgggcagaa     840
cgctaggaga gatccaaatt tccattgtct tgcaagcaaa gcacgtatta aatatgatct     900
gcagccatta aaaagacaca ttctgtaaaa aaaaaaa                             938

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugggauuuca uguaaccaag a                                               21

<210> SEQ ID NO 3
<211> LENGTH: 23
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 3
ucuugguuac augaaauccc auc                                           23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
gatgggattt catgtaacca aga                                           23

<210> SEQ ID NO 5
<211> LENGTH: 650
<212> TYPE: DNA
<213> ORGANISM: Homo sapiens

<400> SEQUENCE: 5
acagaagtcc actcattctt ggcaggatgg cttctcatcg tctgctcctc ctctgccttg    60
ctggactggt atttgtgtct gaggctggcc ctacgggcac cggtgaatcc aagtgtcctc   120
tgatggtcaa agttctagat gctgtccgag gcagtcctgc catcaatgtg gccgtgcatg   180
tgttcagaaa ggctgctgat gacacctggg agccatttgc ctctgggaaa accagtgagt   240
ctggagagct gcatgggctc acaactgagg aggaatttgt agaagggata tacaaagtgg   300
aaatagacac caaatcttac tggaaggcac ttggcatctc cccattccat gagcatgcag   360
aggtggtatt cacagccaac gactccggcc ccgccgcta caccattgcc gccctgctga   420 gccctactc ctattccacc acggctgtcg tcaccaatcc caaggaatga gggacttctc   480
ctccagtgga cctgaaggac gagggatggg atttcatgta accaagagta ttccattttt   540
actaaagcag tgttttcacc tcatatgcta tgttagaagt ccaggcagag acaataaaac   600
attcctgtga aaggcacttt tcattccaaa aaaaaaaaaa aaaaaaaaa              650

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
ucuugguuac augaaauccc auc                                           23

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 7
ucuugguuac augaaauccc auc                                           23

-continued

```
<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucuugguuac augaaauccc auc                                              23

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ucuugguuac augaaauccc auc                                              23

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ugggauuuca uguaaccaag a                                                21

<210> SEQ ID NO 11
<211> LENGTH: 16
<212> TYPE: PRT
<213> ORGANISM: Unknown
<220> FEATURE:
<223> OTHER INFORMATION: Description of Unknown: RFGF
      peptide

<400> SEQUENCE: 11

Ala Ala Val Ala Leu Leu Pro Ala Val Leu Leu Ala Leu Leu Ala Pro
1               5                   10                  15

<210> SEQ ID NO 12
<211> LENGTH: 11
<212> TYPE: PRT
<213> ORGANISM: Unknown
<220> FEATURE:
<223> OTHER INFORMATION: Description of Unknown: RFGF analogue
      peptide

<400> SEQUENCE: 12

Ala Ala Leu Leu Pro Val Leu Leu Ala Ala Pro
1               5                   10

<210> SEQ ID NO 13
<211> LENGTH: 13
<212> TYPE: PRT
<213> ORGANISM: Human immunodeficiency virus

<400> SEQUENCE: 13

Gly Arg Lys Lys Arg Arg Gln Arg Arg Pro Pro Gln
1               5                   10

<210> SEQ ID NO 14
```

```
<211> LENGTH: 16
<212> TYPE: PRT
<213> ORGANISM: Drosophila sp.

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugggauuuca uguaaccaag a                                             21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugggauuuca uguaaccaag a                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ugggauuuca tguaacaaag a                                             21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugggauuuca uguaaccaag a                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ugggauuuca tguaacaaag a                                             21
```

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugggauuuca uguaaccaag a                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugggauuuca uguaaccaag a                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugggauuuca uguaaccaag a                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose) nucleotide

<400> SEQUENCE: 23
ugggauuuca tguaacnaag a                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugggauuuca uguaaccaag a                                              21

<210> SEQ ID NO 25
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 25
ugggauuuca uguaaccaag a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
ugggauuuca tguaacaaag a                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ugggauuuca tguaacaaag a                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
ugggauuuca tguaacaaag a                                              21

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucuugguuac augaaauccc auc                                            23

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
```
ucuugguuac augaaauccc auc                                          23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
ucuugguuac augaaauccc auc                                          23

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucuugguuac augaaauccc auc                                          23

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ucuugguuac augaaauccc auc                                          23

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ucuugguuac augaaauccc auc                                          23

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ucuugguuac augaaauccc auc                                          23

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ucuugguuac augaaauccc auc                                                      23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
ucuugguuac augaaauccc auc                                                      23

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucuugguuac augaaauccc auc                                                      23

<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucuugguuac augaaauccc auc                                                      23

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ucuugguuac augaaauccc auc                                                      23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ucuugguuac augaaauccc auc                                                      23

<210> SEQ ID NO 42
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
ucuugguuac augaaauccc auc                                              23

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugggauuuca uguaaccaag a                                                21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ugggauuuca uguaaccaag a                                                21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ugggauuuca uguaaccaag a                                                21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ugggauuuca uguaaccaag a                                                21

<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ucuugguuac augaaauccc auc                                              23
```

```
<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ucuugguuac augaaauccc auc                                              23

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ucuugguuac augaaauccc auc                                              23

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ucuugguuac augaaauccc auc                                              23

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ugggauuuca uguaaccaag a                                                21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ugggauuuca uguaaccaag a                                                21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ugggauuuca uguaaccaag a                                                21

<210> SEQ ID NO 54
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ugggauuuca uguaaccaag a                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
ugggauuuca tguaacaaag a                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ugggauuuca uguaaccaag a                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
ugggauuuca tguaacaaag a                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ugggauuuca uguaaccaag a                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
```
uaggauuuca uguaaccaag a                    21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ugggauuuca uguaaccaag a                    21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ugggauuuca uguaaccaag a                    21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
ugggauuuca tguaacaaag a                    21

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggauuucaug uaaccaaga                       19

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ugggauuuca uguaaccaag a                    21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 65
ugggauuuca uguaaccaag a                                               21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ugggauuuca uguaaccaag a                                               21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ugggauuuca uguaaccaag a                                               21

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggauuucaug uaaccaaga                                                  19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ggauuucaug uaaccaaga                                                  19

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ugggauuuca uguaaccaag a                                               21

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 71
ggauuucaug uaaccaaga                                                        19

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ugggauuuca uguaaccaag a                                                     21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ugggauuuca tguaacaaag a                                                     21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose) nucleotide

<400> SEQUENCE: 74
ugggauuuca tguaacnaag a                                                     21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose) nucleotide

<400> SEQUENCE: 75
ugggauuuca tguaacnaag a                                                     21

<210> SEQ ID NO 76
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
ugggauuuca tguaacaaag a                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
ugggauuuca tguaacaaag a                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose) nucleotide

<400> SEQUENCE: 78
ugggauuuca tguaacnaag a                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ugggauuuca tguaacaaag a                                              21

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
```
ggauuucatg uaacaaaga                                        19

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose) nucleotide

<400> SEQUENCE: 81
ugggauuuca tguaacnaag a                                     21

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
ggauuucatg uaacaaaga                                        19

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
ugggauuuca tguaaccaag a                                     21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
ugggauuuca tguaaccaag a                                     21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 85
ugggauuuca tguaaccaag a                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
ugggauuuca tguaaccaag a                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ugggauuuca uguaaccaag a                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ugggauuuca uguaaccaag a                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ugggauuuca uguaaccaag a                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ugggauuuca uguaaccaag a                                              21

<210> SEQ ID NO 91
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ugggauuuca uguaaccaag a                                                 21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ugggauuuca uguaaccaag a                                                 21

<210> SEQ ID NO 93
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ucuugguuac augaaauccc auc                                               23

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ucuugguuac augaaauccc auc                                               23

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ucuugguuac augaaauccc auc                                               23

<210> SEQ ID NO 96
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucuugguuac augaaauccc auc                                               23

<210> SEQ ID NO 97
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 97
ucuugguuac augaaauccc auc                                                23

<210> SEQ ID NO 98
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucuugguuac augaaauccc auc                                                23

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ucuugguuac augaaauccc auc                                                23

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucuugguuac augaaauccc auc                                                23

<210> SEQ ID NO 101
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ucuugguuac augaaauccu auu                                                23

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
ucuugguuac augaaauccc auc                                                23

<210> SEQ ID NO 103
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 103
ucuugguuac augaaauccc auc                                              23

<210> SEQ ID NO 104
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ucuugguuac augaaauccc auc                                              23

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucuugguuac augaaauccc a                                                21

<210> SEQ ID NO 106
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ucuugguuac augaaauccc auc                                              23

<210> SEQ ID NO 107
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
ucuugguuac augaaauccc auc                                              23

<210> SEQ ID NO 108
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ucuugguuac augaaauccc auc                                              23

<210> SEQ ID NO 109
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 109
ucuugguuac augaaauccc auc                                             23

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ucuugguuac augaaauccu a                                               21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucuugguuac augaaauccc a                                               21

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
ucuugguuac augaaauccc auc                                             23

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ucuugguuac augaaauccc a                                               21

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ucuugguuac augaaauccc auc                                             23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 115
ucuugguuac augaaauccc auc                                               23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
ucuugguuac augaaauccc auc                                               23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
ucuugguuac augaaauccc auc                                               23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
ucuugguuac augaaauccc auc                                               23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
ucuugguuac augaaauccc auc                                               23

<210> SEQ ID NO 120
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
ucuugguuac augaaauccc auc                                              23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
ucuugguuac augaaauccc auc                                              23

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
ucuugguuac augaaauccc a                                                21

<210> SEQ ID NO 123
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ucuugguuac augaaauccc auc                                              23

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
ucuugguuac augaaauccc a                                                21

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 125
ucuugguuac augaaauccc auc                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
ucuugguuac augaaauccc auc                                              23

<210> SEQ ID NO 127
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ucuugguuac augaaauccc auc                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
ucuugguuac augaaauccc auc                                              23

<210> SEQ ID NO 129
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ucuugguuac augaaauccc auc                                              23

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucuugguuac augaaauccc auc                                              23
```

<210> SEQ ID NO 131
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ucuugguuac augaaauccc auc                                             23

<210> SEQ ID NO 132
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucuugguuac augaaauccc auc                                             23

<210> SEQ ID NO 133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ucuugguuac augaaauccc auc                                             23

<210> SEQ ID NO 134
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ucuugguuac augaaauccc auc                                             23

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
augggauuuc auguaaccaa a                                               21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
augggauuuc auguaaccaa a                                               21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
augggauuuc auguaaccaa a                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ugggauuuca uguaaccaag a                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugggauuuca uguaaccaag a                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ugggauuuca uguaaccaag a                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ugggauuuca uguaaccaag a                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uuucauguaa ccaagaguau u                                              21

<210> SEQ ID NO 143

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uuucauguaa ccaagaguau u                                             21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uuucauguaa ccaagaguau u                                             21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uguaaccaag aguauuccau u                                             21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uguaaccaag aguauuccau u                                             21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uguaaccaag aguauuccau u                                             21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aaccaagagu auuccauuuu u                                             21

<210> SEQ ID NO 149
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aaccaagagu auuccauuuu u                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aaccaagagu auuccauuuu u                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuuuuacuaa agcaguguuu u                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uuuuuacuaa agcaguguuu u                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uuuuuacuaa agcaguguuu u                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
uuacuaaagc aguguuuuca a                                              21

<210> SEQ ID NO 155
<211> LENGTH: 21
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 155
cuaaagcagu guuucaccu a                                          21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cuaaagcagu guuucaccu a                                          21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cuaaagcagu guuucaccu a                                          21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ggcagagaca auaaaacauu a                                         21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ggcagagaca auaaaacauu a                                         21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ggcagagaca auaaaacauu a                                         21

<210> SEQ ID NO 161
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 161
cagagacaau aaaacauucc u                                              21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
cagagacaau aaaacauucc u                                              21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
cagagacaau aaaacauucc u                                              21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
caauaaaaca uuccgugaa a                                               21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
caauaaaaca uuccgugaa a                                               21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
caauaaaaca uuccgugaa a                                               21

<210> SEQ ID NO 167
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 167
uuugguuaca ugaaauccca ucc                                              23

<210> SEQ ID NO 168
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
uuugguuaca ugaaauccca ucc                                              23

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uuugguuaca ugaaauccca ucc                                              23

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ucuugguuac augaaauccc auc                                              23

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ucuugguuac augaaauccc auc                                              23

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ucuugguuac augaaauccc auc                                              23

<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 173
ucuugguuac augaaauccc auc                                          23

<210> SEQ ID NO 174
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
aauacucuug guuacaugaa auc                                          23

<210> SEQ ID NO 175
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
aauacucuug guuacaugaa auc                                          23

<210> SEQ ID NO 176
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
aauacucuug guuacaugaa auc                                          23

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
aauggaauac ucuugguuac aug                                          23

<210> SEQ ID NO 178
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
aauggaauac ucuugguuac aug                                          23

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 179
aauggaauac ucuugguuac aug                                              23

<210> SEQ ID NO 180
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
aaaaauggaa uacucuuggu uac                                              23

<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
aaaaauggaa uacucuuggu uac                                              23

<210> SEQ ID NO 182
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
aaaaauggaa uacucuuggu uac                                              23

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
aaaacacugc uuuaguaaaa aug                                              23

<210> SEQ ID NO 184
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
aaaacacugc uuuaguaaaa aug                                              23

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 185
aaaacacugc uuuaguaaaa aug                                              23

<210> SEQ ID NO 186
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uugaaaacac ugcuuuagua aaa                                              23

<210> SEQ ID NO 187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uaggugaaaa cacugcuuua gua                                              23

<210> SEQ ID NO 188
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uaggugaaaa cacugcuuua gua                                              23

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
uaggugaaaa cacugcuuua gua                                              23

<210> SEQ ID NO 190
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uaauguuuua uugucucugc cug                                              23

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
```

```
uaauguuuua uugucucugc cug                                              23
```

<210> SEQ ID NO 192
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192

```
uaauguuuua uugucucugc cug                                              23
```

<210> SEQ ID NO 193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193

```
aggaauguuu uauugucucu gcc                                              23
```

<210> SEQ ID NO 194
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194

```
aggaauguuu uauugucucu gcc                                              23
```

<210> SEQ ID NO 195
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195

```
aggaauguuu uauugucucu gcc                                              23
```

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196

```
uuucacagga auguuuuauu guc                                              23
```

<210> SEQ ID NO 197
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197

```
uuucacagga auguuuuauu guc                                           23
```

<210> SEQ ID NO 198
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198

```
uuucacagga auguuuuauu guc                                           23
```

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199

```
augggauuuc auguaaccaa a                                             21
```

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200

```
augggauuuc auguaaccaa a                                             21
```

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201

```
augggauuuc auguaaccaa a                                             21
```

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202

```
ugggauuuca uguaaccaag a                                             21
```

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203

```
ugggauuuca uguaaccaag a                                             21
```

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ugggauuuca uguaaccaag a                                                   21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ugggauuuca uguaaccaag a                                                   21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uuucauguaa ccaagaguau u                                                   21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuucauguaa ccaagaguau u                                                   21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
uuucauguaa ccaagaguau u                                                   21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uguaaccaag aguauuccau u                                                   21

```
<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
uguaaccaag aguauuccau u                                              21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uguaaccaag aguauuccau u                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
aaccaagagu auuccauuuu u                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
aaccaagagu auuccauuuu u                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
aaccaagagu auuccauuuu u                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uuuuuacuaa agcaguguuu u                                              21
```

```
<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
uuuuuacuaa agcaguguuu u                                           21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uuuuuacuaa agcaguguuu u                                           21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uuacuaaagc aguguuuuca a                                           21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
cuaaagcagu guuucaccu a                                            21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cuaaagcagu guuucaccu a                                            21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cuaaagcagu guuucaccu a                                            21

<210> SEQ ID NO 222
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggcagagaca auaaaacauu a                                              21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ggcagagaca auaaaacauu a                                              21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ggcagagaca auaaaacauu a                                              21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cagagacaau aaaacauucc u                                              21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
cagagacaau aaaacauucc u                                              21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
cagagacaau aaaacauucc u                                              21

<210> SEQ ID NO 228
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
caauaaaaca uuccugugaa a                                              21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
caauaaaaca uuccugugaa a                                              21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
caauaaaaca uuccugugaa a                                              21

<210> SEQ ID NO 231
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uuugguuaca ugaaauccca ucc                                            23

<210> SEQ ID NO 232
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uuugguuaca ugaaauccca ucc                                            23

<210> SEQ ID NO 233
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uuugguuaca ugaaauccca ucc                                            23

<210> SEQ ID NO 234
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 234
ucuugguuac augaaauccc auc                                           23

<210> SEQ ID NO 235
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ucuugguuac augaaauccc auc                                           23

<210> SEQ ID NO 236
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucuugguuac augaaauccc auc                                           23

<210> SEQ ID NO 237
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ucuugguuac augaaauccc auc                                           23

<210> SEQ ID NO 238
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
aauacucuug guuacaugaa auc                                           23

<210> SEQ ID NO 239
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
aauacucuug guuacaugaa auc                                           23

<210> SEQ ID NO 240
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 240
aauacucuug guuacaugaa auc                                              23

<210> SEQ ID NO 241
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
aauggaauac ucuugguuac aug                                              23

<210> SEQ ID NO 242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
aauggaauac ucuugguuac aug                                              23

<210> SEQ ID NO 243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
aauggaauac ucuugguuac aug                                              23

<210> SEQ ID NO 244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
aaaaauggaa uacucuuggu uac                                              23

<210> SEQ ID NO 245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
aaaaauggaa uacucuuggu uac                                              23

<210> SEQ ID NO 246
<211> LENGTH: 23
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 246
aaaaauggaa uacucuuggu uac                                           23

<210> SEQ ID NO 247
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 247
aaaacacugc uuuaguaaaa aug                                           23

<210> SEQ ID NO 248
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 248
aaaacacugc uuuaguaaaa aug                                           23

<210> SEQ ID NO 249
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 249
aaaacacugc uuuaguaaaa aug                                           23

<210> SEQ ID NO 250
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 250
uugaaaacac ugcuuuagua aaa                                           23

<210> SEQ ID NO 251
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 251
uaggugaaaa cacugcuuua gua                                           23

<210> SEQ ID NO 252
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 252
uaggugaaaa cacugcuuua gua                                               23

<210> SEQ ID NO 253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uaggugaaaa cacugcuuua gua                                               23

<210> SEQ ID NO 254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uaauguuuua uugucucugc cug                                               23

<210> SEQ ID NO 255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uaauguuuua uugucucugc cug                                               23

<210> SEQ ID NO 256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
uaauguuuua uugucucugc cug                                               23

<210> SEQ ID NO 257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
aggaauguuu uauugucucu gcc                                               23

<210> SEQ ID NO 258
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 258
aggaauguuu uauugucucu gcc                                              23

<210> SEQ ID NO 259
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
aggaauguuu uauugucucu gcc                                              23

<210> SEQ ID NO 260
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uuucacagga auguuuauu guc                                               23

<210> SEQ ID NO 261
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
uuucacagga auguuuauu guc                                               23

<210> SEQ ID NO 262
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
uuucacagga auguuuauu guc                                               23
```